( 12 ) United States Patent
Kakiuchi et al.

(10) Patent No.: US 8,008,425 B2
(45) Date of Patent: Aug. 30, 2011

(54) THIOPHENE COMPOUND HAVING SULFONYL GROUP AND PROCESS FOR PRODUCING THE SAME

(75) Inventors: Nobuyuki Kakiuchi, Funabashi (JP); Hitoshi Furusho, Funabashi (JP); Naoki Otani, Funabashi (JP); Tatsuo Okauchi, Kitakyusyu (JP); Naoki Nakaie, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 352 days.

(21) Appl. No.: 12/064,003

(22) PCT Filed: Jul. 11, 2006

(86) PCT No.: PCT/JP2006/313734
§ 371 (c)(1),
(2), (4) Date: May 15, 2008

(87) PCT Pub. No.: WO2006/115305
PCT Pub. Date: Nov. 2, 2006

(65) Prior Publication Data
US 2009/0127491 A1 May 21, 2009

(30) Foreign Application Priority Data

Aug. 18, 2005 (JP) .................. 2005-237026
Apr. 14, 2006 (JP) .................. 2006-112269

(51) Int. Cl.
*C08G 75/00* (2006.01)
(52) U.S. Cl. ....... 528/373; 528/380; 528/377; 252/62.2; 252/500; 252/301.35; 562/118
(58) Field of Classification Search ............ 528/378, 528/380; 252/62.2, 500, 301.35
See application file for complete search history.

(56) References Cited

U.S. PATENT DOCUMENTS 5,888,941 A 3/1999 Bartroli et al.
(Continued)

FOREIGN PATENT DOCUMENTS

EP 1 215 224 A1 6/2002
(Continued)

OTHER PUBLICATIONS

Yakubov, A. P. et al., *Zhurnal Organicheskoi Khimii*, 1978, vol. 14, No. 3, pp. 641-650.

(Continued)

*Primary Examiner* — RAndy Gulakowski
*Assistant Examiner* — Shane Fang
(74) *Attorney, Agent, or Firm* — Birch, Stewart, Kolasch & Birch, LLP

(57) ABSTRACT

A thiophene compound having sulfonyl groups which is represented by the formula [1]. It has high heat resistance and high unsusceptibility to oxidation and can improve solubility and dispersibility in various solvents.

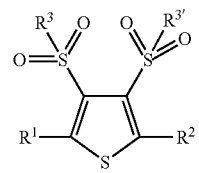

[1]

[In the formula, $R^1$ and $R^2$ each independently represents hydrogen, halogeno, cyano, etc.; and $R^3$ and $R^{3'}$ each independently represents $C_{1-20}$ alkyl, $C_{1-20}$ haloalkyl, phenyl optionally substituted by W, thienyl optionally substituted by W, etc. (W represents chlorine, etc.).]

23 Claims, 5 Drawing Sheets

U.S. PATENT DOCUMENTS

| | | | |
|---|---|---|---|
| 6,566,356 B2 | 5/2003 | Achard et al. | |
| 6,734,176 B2 | 5/2004 | Achard et al. | |
| 6,784,192 B2 | 8/2004 | Ozaki et al. | |
| 2002/0019383 A1 | 2/2002 | Achard et al. | |
| 2002/0077450 A1 | 6/2002 | Kirchmeyer et al. | |
| 2003/0119810 A1 | 6/2003 | Achard et al. | |
| 2003/0171531 A1 | 9/2003 | Ong et al. | |
| 2003/0220368 A1 | 11/2003 | Ozaki et al. | |
| 2004/0142982 A1 | 7/2004 | Mayorga et al. | |
| 2004/0157823 A1 | 8/2004 | Achard et al. | |
| 2004/0171790 A1* | 9/2004 | Baik et al. | 528/378 |
| 2006/0014822 A1 | 1/2006 | Rottlander et al. | |

FOREIGN PATENT DOCUMENTS

| | | |
|---|---|---|
| EP | 1 254 904 A1 | 11/2002 |
| EP | 1 329 476 A1 | 7/2003 |
| JP | 58-5362 A | 1/1983 |
| JP | 61-212579 A | 9/1986 |
| JP | 2000-26421 A | 1/2000 |
| JP | 2001-270883 A | 10/2001 |
| JP | 2002-206022 A | 7/2002 |
| JP | 2003-221434 A | 8/2003 |
| JP | 2003-525269 A | 8/2003 |
| JP | 2004-517143 A | 6/2004 |
| WO | WO-97/05131 A1 | 2/1997 |
| WO | WO-01/64633 A1 | 9/2001 |
| WO | WO-02/057242 A2 | 7/2002 |
| WO | WO-2004/058739 A1 | 7/2004 |
| WO | WO-2004/063179 A1 | 7/2004 |

OTHER PUBLICATIONS

Jones, E. et al., *Journal of the Chemical Society*, 1965, pp. 7018-7019.
Shermolovich, Y. G. et al., *Heteroatom Chemistry*, 1998, vol. 9, No. 2 pp. 151-154.
Hartman, G. D. et al., *Journal of Heterocyclic Chemistry*, 1990, vol. 27, No. 2, pp. 127-134.
Miyake, Y. et al., *Chemical Communications*, Jan. 2005, No. 3, pp. 411-413.
Hagberg, E. C. et al., *Macromolecules*, 2004, vol. 37, No. 13, pp. 4748-4754.
Christov, V. C. et al., *Heterocyclic Communications*, 2003, vol. 9, No. 6, pp. 629-634.
Georgiadis, T. M. et al., *Journal of Combinatorial Chemistry*, 2004, vol. 6, No. 2, pp. 224-229.
Stephens, C. E. et al., *Bioorganic & Medicinal Chemistry*, 2001, vol. 9, pp. 1123-1132.
Stephens, C. E. et al., *Journal of Heterocyclic Chemistry*, 1999, vol. 36, pp. 659-665.
Stephens, C. E. et al., *Journal of Heterocyclic Chemistry*, 1998, vol. 35, pp. 927-931.
Bartoli, J. et al., *Journal of Medicinal Chemistry*, 1998, vol. 41, pp. 1855-1868.
Noto, R. et al., *Journal of the Chemical Society, Perkin Transactions 2: Physical Organic Chemistry*, 1988, vol. 6, pp. 887-892.
Simonnin, M. P. et al., *Journal of Fluorine Chemistry*, 1987, vol. 36, No. 4. pp. 439-448.
Noto, R. et al., *Journal of the Chemical Society, Perkin Transactions 2: Physical Organic Chemistry*, 1987, vol. 6, pp. 689-694.
Stoyanovich, F. M. et al., *Izvestiya Akademii Nauk SSSR, Seriya Khimicheskaya*, 1985, No. 4, pp. 868-874.
Consiglio, G. et al., *Journal of the Chemical Society, Perkin Transactions 2: Physical Organic Chemistry*, 1985, No. 4, pp. 519-522.
Gronowitz, S. et al., *Journal of Heterocyclic Chemistry*, 1977, Vol. 14, pp. 281-288.
Gol'dfarb, Y. L. et al., *Izvestiya Akademii Nauk SSSR, Seriya Khimicheskaya*, 1973, No. 10, pp. 2290-2295.
Stoyanovich, F. M. et al., *Izvestiya Akademii Nauk SSSR, Seriya Khimicheskaya*, 1973, vol. 10, pp. 2285-2290.
Camaggi, C. M. et al., Journal of the Chemical Society, Perkin Transactions 2: Physical Organic Chemistry, 1972, No. 11, pp. 1594-1597.
Spinelli, D. et al., Journal of the Chemical Society, Perkin Transactions 2: Physical Organic Chemistry, 1972, No. 4, pp. 441-445.
Stoyanovich, F. M. et al., *Khimiya Geterotsiklicheskikh Soedinenii*, 1967, No. 5, pp. 823-826.
Chrzaszezewska, A. et al., *Lodz. Towarz. Nauk., Wydzial III, Acta Chim.*, 1965, vol. 10, pp. 65-69.
Jones, E. et al., *Tetrahedron*, 1965, vol. 21, pp. 2413-2420.
Jeganathan, S. et al., *Tetrahedron Letters*, 1982, vol. 23, No. 46, pp. 4763-4764.
Padwa, A. et al., *Organic Syntheses*, 1997, vol. 74, pp. 147-157.
Padwa, A. et al., *Journal of Organic Chemistry*, 1991, vol. 56, No. 8, pp. 2713-2720.
Padwa, A. et al., *Journal of Organic Chemistry*, 1990, vol. 55, No. 16, pp. 4801-4807.

* cited by examiner

THIOPHENE COMPOUND HAVING SULFONYL GROUP AND PROCESS FOR PRODUCING THE SAME

TECHNICAL FIELD

This invention relates to a thiophene compound having sulfonyl group(s) and a process for producing the same, and more specifically, to a sulfonyl group-containing thiophene monomer, oligomer and polymer and production processes thereof.

BACKGROUND ART

In recent years, aromatic compounds and heterocyclic compounds having the π conjugated system are used for their luminescence characteristics and electron/hole transport ability characteristics in a variety of electronic devices such as organic electroluminescence devices, cells and semiconductors.

Organic electroluminescence devices can be roughly classified into high molecular devices and low molecular devices. As an adequate degree of ready carrier mobility and appropriate fluorescence emission characteristics are required especially for low molecular devices, it is needed to freely vary the band gaps of derivatives of π conjugated compounds upon their developments. Their film characteristics are also important, and in particular, they are required to form stable amorphous films (see Non-patent Document 1, Non-patent Document 2, Non-patent Document 3, and Patent Document 1).

For cells, it is required to control the oxidation-reduction potential of a compound (see, for example, Non-patent Document 4). Concerning an electrode active material for cells, in particular, it is necessary to control its oxidation-reduction potential below the decomposition voltage of an electrolyte solution. It is, therefore, an important endeavor to control the oxidation-reduction potential.

With respect to semiconductors, π conjugated polymers are widely investigated to achieve bandgap narrowing. However, π conjugated polymers involve a problem in that their structures are hardly controllable because they generally have low solubility in solvents and cannot be handled with ease.

As another method for narrowing the bandgaps of π conjugated systems, there is a method that widens the π conjugated systems two-dimensionally (see Non-patent Document 5 and Non-patent Document 6). These materials are also insoluble in solvents so that they cannot be handled with ease.

Further, general π conjugated polymers can behave as impurity semiconductors by doping. It is, however, difficult to stably prepare p-type and n-type semiconductors with a single material.

As electroconductive polymers, polymers of aniline or aniline derivatives are used widely. In general, these polymers are synthesized by electrolytic polymerization or chemical polymerization and are doped with a Lewis acid or the like to impart electroconductivity. Such an aniline polymer has been reported to show a very high specific electric conductivity when it is formed into a thin film by dispersing it in water or an organic solvent to formulate a varnish and spin-coating the varnish on a substrate or the like (see Patent Document 2).

Aniline polymers are, however, accompanied by a drawback that they are not resistant to oxidation by oxygen in air and depending on the degree of oxidation, their specific electric conductivities may be significantly impaired. Moreover, it has also been pointed out that benzidine, a carcinogenic compound, may mix in as a byproduct upon polymerization (see Non-patent Document 5 and Non-patent Document 7).

Polymers of pyrrole are also known as electroconductive polymers. Like aniline polymers, however, these pyrrole polymers are insoluble and infusible and therefore, they involve a problem that they can be hardly formed into films.

On the other hand, polythiophene compounds generally have low dispersibility or solubility in organic or aqueous solvents, and therefore, can be hardly formed into polymer films, dispersions or solutions. Taking process aspects into consideration, the low dispersibility or solubility poses a serious problem upon their application as electroconductive polymer materials.

As a countermeasure, it is conducted to introduce a hydrocarbon group to the 3-position of a thiophene monomer such that the corresponding polythiophene can be provided with improved solubility in an organic solvent (see Patent Document 3).

Further, Bayer AG has reported a varnish of a water-soluble electroconductive polymer as formulated by subjecting (3,4-ethylenedioxy)thiophene or its derivative to oxidative polymerization while using polystyrenesulfonic acid as a dopant (see Patent Document 4).

Polythione-based electroconductive polymers are, however, accompanied by a problem in that their solid concentrations at which they can be stably dispersed are extremely low, thereby making it difficult to control the thickness of each coating film.

As described above, the conventionally-known electroconductive polymers involve one or more of the various problems for their physical properties upon their formation into electroconductive thin films. There is, accordingly, an outstanding demand for a new material having the potency of solving these problems.

Non-patent Document 1:
Polymer, Vol. 24, p. 748, 1983 (U.K.)
Non-patent Document 2:
Japanese Journal of Applied Physics, Vol. 25, p. 775, 1986
Non-patent Document 3:
Applied Physics Letters, Vol. 51, p. 913, 1987 (U.S.A)
Non-patent Document 4:
Electrochemistry (written in Japanese), Vol. 54, p. 306, 1986
Non-patent Document 5:
Synthetic Metals, Vol. 69, p. 599-600, 1995 (U.S.A.)
Non-patent Document 6:
Journal of the American Chemical Society, 117(25), 6791-6792, 1995 (U.S.A.)
Non-patent Document 7:
Achievement Report on Research and Development of Electroconductive Polymer Materials, 218-251, March, 1989 [Book and Reference Material Library, New Energy and Industrial Technology Development Organization (NEDO)]
Patent Document 1:
U.S. Pat. No. 4,356,429 A
Patent Document 2:
U.S. Pat. No. 5,720,903 A
Patent Document 3:
JP-A 2003-221434
Patent Document 4:
JP-A 2002-206022

DISCLOSURE OF THE INVENTION

Problem to be Solved by the Invention

With the foregoing circumstances in view, the present invention has as objects thereof the provision of a thiophene compound having sulfonyl group(s), equipped with high resistance to heat and oxidation and capable of improving the solubility or dispersibility in various solvent and a process for its production.

Means for Solving the Problems

To achieve the above-described objects, the present inventors focused attention on the thiophene skeleton having high resistance of heat and oxidation, and with a view to providing improved solubility or dispersibility in various solvents, have conducted screening and research on thiophene compounds having new molecular structures.

Specifically, the present inventors focused attention on conventionally-unreported thiophene compounds having sulfonyl group(s), and as their production processes, made an investigation about an oxidation process that provides a thiophene compound having sulfonyl group(s) from a thiophene compound having sulfanyl group(s) via an oxidation reaction. A variety of oxidation reaction systems were investigated in the course of the investigation. It was, however, difficult to find out a practical production process, because of a problem that the yield was low as the reaction system became a multicomponent system or the reaction was not brought to completion. For example, in the below-described oxidation reaction that oxidizes 3,4-bis(butylsulfanyl)thiophene 1a to obtain 3,4-bis(butane-1-sulfonyl)thiophene 2a, the use of potassium permanganate as an oxidant in a methylene chloride/water two-phase system failed to provide the target product and the starting material recovery was 77%. Similarly, the use of a hydrogen peroxide solution as an oxidant in a methanol solvent system also failed to provide the target product, and the starting material recovery was 69%.

TABLE 1

[Chemical Formula 1]

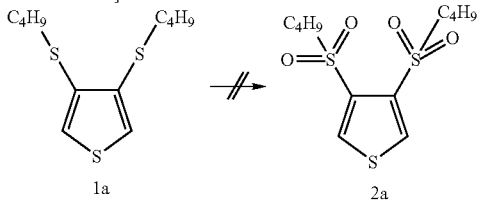

| Entry | Oxidant | Solvent | temp. | time | 1a | 2a |
|---|---|---|---|---|---|---|
| 1 | KMnO$_4$ 4.2 eq. | CH$_2$Cl$_2$/H$_2$O = 1/2 | r.t. | 20 h | 77 | N.D.* |
| 2 | H$_2$O$_2$ 4.2 eq. | MeOH | r.t. | 24 h | 69 | N.D.* |

*Not determined

The present inventors, therefore, conducted an extensive investigation on additives to be incorporated in the above-described oxidation reaction system. As a result, it was found that the oxidation reaction of the sulfanyl groups selectively and efficiently proceeds by using an oxidant and a metal catalyst in combination. That finding has led to the finding of a practical process for the production of a thiophene compound having sulfonyl group(s) and also to the finding of a sulfonyl group-containing thiophene monomer and oligomer which are equipped with excellent heat resistance, have better solubility or dispersibility in organic solvents than the conventional products, and are expected to find utility as electroconductive polymers, and hence, the present invention has been completed.

Described specifically, the present invention provides:
1. A bissulfonylthiophene compound represented by the following formula [1]:

[Chemical Formula 2]

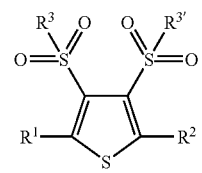

[1]

wherein R$^1$ and R$^2$ each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or a dialkoxyboryl group having 1 to 10 carbon atoms, R$^3$ and R$^{3'}$ each independently represent an alkyl group having 1 to 20 carbon atoms, haloalkyl group having 1 to 20 carbon atoms, phenyl group which may be substituted by W, or thienyl group which may be substituted by W, or R$^3$ and R$^{3'}$ are fused together to represent an alkylene group which has 1 to 3 carbon atoms and may be substituted by W, phenylene group which may be substituted by W, or —(CH$_2$)q-SO$_2$—(CH$_2$)q-SO$_2$—(CH$_2$)q- in which q stands for an integer of from 1 to 3, W represents a halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', N-naphthyl-N-anthranylamino group which may be substituted by W', trialkylsilyl group having 1 to 10 carbon atoms, alkylcarbonyl group having 1 to 10 carbon atoms, alkoxycarbonyl group having 1 to 10 carbon atoms, or phenyl group which may be substituted by W', and W' represents an alky group having 1 to 10 carbon atoms, haloalkyl group having 1 to 10 carbon atoms, or alkoxy group having 1 to 10 carbon atoms, 2. The bissulfonylthiophene compound as described above under 1, wherein R$^1$ and R$^2$ each independently represent a phenyl group which may be substituted by W, naphthyl group which may be substituted by W, or anthranyl group which may be substituted by W, 3. The bissulfonylthiophene compound as described above under 2, wherein W represents a diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', or N-naphthyl-N-anthranylamino group which may be substituted by W', 4. A monosulfonylthiophene compound represented by the following formula [24]:

[Chemical Formula 3]

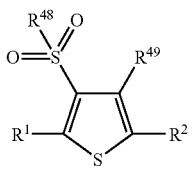

[24]

wherein $R^1$ and $R^2$ have the same meanings as defined above, $R^{48}$ represents an alkyl group having 1 to 20 carbon atoms, haloalkyl group having 1 to 20 carbon atoms, phenyl group which may be substituted by W, or thienyl group which may be substituted by W, $R^{49}$ represents a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 10 carbon atoms, monoalkylamino group having 1 to 10 carbon atoms, dialkylamino group having 1 to 10 carbon atoms, or phenyl group which may be substituted by W, and W has the same meaning as defined above, 5. The monosulfonylthiophene compound as described above under 4, wherein $R^1$ and $R^2$ each independently represent a phenyl group which may be substituted by W, naphthyl group which may be substituted by W, or anthranyl group which may be substituted by W.

6. The monosulfonylthiophene compound as described above under 5, wherein W represents a diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', or N-naphthyl-N-anthranylamino group which may be substituted by W', 7. A sulfonylthiophene oligomer compound represented by the following formula [2]:

[Chemical Formula 4]

wherein $R^3$ and $R^{3'}$ have the same meanings as defined above, $R^5$ and $R^6$ each independently represent an alkyl group having 1 to 20 carbon atoms, haloalkyl group having 1 to 20 carbon atoms, phenyl group which may be substituted by W, or thienyl group which may be substituted by W, $R^4$ and $R^7$ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 10 carbon atoms, monoalkylamino group having 1 to 10 carbon atoms, dialkylamino group having 1 to 10 carbon atoms, or phenyl group which may be substituted by W, W has the same meaning as defined above, m, n and o each independently stand for 0 or an integer of 1 or greater, p stands for 0 or an integer of 1 or greater, and m, n, o and p satisfy m+n+o≧1 and 1≦m+n+o+p≦50, Z is at least one divalent organic group selected from the following formulas [3] to [11]:

[Chemical Formula 5]

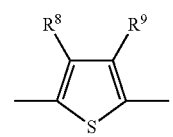

[3]

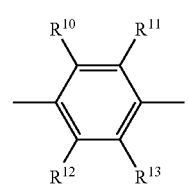

[4]

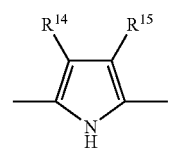

[5]

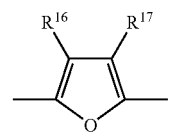

[6]

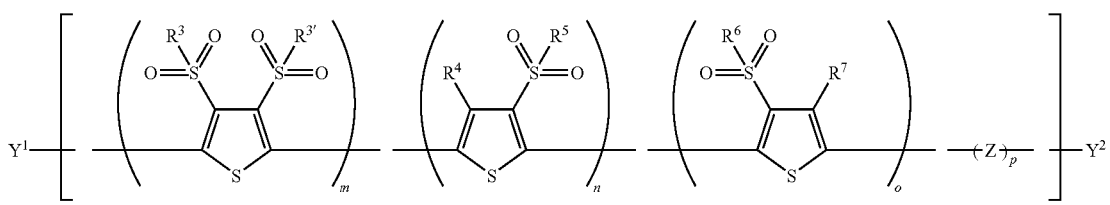

[2]

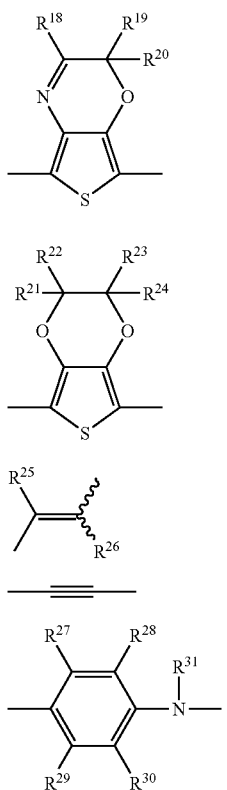

[Chemical Formula 6]

[12]

[13]

[14]

—Z—Q    [15]

wherein $R^8$ to $R^{30}$ each independently represent a hydrogen atom, alkyl group having 1 to 20 carbon atoms, haloalkyl group having 1 to 20 carbon atoms, alkoxy group having 1 to 10 carbon atoms, alkylthio group having 1 to 20 carbon atoms, dialkylamino group having 1 to 10 carbon atoms, or phenyl group which may be substituted by W, W has the same meaning as defined above, $R^{31}$ represents a hydrogen atom, alkyl group having 1 to 20 carbon atoms, haloalkyl group having 1 to 20 carbon atoms, alkoxy group having 1 to 10 carbon atoms, or phenyl group which may be substituted by W', and W' has the same meaning as defined above, and $Y^1$ and $Y^2$ each independently represent at least one monovalent organic group selected from the following formulas [12] to [15]:

wherein $R^3$ to $R^7$ and Z have the same meanings as defined above, Q are both end groups of said sulfonylthiophene oligomer compound and each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, and W has the same meaning as defined above, 8. The sulfonylthiophene oligomer compound as described above under 7, wherein Z is a divalent organic group represented by the formula [3], 9. A sulfonylthiophene polymer compound represented by the following formula [25]:

[Chemical Formula 7]

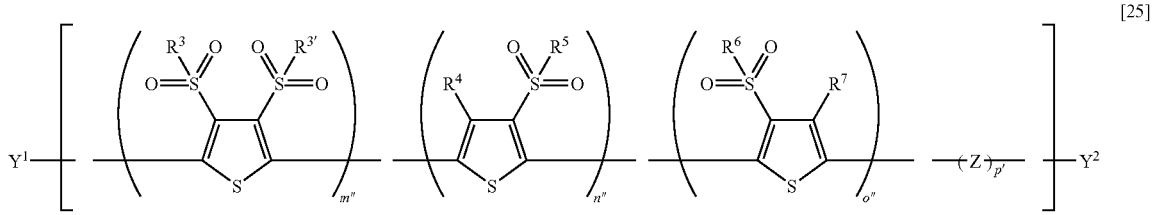

[25]

wherein $R^3$, $R^{3'}$, $R^5$, $R^6$, $R^4$, $R^7$, Z, $Y^1$ and $Y^2$ have the same meanings as defined above, m", n" and o" each independently stand for 0 or an integer of 1 or greater, p' stands for 0 or an integer of 1 or greater, and m", n", o" and p' satisfy m"+n"+o"≧1 and 50<m"+n"+o"+p'<5,000, 10. The sulfonylthiophene polymer compound as described above under 9, wherein Z is a divalent organic group represented by the formula [3], 11. A sulfonylthiophene oligomer compound represented by the following formula [16]:

[Chemical Formula 8]

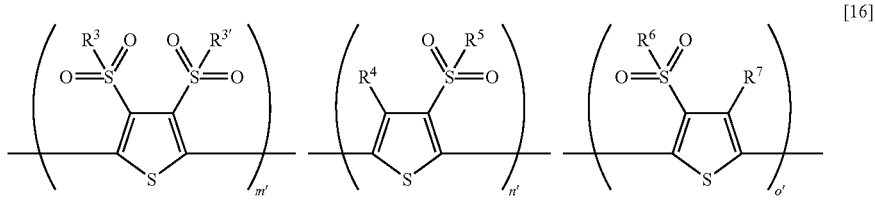

[16]

wherein $R^3$, $R^{3'}$, $R^5$, $R^6$, $R^4$ and $R^7$ have the same meanings as defined above, and m', n' and o' each independently stand for 0 or an integer of 1 or greater, and m', n' and o' satisfy 2<m'+n'+o'<50, with a proviso that both end groups of said sulfonylthiophene oligomer compound each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, and W has the same meaning as defined above, 12. A sulfonylthiophene polymer compound represented by the following formula [26]:

[Chemical Formula 9]

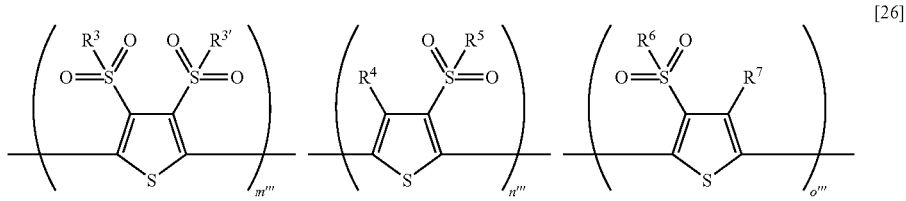

[26]

wherein $R^3$, $R^{3'}$, $R^5$, $R^6$, $R^4$ and $R^7$ have the same meanings as defined above, and m'", n'" and o'" each independently stand for 0 or an integer of 1 or greater, and m'", n'" and o'" satisfy 50<m'"+n'"+o'"<5,000, with a proviso that both end groups of said sulfonylthiophene polymer compound each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, and W has the same meaning as defined above, 13. A sulfonylthiophene polymer compound obtained by subjecting at least one sulfonylthiophene oligomer compound, which is selected from sulfonylthiophene oligomer compounds as described above under 7 and 11, to electrolytic oxidative polymerization or chemical oxidative polymerization, 14. A process for the production of a sulfonylthiophene polymer compound, which includes subjecting at least one sulfonylthiophene oligomer compound, which is selected from sulfonylthiophene oligomer compounds as described above under 7 and 11, to electrolytic oxidative polymerization or chemical oxidative polymerization, 15. A sulfonylthiophene polymer compound obtained by subjecting at least one compound, which is selected from bissulfonylthiophene compound as described above under 1, a monosulfonylthiophene compound as described under 4 and sulfonylthiophene oligomer compounds as described above under 7 and 11, to catalytic polymerization, 16. A process for the production of a sulfonylthiophene polymer compound, which includes subjecting at least one compound, which is selected from bissulfonylthiophene compound as described above under 1, a monosulfonylthiophene compound as described above under 4 and sulfonylthiophene oligomer compounds as described above under 7 and 11, to catalytic polymerization, 17. A process for the production of a sulfonylthiophene compound represented by the following formula [18]:

[Chemical Formula 11]

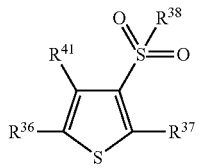

[18]

wherein $R^{36}$ and $R^{37}$ each independently represent a hydrogen atom, cyano group, phenyl group which may be substituted by W", hydroxyl group, amino group, formyl group, carboxyl group, alkyl group having 1 to 20 carbon atoms, haloalkyl group having 1 to 20 carbon atoms, monoalkylamino group having 1 to 10 carbon atoms, or dialkylamino group having 1 to 10 carbon atoms, $R^{38}$ represents an alkyl group having 1 to 20 carbon atoms, haloalkyl group having 1 to 20 carbon atoms, or phenyl group which may be substituted by W", $R^{41}$ represents a hydrogen atom, halogen atom, cyano group, nitro group, phenyl group which may be substituted by W", hydroxyl group, mercapto group, amino group, formyl group, carboxyl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, or —S—$R^{40}$, $R^{40}$ represents a hydrogen atom, alkyl group having 1 to 20 carbon atoms, or phenyl group which may be substituted by W", and W" represents a cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, alkylcarbonyl group having 1 to 10 carbon atoms, alkoxycarbonyl group having 1 to 10 carbon atoms, or phenyl group, which includes reacting, in the presence of an oxidant and a metal catalyst, a sulfanylthiophene compound represented by the following formula [17]:

[Chemical Formula 10]

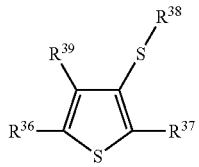

[17]

wherein $R^{36}$, $R^{37}$ and $R^{38}$ have the same meaning as described above, $R^{39}$ represents a hydrogen atom, halogen atom, cyano group, nitro group, phenyl group which may be substituted by W", hydroxyl group, mercapto group, amino group, formyl group, carboxyl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, or —S—$R^{40}$, and, $R^{40}$ and W" has the same meaning as defined above, 18. A process as described above under 17, wherein said metal catalyst is at least one metal catalyst selected from ruthenium catalysts, titanium catalysts and aluminum catalysts, 19. A sulfonylbithiophene compound represented by the following formula [19]:

[Chemical Formula 12]

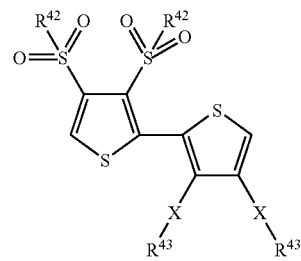

[19]

wherein X represents —S— or —S(O)$_2$—, $R^{42}$ and $R^{43}$ each independently represent an alkyl group having 1 to 20 carbon atoms, haloalkyl group having 1 to 20 carbon atoms, or phenyl group which may be substituted by W, and W has the same meaning as defined above, 20. A sulfonylbithiophene compound represented by the following formula [20]:

[Chemical Formula 13]

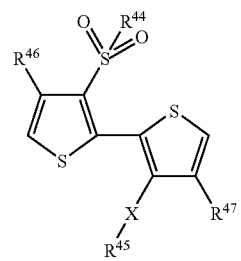

[20]

wherein X has the same meaning as defined above, $R^{44}$ and $R^{45}$ each independently represent an alkyl group having 1 to 20 carbon atoms, haloalkyl group having 1 to 20 carbon atoms, or phenyl group which may be substituted by W, $R^{46}$ and $R^{47}$ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, or phenyl group which may be substituted by W, and W has the same meaning as defined above, 21. A sulfonylbithiophene compound represented by the following formula [21]:

[Chemical Formula 14]

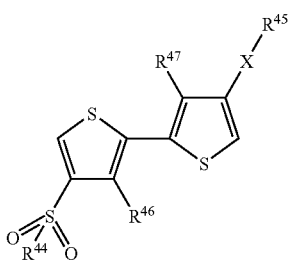

[21]

wherein X, $R^{44}$, $R^{45}$, $R^{46}$ and $R^{47}$ have the same meanings as defined above, 22. A sulfonylbithiophene compound represented by the following formula [22]:

[Chemical Formula 15]

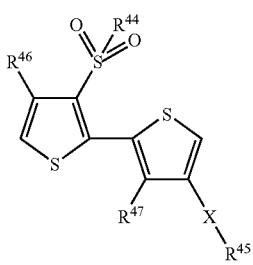

[22]

wherein X, $R^{44}$, $R^{45}$, $R^{46}$ and $R^{47}$ have the same meanings as defined above, 23. A sulfonylbithiophene compound represented by the following formula [23]:

[Chemical Formula 16]

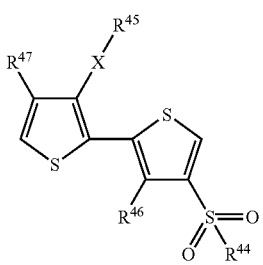

[23]

wherein X, $R^{44}$, $R^{45}$, $R^{46}$ and $R^{47}$ have the same meanings as defined above, 24. A process for the production of a bissulfanylbutadiene compound represented by the following formula [29]:

[Chemical Formula 19]

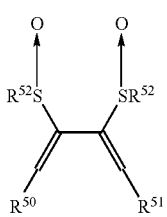

[29]

wherein $R^{50}$ and $R^{51}$ each independently represent a hydrogen atom, halogen atom, cyano group, phenyl group which may be substituted by W'', alkyl group having 1 to 10 carbon atoms, or haloalkyl group having 1 to 10 carbon atoms, $R^{52}$ represents a hydrogen atom, alkyl group having 1 to 10 carbon atoms, or phenyl group which may be substituted by W'', and W'' represents a halogen atom, cyano group, nitro group, alkyl group having 1 to 10 carbon atoms, haloalkyl group having 1 to 10 carbon atoms, alkenyl group having 1 to 10 carbon atoms, alkynyl group having 1 to 10 carbon atoms, alkoxy group having 1 to 10 carbon atoms, or phenyl group, which includes reacting, in the presence of a base, a butynediol compound represented by the following formula [27]:

[Chemical Formula 17]

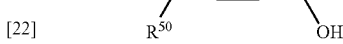

[27]

wherein $R^{50}$ and $R^{51}$ have the same meanings as defined above, with a sulfenyl compound represented by the following formula [28]:

[Chemical Formula 18]

$R^{52}SX$   [28]

wherein $R^{52}$ has the same meanings as defined above, and X represents a halogen atom, 25. A process for the production of a bissulfonylbutadiene compound represented by the following formula [30]:

[Chemical Formula 21]

[30]

wherein $R^{50}$, $R^{51}$ and $R^{52}$ have the same meanings as defined above, which includes reacting a bissulfanylbutadiene compound represented by the following formula [29]:

[Chemical Formula 20]

[29]

wherein $R^{50}$, $R^{51}$ and $R^{52}$ have the same meanings as defined above, with an organic oxidant, 26. A process for the production of a 3,4-bissulfonylthiolane compound represented by the following formula [3]:

[Chemical Formula 23]

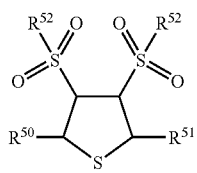

[31]

wherein $R^{50}$, $R^{51}$ and $R^{52}$ have the same meanings as defined above, which includes reacting a bissulfonylbutadiene compound represented by the following formula [30]:

[Chemical Formula 22]

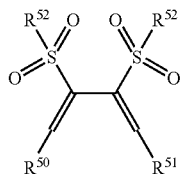

[30]

wherein $R^{50}$, $R^{51}$ and $R^{52}$ have the same meanings as defined above, with a metal sulfide, 27. A process for the production of a 3,4-bissulfonylsulfuran compound represented by the following formula [32]:

[Chemical Formula 25]

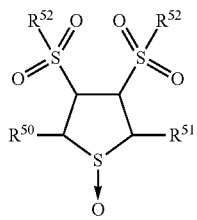

[32]

wherein $R^{50}$, $R^{51}$ and $R^{52}$ have the same meanings as defined above, which includes reacting a 3,4-bissulfonylthiolane compound represented by the following formula [31]:

[Chemcial Formula 24]

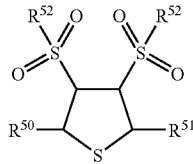

[31]

wherein $R^{50}$, $R^{51}$ and $R^{52}$ have the same meanings as defined above, with an organic oxidant, 28. A process for the production of a 3,4-bissulfonyldihydrothiophene compound represented by the following formula [33]:

[Chemical Formula 27]

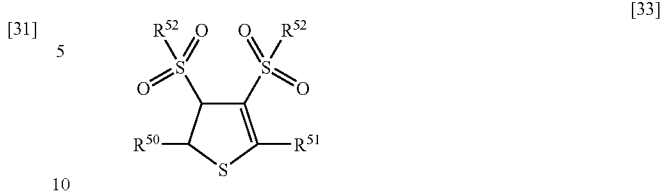

[33]

wherein $R^{50}$, $R^{51}$ and $R^{52}$ have the same meanings as defined above, which includes reacting a 3,4-bissulfonylsulfuran compound represented by the following formula [32]:

[Chemical Formula 26]

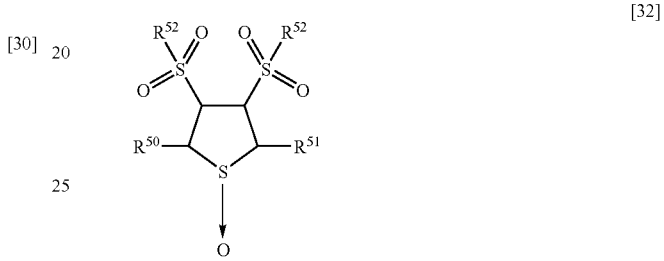

[32]

wherein $R^{50}$, $R^{51}$ and $R^{52}$ have the same meanings as defined above, with an organic anhydride in the presence of an organic acid catalyst, 29. A process for the production of a 3-sulfonylthiophene compound represented by the following formula [34]:

[Chemical Formula 29]

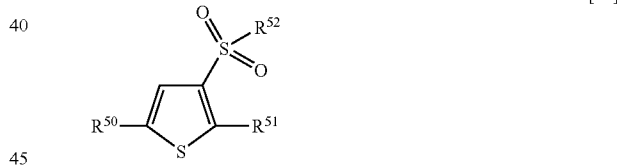

[34]

wherein $R^{50}$, $R^{51}$ and $R^{52}$ have the same meanings as defined above, which includes reacting a 3,4-bissulfonylsulfuran compound represented by the following formula [32]:

[Chemical Formula 28]

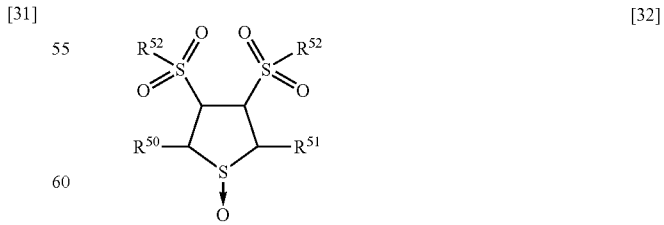

[32]

wherein $R^{50}$, $R^{51}$ and $R^{52}$ have the same meanings as defined above, with an organic acid anhydride in the presence of organic acid catalyst, and then causing elimination with a base, 30. A process for the production of a 3,4-bissulfonylthiophene compound represented by the following formula [35]:

[Chemical Formula 31]

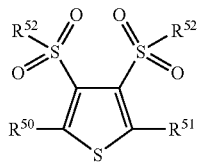

[35]

wherein $R^{50}$, $R^{51}$ and $R^{52}$ have the same meanings as defined above, which includes oxidizing a 3,4-bissulfonyldihydrothiophene compound represented by the following formula [33]:

[Chemical Formula 30]

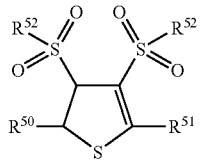

[33]

wherein $R^{50}$, $R^{51}$ and $R^{52}$ have the same meanings as defined above, with an inorganic oxidant, 31. An active material for cells, including at least one compound selected from a sulfonylthiophene oligomer compound as defined above under any one of 7, 8 and 11 and a sulfonylthiophene polymer compound as defined above under any one of 9, 10 and 12, 32. An electrode material including at least one compound selected from a sulfonylthiophene oligomer compound as defined above under any one of 7, 8 and 11 and a sulfonylthiophene polymer compound as described above under any one of 9, 10 and 12, 33. An organic electroluminescence material including at least one compound selected from a sulfonylthiophene oligomer compound as defined above under any one of 7, 8 and 11 and a sulfonylthiophene polymer compound as defined above under any one of 9, 10 and 12, 34. A p-type semiconductor formed by oxidizing at least one compound, which is selected from a sulfonylthiophene oligomer compound as defined above under any one of 7, 8 and 11 and a sulfonylthiophene polymer compound as defined above under any one of 9, 10 and 12, with an oxidant or by electrochemical doping, 35. An n-type semiconductor formed by reducing at least one compound, which is selected from a sulfonylthiophene oligomer compound as defined above under 7, 8 and 11 and a sulfonylthiophene polymer compound as defined above under 9, and 12, with a reductant or by electrochemical doping, 36. A semiconductor device fabricated by using at least one compound selected from a sulfonylthiophene oligomer compound as defined above under any one of 7, 8 and 11 and a sulfonylthiophene polymer compound as defined above under any one of 9, 10 and 12, 37. An organic electroluminescence device fabricated by using at least one compound selected from a sulfonylthiophene oligomer compound as defined above under any one of 7, 8 and 11 and a sulfonylthiophene polymer compound as defined above under any one of 9, 10 and 12, 38. An all-solid-state organic solar cell fabricated by using at least one compound selected from a sulfonylthiophene oligomer compound as defined above under any one of 7, 8 and 11 and a sulfonylthiophene polymer compound as defined above under any one of 9, 10 and 12, 39. A dye-sensitized solar cell fabricated by using at least one compound selected from a sulfonylthiophene oligomer compound as defined above under any one of 7, 8 and 11 and a sulfonylthiophene polymer compound as defined above under any one of 9, 10 and 12, 40. A capacitor electrode formed by using at least one compound selected from a sulfonylthiophene oligomer compound as defined above under any one of 7, 8 and 11 and a sulfonylthiophene polymer compound as defined above under any one of claims 9, 10 and 12, 41. An actuator formed by using at least one compound selected from a sulfonylthiophene oligomer compound as defined above under any one of 7, 8 and 11 and a sulfonylthiophene polymer compound as defined above under any one of 9, 10 and 12, 42. A solid electrolyte for capacitors, comprising at least one compound selected from a sulfonylthiophene oligomer compound as defined above under any one of 7, 8 and 11 and a sulfonylthiophene polymer compound as defined above under any one of 9, 10 and 12, 43. An antenna material including at least one compound selected from a sulfonylthiophene oligomer compound as defined above under any one of 7, 8 and 11 and a sulfonylthiophene polymer compound as defined above under any one of 9, 10 and 12, 44. A sensor formed by using at least one compound selected from a sulfonylthiophene oligomer compound as defined above under any one of 7, 8 and 11 and a sulfonylthiophene polymer compound as defined above under any one of 9, 10 and 12, and 45. A fuel cell separator including at least one compound selected from a sulfonylthiophene oligomer compound as defined above under any one of 7, 8 and 11 and a sulfonylthiophene polymer compound as defined above under any one of 9, 10 and 12.

Effects of the Invention

According to the invention, there can be provided production processes for a sulfonyl group-containing thiophene monomer and oligomer, which are equipped with excellent heat resistance, have better solubility or dispersibility in organic solvents than the conventional products and are expected find utility as electroconductive polymers, and production processes for polymers from these monomer and oligomer.

The oxidation reaction used in the process according to the invention for the production of the sulfonylthiophene compound can oxidize the sulfanyl side chains with high yield and high selectivity without being accompanied by oxidation of the thiophene ring of the sulfanylthiophene compound, and therefore, can serve as a practical process for the production of thiophene compounds having a wide variety of sulfonyl groups.

The sulfonyl group-containing thiophene compounds and polythiophene compounds according to the invention are equipped with excellent heat resistance, have better solubility or dispersibility in organic solvents than the conventional products, and moreover, permit easy control of an electrochemical oxidation-reduction potential. In addition, the bandgaps of the compounds themselves are very narrow so that they are equipped with strong fluorescence emission characteristics. Moreover, these thiophene compounds exhibit p-type or n-type semiconductor characteristics by an oxidant or reductant or electrochemical doping.

Further, these compounds can be readily formed into thin films by vapor deposition, spin coating, dipping, casting, screen printing or the like, and therefore, can be applied as active materials for cells or electrode materials, materials for electroluminescence devices, p-type or n-type semiconductors, semiconductor devices, nonlinear optical materials, and the like. Furthermore, the sulfonylthiophene compounds according to the invention can be suitably used as sensors, fluorescence filters, organoelectronic devices, organic electroluminescence devices, organic electrochromic devices, all-solid-state organic solar cells, dye-sensitized solar cells, capacitor electrodes, actuators, separators for fuel cells, solid electrolytes for capacitors, electromagnetic shielding films, antistatic films, IR protection films, UV protection films, antenna materials, nonlinear optical materials, etc.

BRIEF DESCRIPTION OF THE DRAWINGS

FIG. 2 is a diagram showing cyclic volutammetry of a thiophene derivative 4a.

BEST MODE FOR CARRYING OUT THE INVENTION

Figure 1:
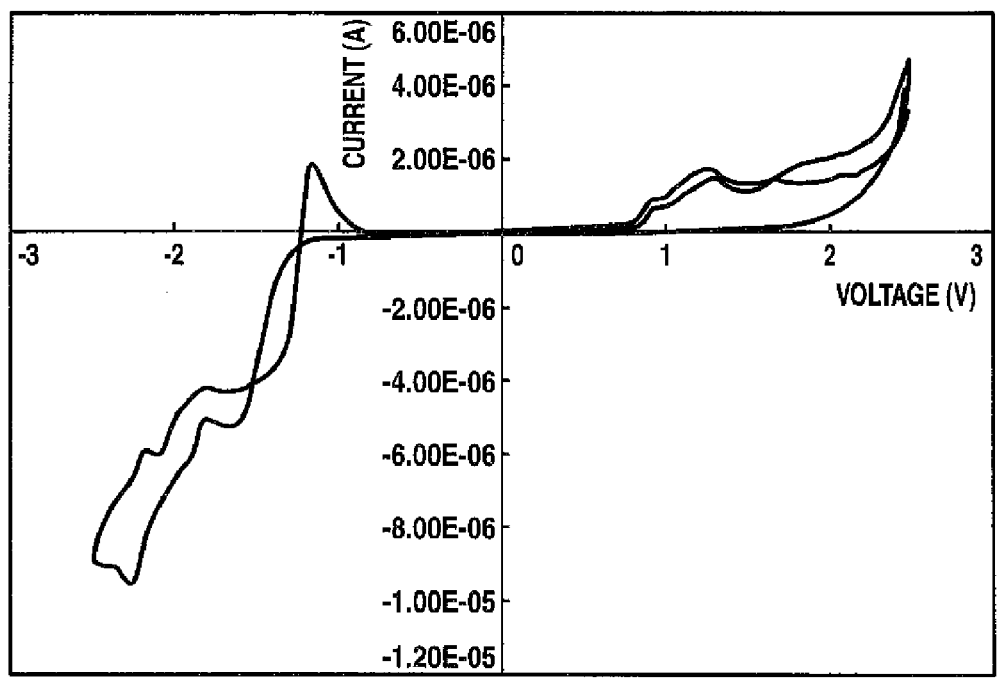
FIG. 1 is a diagram showing cyclic volutammetry of a thiophene derivative 4b.

The invention will hereinafter be described in further detail.

It is to be noted that in this specification, "n" means "normal", "i" means "iso", "s" means "secondary", "t" means "tertiary", "c" means "cyclo", "o" means "ortho", "m" means "meta", "p" means "para", "Me" means "methyl group", "Et" means "ethyl group", "Pr" means "propyl group", "Bu" means "butyl group", "Pen" means "pentyl group", "Hex" means "hexyl group", and "Ph" means "phenyl group".

The sulfonylthiophene compounds in the invention are represented by the above-described formulas [1] and [24], respectively.

In the formulas [1] and [24], $R^1$ and $R^2$ each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or a dialkoxyboryl group having 1 to 10 carbon atoms.

Illustrative of the halogen atom are a fluorine atom, chlorine atom, bromine atom and iodine atom.

Specific examples of the alkyl group having 1 to 20 carbon atoms include methyl, ethyl, n-propyl, i-propyl, c-propyl, n-butyl, i-butyl, s-butyl, t-butyl, c-butyl, n-pentyl, 1-methyl-n-butyl, 2-methyl-n-butyl, 3-methyl-n-butyl, 1,1-dimethyl-n-propyl, c-pentyl, 2-methyl-c-butyl, n-hexyl, 1-methyl-n-pentyl, 2-methyl-n-pentyl, 1,1-dimethyl-n-butyl, 1-ethyl-n-butyl, 1,1,2-trimethyl-n-propyl, c-hexyl, 1-methyl-c-pentyl, 1-ethyl-c-butyl, 1,2-dimethyl-c-butyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-dodecyl.

Specific examples of the haloalkyl group having 1 to 20 carbon atoms include $CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2Cl$, $CHCl_2$, $CCl_3$, $CH_2CH_2Cl$, $CH_2Br$, $CHBr_2$, $CBr_3$, $CH_2CH_2Br$, $CF_2CF_2CF_3$, $CF_2CF_2CF_2CF_2CF_2CF_3$, and $CH_2CH_2CF_2CF_2CF_2CF_3$.

Specific examples of the monoalkylamino group having 1 to 10 carbon atoms include NHMe, NHEt, NHPr-n, NHPr-i, NHBu-n, NHBu-i, NHBu-s, NHBu-t, NHPen-n, $NHCHEt_2$, and NHHex-n.

Specific examples of the dialkylamino group having 1 to 10 carbon atoms include $NMe_2$, $NEt_2$, $N(Pr-n)_2$, $N(Pr-i)_2$, $N(Bu-n)_2$, $N(Bu-i)_2$, $N(Bu-s)_2$, $N(Bu-t)_2$, $N(Pen-n)_2$, $N(CHEt_2)_2$, and $N(Hex-n)_2$.

Specific examples of the trialkylstannyl group having 1 to 10 carbon atoms include $SnMe_3$, $SnEt_3$, $Sn(Pr-n)_3$, $Sn(Pr-i)_3$, $Sn(Bu-n)_3$, $Sn(Bu-i)_3$, $Sn(Bu-s)_3$, and $Sn(Bu-t)_3$.

Specific examples of the trialkylsilyl group having 1 to 10 carbon atoms include $SiMe_3$, $SiEt_{31}$ $Si(Pr-n)_3$, $Si(Pr-i)_3$, $Si(Bu-n)_3$, $Si(Bu-i)_3$, $Si(Bu-s)_3$, and $Si(Bu-t)_3$.

Specific examples of the dialkoxyboryl group having 1 to 10 carbon atoms include $B(OMe)_2$, $B(OEt)_2$, $B(OPr-n)_2$, $B(OPr-i)_2$, $B(OBu-n)_2$, $B(OBu-i)_2$, $B(OBu-s)_2$, $B(OBu-t)_2$, and $B(-O-C(Me)_2-C(Me)_2-O-)$.

W represents a halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', N-naphthyl-N-anthranylamino group which may be substituted by W', trialkylsilyl group having 1 to 10 carbon atoms, alkylcarbonyl group having 1 to 10 carbon atoms, alkoxycarbonyl group having 1 to 10 carbon atoms, or phenyl group which may be substituted by W'. W' represents an alky group having 1 to 10 carbon atoms, haloalkyl group having 1 to 10 carbon atoms, or alkoxy group having 1 to 10 carbon atoms.

In the above case, specific examples of the alkenyl group having 1 to 10 carbon atoms include $CH=CH_2$, $CH=CHMe$, $CH=CHEt$, $CH=CMe_2$, $CH=CEt_2$, $CMe=CH_2$, $CMe=CHMe$, $CMe=CMe_2$, $CH_2CH=CH_2$, $CH_2CH=CHMe$, $CH_2CH=CHEt$, $CH_2CMe=CH_2$, $CH_2CH_2CH=CH_2$, $CH_2CH_2CH=CHMe$, $CH_2CH=CMe_{21}$ $CHMeCH=CH_2$, $CH_2CMe=CHMe$, $CHMeCH=CHMe$, $CH_2CMe=CHEt$, $CH_2CH_2CH=CMe_2$, $CH_2CMe=CMe_2$, and $CH=C=CH_2$.

Specific examples of the alkynyl group having 1 to 10 carbon atoms include C≡CMe, C≡CEt, CH₂C≡CH, CH₂C≡CMe, CH₂C≡CEt, CH₂CH₂C≡CH, CH₂CH₂C≡CMe, CHMeC≡CH, and CHMeC≡CMe.

Specific examples of the alkoxy group having 1 to 10 carbon atoms include OMe, OEt, OPr-n, OPr-i, OBu-n, OBu-i, OBu-s, OBu-t, OPen-n, OCHEt₂, OHex-n, OCHMe(Pr-n), OCHMe(Bu-n), OCHEt(Pr-n), and OCH₂CH₂CHMe₂. Specific examples of the alkylthio group having 1 to 10 carbon atoms include SMe, SEt, SPr-n, SPr-i, SBu-n, SBu-i, SBu-s, SBu-t, SPen-n, SCHEt₂, SHex-n, SCHMe(Pr-n), SCHMe(Bu-n), SCHEt(Pr-n), and SCH₂CH₂CHMe₂.

Specific examples of the alkylcarbonyl group having 1 to 10 carbon atoms include C(O)Me, C(O)Et, C(O)Pr-n, C(O)Pr-i, C(O)Bu-n, C(O)Bu-i, C(O)Bu-s, C(O)Bu-t, C(O)Pen-n, C(O)CHEt₂, and C(O)Hex-n.

Specific examples of the alkoxycarbonyl group having 1 to 10 carbon atoms include OC(O)Me, OC(O)Et, OC(O)Pr-n, OC(O)Pr-i, OC(O)Bu-n, OC(O)Bu-i, OC(O)Bu-s, OC(O)Bu-t, OC(O)Pen-n, OC(O)CHEt₂, and OC(O)Hex-n.

It is to be noted that specific examples of the alkyl group having 1 to 20 carbon atoms and the haloalkyl group having 1 to 20 carbon atoms are as mentioned above.

Specific examples of the phenyl group which may be substituted by W include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-chlorophenyl, m-chlorophenyl, p-chlorophenyl, o-bromophenyl, m-bromophenyl, p-bromophenyl, o-fluorophenyl, p-fluorophenyl, o-methoxyphenyl, m-methoxyphenyl, p-methoxyphenyl, o-trifluoromethoxyphenyl, p-trifluoromethoxyphenyl, o-nitrophenyl, m-nitrophenyl, p-nitrophenyl, o-dimethylaminophenyl, m-dimethylaminophenyl, p-dimethylaminophenyl, p-cyanophenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 3,5-dichlorophenyl, 3,5-dibromophenyl, 3,5-difluorophenyl, 3,5-dinitrophenyl, 3,5-dicyanophenyl, 2,4,6-trimethylphenyl, 2,4,6-tristrifluoromethylphenyl, 2,4,6-trimethoxyphenyl, 2,4,6-tristrifluoromethoxyphenyl, 2,4,6-trichlorophenyl, 2,4,6-tribromophenyl, 2,4,6-trifluorophenyl, o-biphenylyl, m-biphenylyl, and p-biphenylyl.

Specific examples of the naphthyl group which may be substituted by W include 1-naphthyl, 2-naphthyl, 2-butyl-1-naphthyl, 3-butyl-1-naphthyl, 4-butyl-1-naphthyl, 5-butyl-1-naphthyl, 6-butyl-1-naphthyl, 7-butyl-1-naphthyl, 8-butyl-1-naphthyl, 1-butyl-2-naphthyl, 3-butyl-2-naphthyl, 4-butyl-2-naphthyl, 5-butyl-2-naphthyl, 6-butyl-2-naphthyl, 7-butyl-2-naphthyl, 8-butyl-2-naphthyl, 2-hexyl-1-naphthyl, 3-hexyl-1-naphthyl, 4-hexyl-1-naphthyl, 5-hexyl-1-naphthyl, 6-hexyl-1-naphthyl, 7-hexyl-1-naphthyl, 8-hexyl-1-naphthyl, 1-hexyl-2-naphthyl, 3-hexyl-2-naphthyl, 4-hexyl-2-naphthyl, 5-hexyl-2-naphthyl, 6-hexyl-2-naphthyl, 7-hexyl-2-naphthyl, 8-hexyl-2-naphthyl, 2-octyl-1-naphthyl, 3-octyl-1-naphthyl, 4-octyl-1-naphthyl, 5-octyl-1-naphthyl, 6-octyl-1-naphthyl, 7-octyl-1-naphthyl, 8-octyl-1-naphthyl, 1-octyl-2-naphthyl, 3-octyl-2-naphthyl, 4-octyl-2-naphthyl, 5-octyl-2-naphthyl, 6-octyl-2-naphthyl, 7-octyl-2-naphthyl, 8-octyl-2-naphthyl, 2-phenyl-1-naphthyl, 3-phenyl-1-naphthyl, 4-phenyl-1-naphthyl, 5-phenyl-1-naphthyl, 6-phenyl-1-naphthyl, 7-phenyl-1-naphthyl, 8-phenyl-1-naphthyl, 1-phenyl-2-naphthyl, 3-phenyl-2-naphthyl, 4-phenyl-2-naphthyl, 5-phenyl-2-naphthyl, 6-phenyl-2-naphthyl, 7-phenyl-2-naphthyl, 8-phenyl-2-naphthyl, 2-methoxy-1-naphthyl, 3-methoxy-1-naphthyl, 4-methoxy-1-naphthyl, 5-methoxy-1-naphthyl, 6-methoxy-1-naphthyl, 7-methoxy-1-naphthyl, 8-methoxy-1-naphthyl, 1-methoxy-2-naphthyl, 3-methoxy-2-naphthyl, 4-methoxy-2-naphthyl, 5-methoxy-2-naphthyl, 6-methoxy-2-naphthyl, 7-methoxy-2-naphthyl, 8-methoxy-2-naphthyl, 2-ethoxy-1-naphthyl, 3-ethoxy-1-naphthyl, 4-ethoxy-1-naphthyl, 5-ethoxy-1-naphthyl, 6-ethoxy-1-naphthyl, 7-ethoxy-1-naphthyl, 8-ethoxy-1-naphthyl, 1-ethoxy-2-naphthyl, 3-ethoxy-2-naphthyl, 4-ethoxy-2-naphthyl, 5-ethoxy-2-naphthyl, 6-ethoxy-2-naphthyl, 7-ethoxy-2-naphthyl, 8-ethoxy-2-naphthyl, 2-butoxy-1-naphthyl, 3-butoxy-1-naphthyl, 4-butoxy-1-naphthyl, 5-butoxy-1-naphthyl, 6-butoxy-1-naphthyl, 7-butoxy-1-naphthyl, 8-butoxy-1-naphthyl, 1-butoxy-2-naphthyl, 3-butoxy-2-naphthyl, 4-butoxy-2-naphthyl, 5-butoxy-2-naphthyl, 6-butoxy-2-naphthyl, 7-butoxy-2-naphthyl, 8-butoxy-2-naphthyl, 2-amino-1-naphthyl, 3-amino-1-naphthyl, 4-amino-1-naphthyl, 5-amino-1-naphthyl, 6-amino-1-naphthyl, 7-amino-1-naphthyl, 8-amino-1-naphthyl, 1-amino-2-naphthyl, 3-amino-2-naphthyl, 4-amino-2-naphthyl, 5-amino-2-naphthyl, 6-amino-2-naphthyl, 7-amino-2-naphthyl, 8-amino-2-naphthyl, 2-(N,N-dimethylamino)-1-naphthyl, 3-(N,N-dimethylamino)-1-naphthyl, 4-(N,N-dimethylamino)-1-naphthyl, 5-(N,N-dimethylamino)-1-naphthyl, 6-(N,N-dimethylamino)-1-naphthyl, 7-(N,N-dimethylamino)-1-naphthyl, 8-(N,N-dimethylamino)-1-naphthyl, 1-(N,N-dimethylamino)-2-naphthyl, 3-(N,N-dimethylamino)-2-naphthyl, 4-(N,N-dimethylamino)-2-naphthyl, 5-(N,N-dimethylamino)-2-naphthyl, 6-(N,N-dimethylamino)-2-naphthyl, 7-(N,N-dimethylamino)-2-naphthyl, 8-(N,N-dimethylamino)-2-naphthyl, 2-(N,N-diphenylamino)-1-naphthyl, 3-(N,N-diphenylamino)-1-naphthyl, 4-(N,N-diphenylamino)-1-naphthyl, 5-(N,N-diphenylamino)-1-naphthyl, 6-(N,N-diphenylamino)-1-naphthyl, 7-(N,N-diphenylamino)-1-naphthyl, 8-(N,N-diphenylamino)-1-naphthyl, 1-(N,N-diphenylamino)-2-naphthyl, 3-(N,N-diphenylamino)-2-naphthyl, 4-(N,N-diphenylamino)-2-naphthyl, 5-(N,N-diphenylamino)-2-naphthyl, 6-(N,N-diphenylamino)-2-naphthyl, 7-(N,N-diphenylamino)-2-naphthyl, and 8-(N,N-diphenylamino)-2-naphthyl.

Specific examples of the anthranyl group which may be substituted by W include 1-anthranyl, 2-anthranyl, 9-anthranyl, 2-butyl-1-anthranyl, 3-butyl-1-anthranyl, 4-butyl-1-anthranyl, 5-butyl-1-anthranyl, 6-butyl-1-anthranyl, 7-butyl-1-anthranyl, 8-butyl-1-anthranyl, 9-butyl-1-anthranyl, 10-butyl-1-anthranyl, 1-butyl-2-anthranyl, 3-butyl-2-anthranyl, 4-butyl-2-anthranyl, 5-butyl-2-anthranyl, 6-butyl-2-anthranyl, 7-butyl-2-anthranyl, 8-butyl-2-anthranyl, 9-butyl-2-anthranyl, 10-butyl-2-anthranyl, 1-butyl-9-anthranyl, 2-butyl-9-anthranyl, 3-butyl-9-anthranyl, 4-butyl-9-anthranyl, 10-butyl-9-anthranyl, 2-hexyl-1-anthranyl, 3-hexyl-1-anthranyl, 4-hexyl-1-anthranyl, 5-hexyl-1-anthranyl, 6-hexyl-1-anthranyl, 7-hexyl-1-anthranyl, 8-hexyl-1-anthranyl, 9-hexyl-1-anthranyl, 10-hexyl-1-anthranyl, 1-hexyl-2-anthranyl, 3-hexyl-2-anthranyl, 4-hexyl-2-anthranyl, 5-hexyl-2-anthranyl, 6-hexyl-2-anthranyl, 7-hexyl-2-anthranyl, 8-hexyl-2-anthranyl, 9-hexyl-2-anthranyl, 10-hexyl-2-anthranyl, 1-hexyl-9-anthranyl, 2-hexyl-9-anthranyl, 3-hexyl-9-anthranyl, 4-hexyl-9-anthranyl, 10-hexyl-9-anthranyl, 2-octyl-1-anthranyl, 3-octyl-1-anthranyl, 4-octyl-1-anthranyl, 5-octyl-1-anthranyl, 6-octyl-1-anthranyl, 7-octyl-1-anthranyl, 8-octyl-1-anthranyl, 9-octyl-1-anthranyl, 10-octyl-1-anthranyl, 1-octyl-2-anthranyl, 3-octyl-2-anthranyl, 4-octyl-2-anthranyl, 5-octyl-2-anthranyl, 6-octyl-2-anthranyl, 7-octyl-2-anthranyl, 8-octyl-2-anthranyl, 9-octyl-2-anthranyl, 10-octyl-2-anthranyl, 1-octyl-9-anthranyl, 2-octyl-9-anthranyl, 3-octyl-9-anthranyl, 4-octyl-9-anthranyl, 10-octyl-9-anthranyl, 2-phenyl-1-anthranyl, 3-phenyl-1-anthranyl, 4-phenyl-1-anthranyl, 5-phenyl-1-anthranyl, 6-phenyl-1-anthranyl, 7-phenyl-1-anthranyl, 8-phenyl-1-anthranyl, 9-phenyl-1-anthranyl, 10-phenyl-1-anthranyl, 1-phenyl-2-anthranyl, 3-phenyl-2-anthranyl, 4-phenyl-2-anthranyl, 5-phenyl-2-anthranyl, 6-phenyl-2-anthranyl, 7-phenyl-2-anthranyl, 8-phenyl-2-anthranyl, 9-phenyl-2-anthranyl, 10-phenyl-2-anthranyl, 1-phenyl-9-anthranyl, 2-phenyl-9-anthranyl, 3-phenyl-9-anthranyl, 4-phenyl-9-anthranyl, 10-phenyl-9-anthranyl, 2-methoxy-1-anthranyl, 3-methoxy-1-anthranyl, 4-methoxy-1-anthranyl, 5-methoxy-1-anthranyl, 6-methoxy-1-anthranyl, 7-methoxy-1-anthranyl, 8-methoxy-1-anthranyl, 9-ethoxy-1-anthranyl, 1-methoxy-1-anthranyl, 1-methoxy-2-anthranyl, 3-methoxy-2-anthranyl, 4-methoxy-2-anthranyl, 5-methoxy-2-anthranyl, 6-methoxy-2-anthranyl, 7-methoxy-2-anthranyl, 8-methoxy-2-anthranyl, 9-methoxy-2-anthranyl, 10-methoxy-2-anthranyl, 1-methoxy-9-anthranyl, 2-methoxy-9-anthranyl, 3-methoxy-9-anthranyl, 4-methoxy-9-anthranyl, 10-methoxy-9-anthranyl, 2-ethoxy-1-anthranyl, 3-ethoxy-1-anthranyl, 4-ethoxy-1-anthranyl, 5-ethoxy-1-anthranyl, 6-ethoxy-1-anthranyl, 7-ethoxy-1-anthranyl, 8-ethoxy-1-anthranyl, 9-ethoxy-1-anthranyl, 10-ethoxy-1-anthranyl, 1-ethoxy-2-anthranyl, 3-ethoxy-2-anthranyl, 4-ethoxy-2-anthranyl, 5-ethoxy-2-anthranyl, 6-ethoxy-2-anthranyl, 7-ethoxy-2-anthranyl, 8-ethoxy-2-anthranyl, 9-ethoxy-2-anthranyl, 10-ethoxy-2-anthranyl, 1-ethoxy-9-anthranyl, 2-ethoxy-9-anthranyl, 3-ethoxy-9-anthranyl, 4-ethoxy-9-anthranyl, 10-ethoxy-9-anthranyl, 2-butoxyl-1-anthranyl, 3-butoxyl-1-anthranyl, 4-butoxyl-1-anthranyl, 5-butoxyl-1-anthranyl, 6-butoxyl-1-anthranyl, 7-butoxyl-1-anthranyl, 8-butoxyl-1-anthranyl, 9-butoxyl-1-anthranyl, 10-butoxyl-1-anthranyl, 1-butoxy-2-anthranyl, 3-butoxy-2-anthranyl, 4-butoxy-2-anthranyl, 5-butoxy-2-anthranyl, 6-butoxy-2-anthranyl, 7-butoxy-2-anthranyl, 8-butoxy-2-anthranyl, 9-butoxy-2-anthranyl, 10-butoxy-2-anthranyl, 1-butoxy-9-anthranyl, 2-butoxy-9-anthranyl, 3-butoxy-9-anthranyl, 4-butoxy-9-anthranyl, 10-butoxy-9-anthranyl, 2-amino-1-anthranyl, 3-amino-1-anthranyl, 4-amino-1-anthranyl, 5-amino-1-anthranyl, 6-amino-1-anthranyl, 7-amino-1-anthranyl, 8-amino-1-anthranyl, 9-amino-1-anthranyl, 10-amino-1-anthranyl, 1-amino-2-anthranyl, 3-amino-2-anthranyl, 4-amino-2-anthranyl, 5-amino-2-anthranyl, 6-amino-2-anthranyl, 7-amino-2-anthranyl, 8-amino-2-anthranyl, 9-amino-2-anthranyl, 10-amino-2-anthranyl, 1-amino-9-anthranyl, 2-amino-9-anthranyl, 3-amino-9-anthranyl, 4-amino-9-anthranyl, 10-amino-9-anthranyl, 2-(N,N-dimethylamino)-1-anthranyl, 3-(N,N-dimethylamino)-1-anthranyl, 4-(N,N-dimethylamino)-1-anthranyl, 5-(N,N-dimethylamino)-1-anthranyl, 6-(N,N-dimethylamino)-1-anthranyl, 7-(N,N-dimethylamino)-1-anthranyl, 8-(N,N-dimethylamino)-1-anthranyl, 9-(N,N-dimethylamino)-1-anthranyl, 10-(N,N-dimethylamino)-1-anthranyl, 1-(N,N-dimethylamino)-2-anthranyl, 3-(N,N-dimethylamino)-2-anthranyl, 4-(N,N-dimethylamino)-2-anthranyl, 5-(N,N-dimethylamino)-2-anthranyl, 6-(N,N-dimethylamino)-2-anthranyl, 7-(N,N-dimethylamino)-2-anthranyl, 8-(N,N-dimethylamino)-2-anthranyl, 9-(N,N-dimethylamino)-2-anthranyl, 10-(N,N-dimethylamino)-2-anthranyl, 1-(N,N-dimethylamino)-9-anthranyl, 2-(N,N-dimethylamino)-9-anthranyl, 3-(N,N-dimethylamino)-9-anthranyl, 4-(N,N-dimethylamino)-9-anthranyl, 10-(N,N-dimethylamino)-9-anthranyl, 2-(N,N-diphenylamino)-1-anthranyl, 3-(N,N-diphenylamino)-1'-anthranyl, 4-(N,N-diphenylamino)-1-anthranyl, 5-(N,N-diphenylamino)-1-anthranyl, 6-(N,N-diphenylamino)-1-anthranyl, 7-(N,N-diphenylamino)-1-anthranyl, 8-(N,N-diphenylamino)-1-anthranyl, 9-(N,N-diphenylamino)-1-anthranyl, 10-(N,N-diphenylamino)-1-anthranyl, 1-(N,N-diphenylamino)-2-anthranyl, 3-(N,N-diphenylamino)-2-anthranyl, 4-(N,N-diphenylamino)-2-anthranyl, 5-(N,N-diphenylamino)-2-anthranyl, 6-(N,N-diphenylamino)-2-anthranyl, 7-(N,N-diphenylamino)-2-anthranyl, 8-(N,N-diphenylamino)-2-anthranyl, 9-(N,N-diphenylamino)-2-anthranyl, 10-(N,N-diphenylamino)-2-anthranyl, 1-(N,N-diphenylamino)-9-anthranyl, 2-(N,N-diphenylamino)-9-anthranyl, 3-(N,N-diphenylamino)-9-anthranyl, 4-(N,N-diphenylamino)-9-anthranyl, and 10-(N,N-diphenylamino)-9-anthranyl.

Among these substituents, preferred as $R^1$ and $R^2$ are a hydrogen atom, halogen atoms such as bromine atom and iodine atom, trialkylstannyl groups such as tributylstannyl $(Sn(Bu-n)_3)$, trialkylsilyl groups such as trimethylsilyl $(SiMe_3)$, and dialkoxyboryl groups such as $B(OMe)_2$.

Further, taking into consideration the heightening of the electroconductivity of the sulfonylthiophene compounds, preferred as $R^1$ and $R^2$ are a phenyl group which may be substituted by W, a naphthyl group which may be substituted by W, and an anthranyl group which may be substituted by W.

In this case, preferred as W is a diphenylamino group which may be substituted by W', a dinaphthylamino group which may be substituted by W', a dianthranylamino group which may be substituted by W', an N-phenyl-N-naphthylamino group which may be substituted by W', an N-phenyl-N-anthranyl group which may be substituted by W', and an N-naphthyl-N-anthranylamino group which may be substituted by W'.

In the formula [1], $R^3$ and $R^{3'}$ each independently represent an alkyl group having 1 to 20 carbon atoms, haloalkyl group having 1 to 20 carbon atoms, phenyl group which may be substituted by W, or thienyl group which may be substituted by W, or $R^3$ and $R^{3'}$ are fused together to represent an alkylene group which has 1 to 3 carbon atoms and may be substituted by W, phenylene group which may be substituted by W, or $-(CH_2)q-SO_2-(CH_2)q-SO_2-(CH_2)q$ in which q stands for an integer of from 1 to 3. Ws have the same meaning as defined above.

Illustrative of the thienyl group which may be substituted by W are thienyl, ethylenedioxythienyl, butylthienyl, hexylthienyl, octylthienyl, and decylthienyl.

Illustrative of the alkylene group, which has 1 to 3 carbon atoms and may be substituted by W, are methylene, ethylene, trimethylene, difluoromethylene, tetrafluoroethylene, and hexafluorotrimethylene.

Illustrative of the phenylene group which may be substituted by W are phenylene and perfluorophenylene.

It is to be noted that specific examples of the alkyl group having 1 to 20 carbon atoms, haloalkyl group having 1 to 20 carbon atoms and phenyl group which may be substituted by W are as mentioned above.

Among these, preferred as $R^3$ and $R^{3'}$ are alkyl groups having 1 to 20 carbon atoms, haloalkyl groups having 1 to 20 carbon atoms, and a phenyl group.

Specific examples of the compound represented by the formula [1] include, but are not limited to, the following compounds:

[Chemical Formula 32]

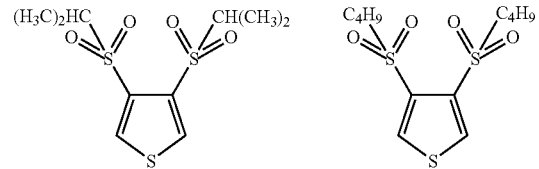

-continued
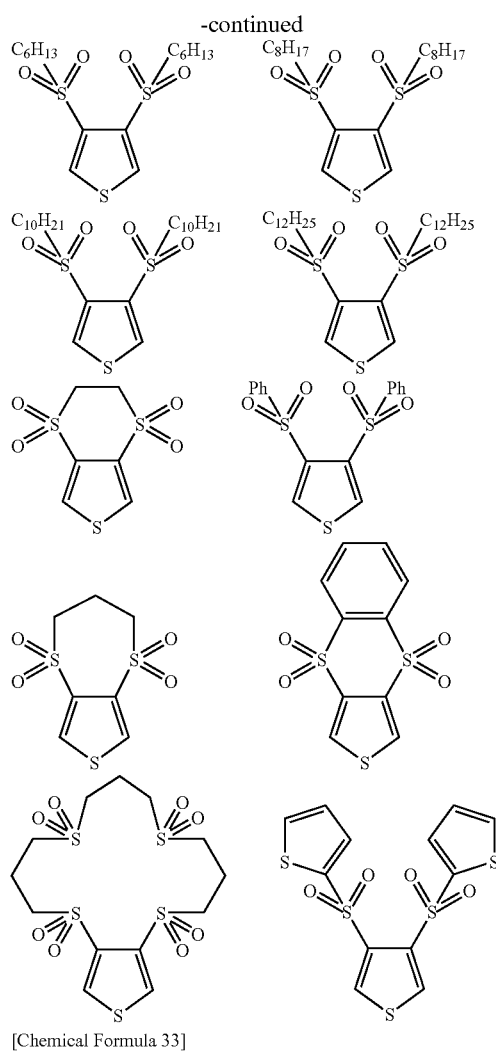
[Chemical Formula 33]
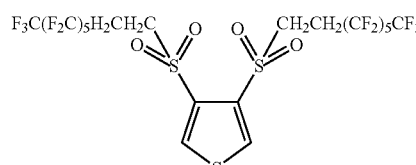
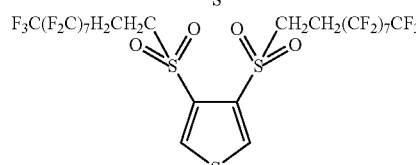
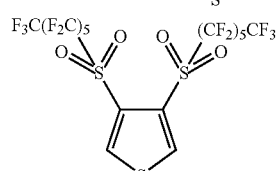
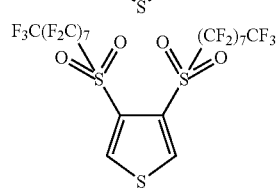
-continued
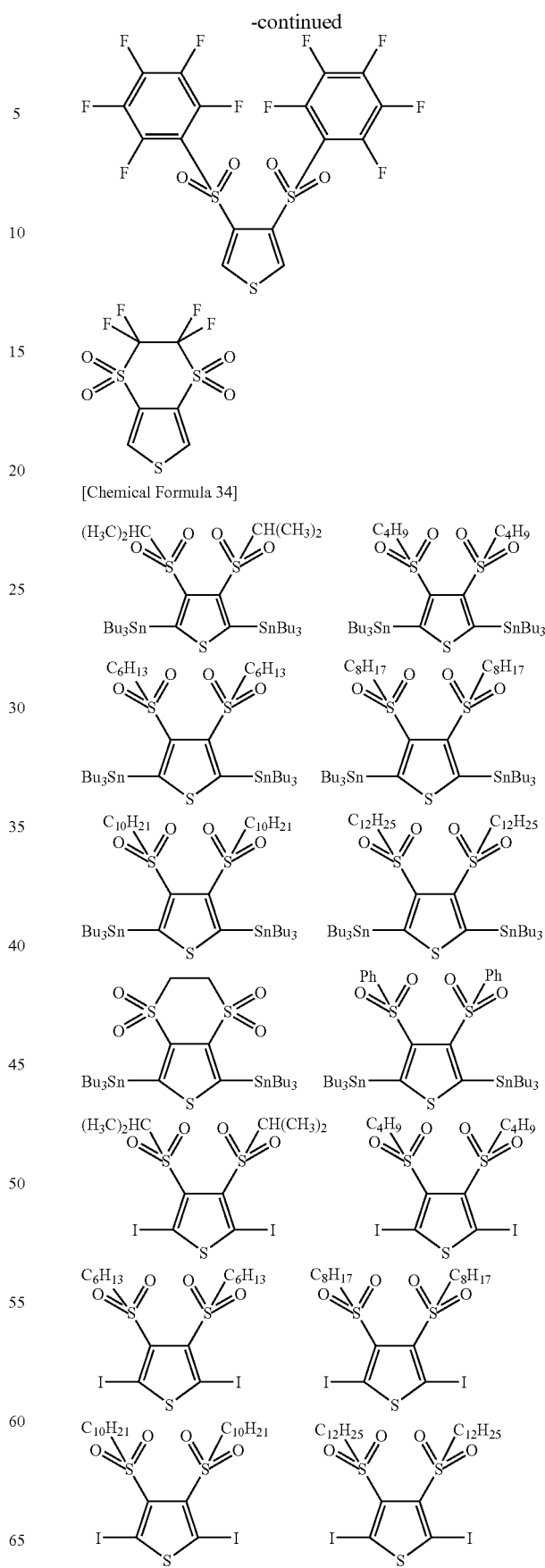
[Chemical Formula 34]

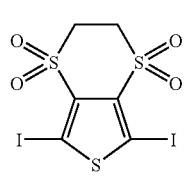
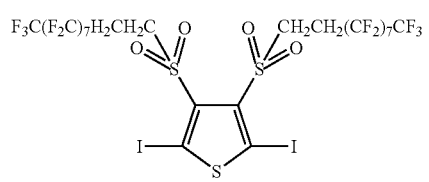
[Chemical Formula 35]
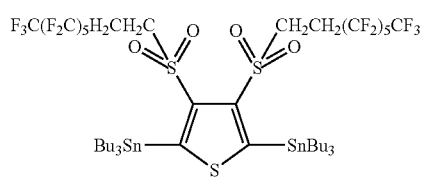
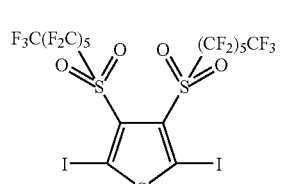
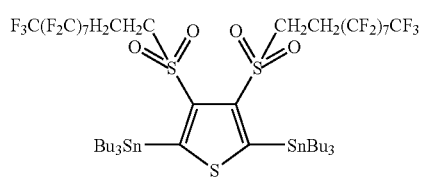
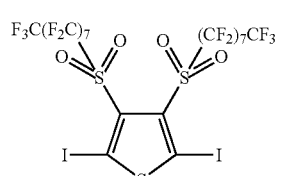
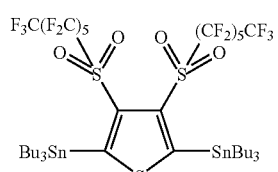
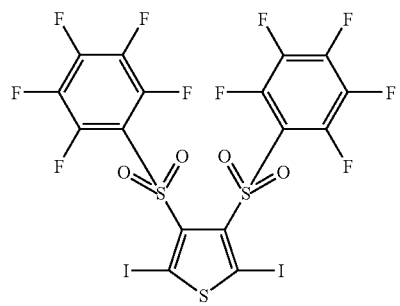
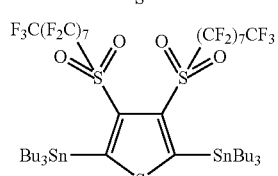
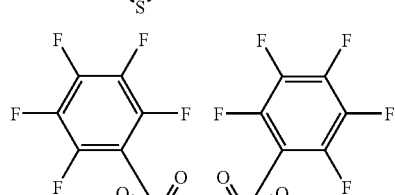
[Chemical Formula 37]
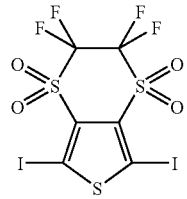
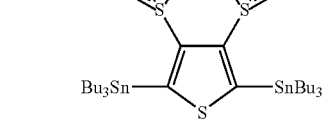
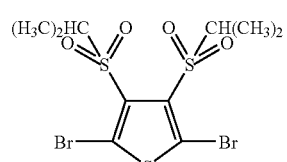
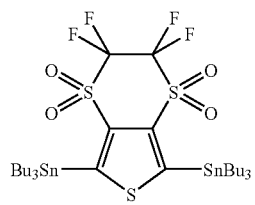
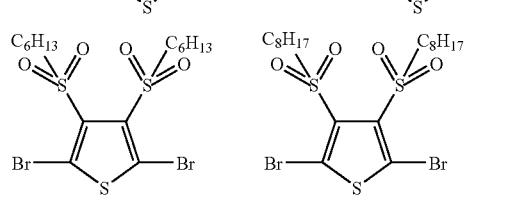
[Chemical Formula 36]
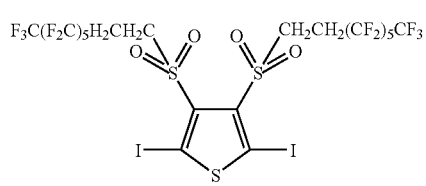
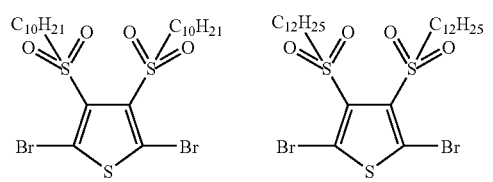

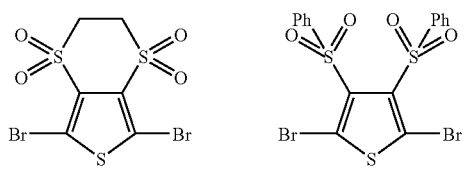
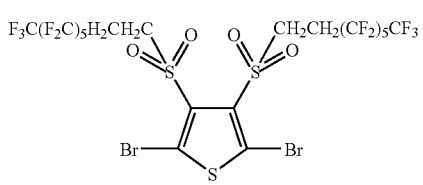
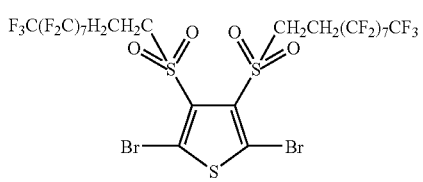
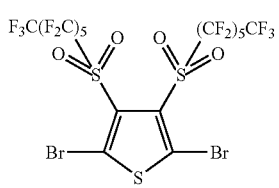
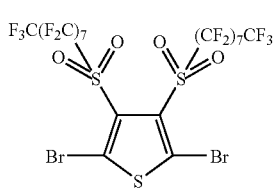
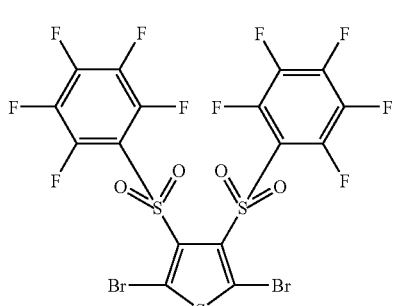
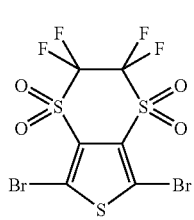
[Chemical Formula 38]
[Chemical Formula 39]
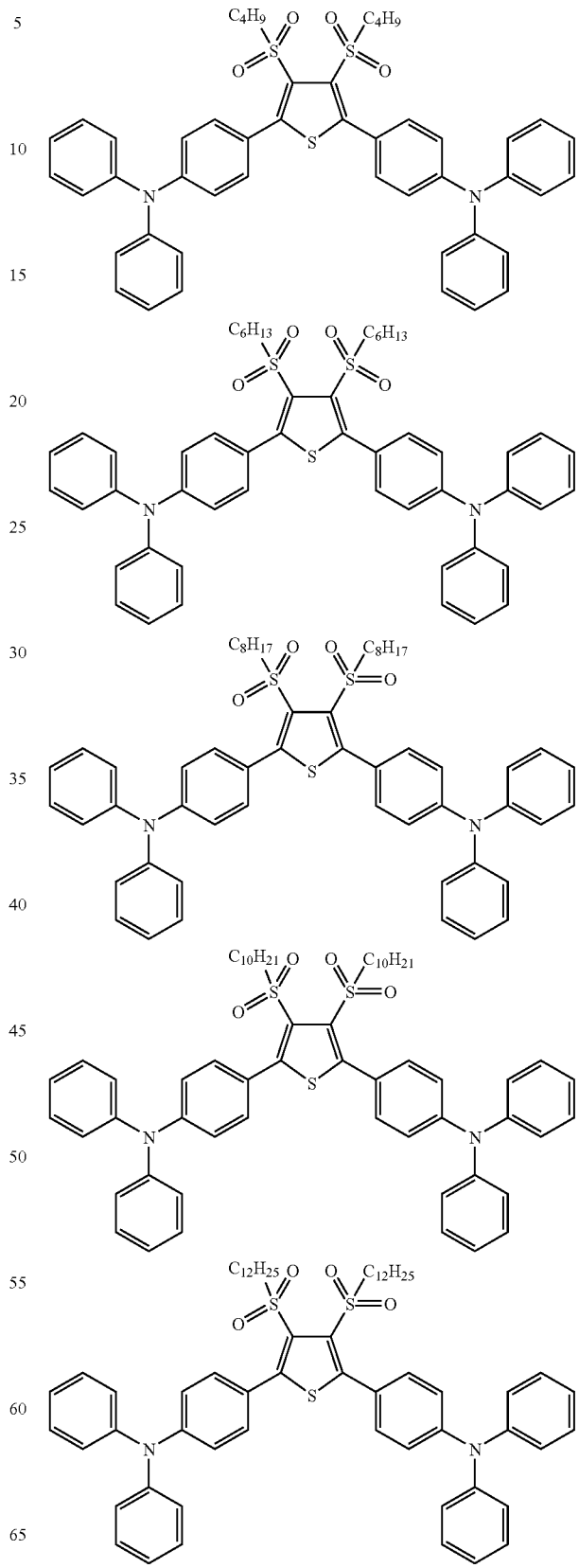

31
-continued
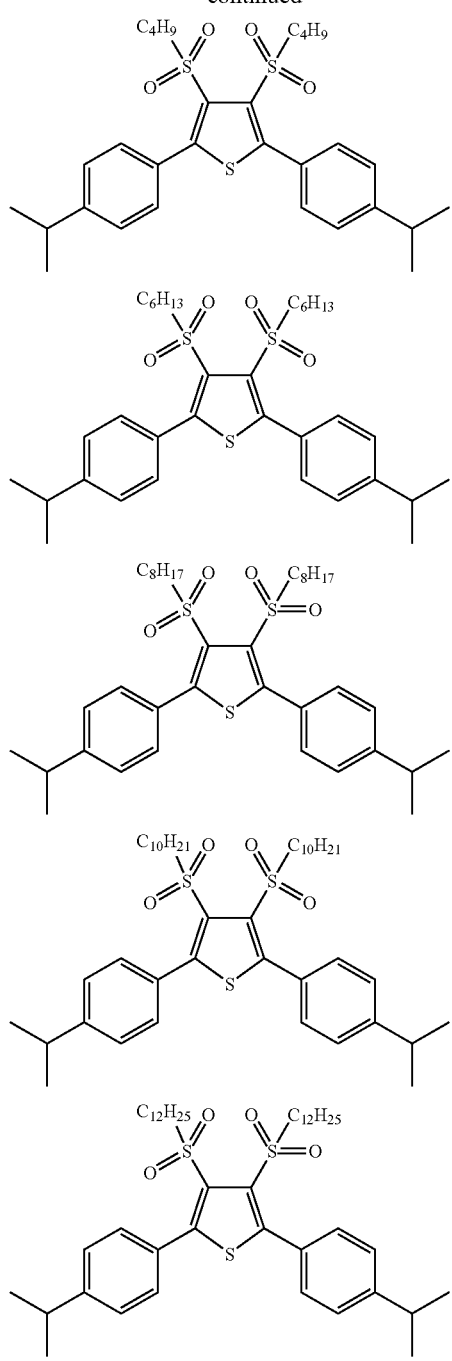
[Chemical Formula 40]
32
-continued
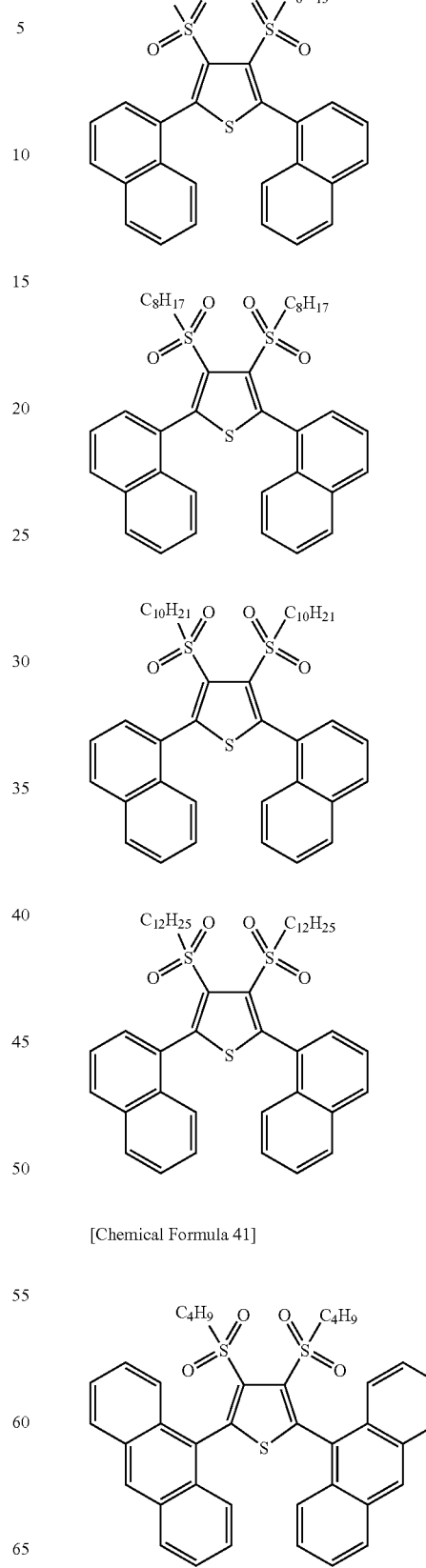
[Chemical Formula 41]

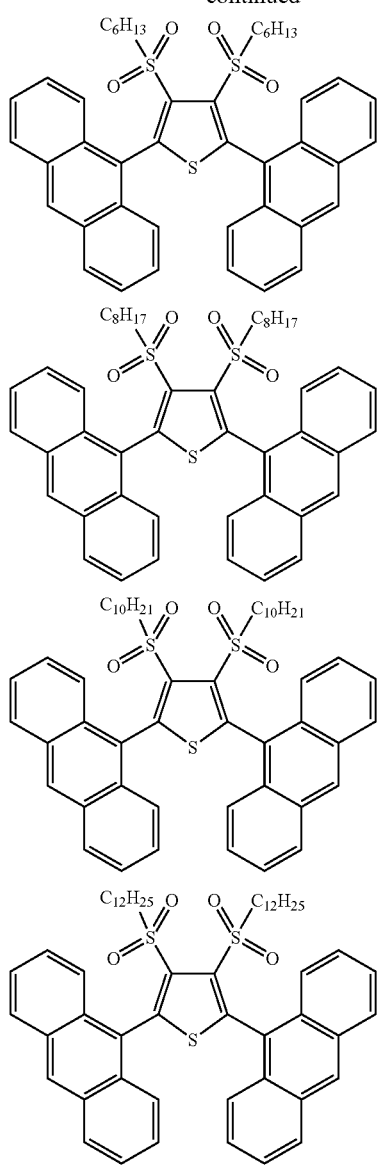
Specific examples of the compound represented by the formula [24] include, but are not limited to, the following compounds:
[Chemical Formula 42]
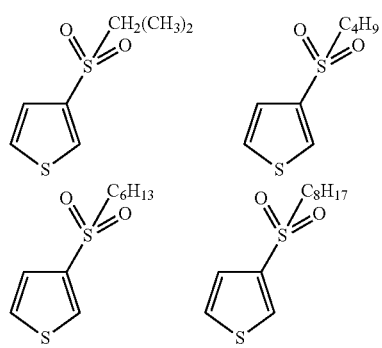
[Chemical Formula 43]
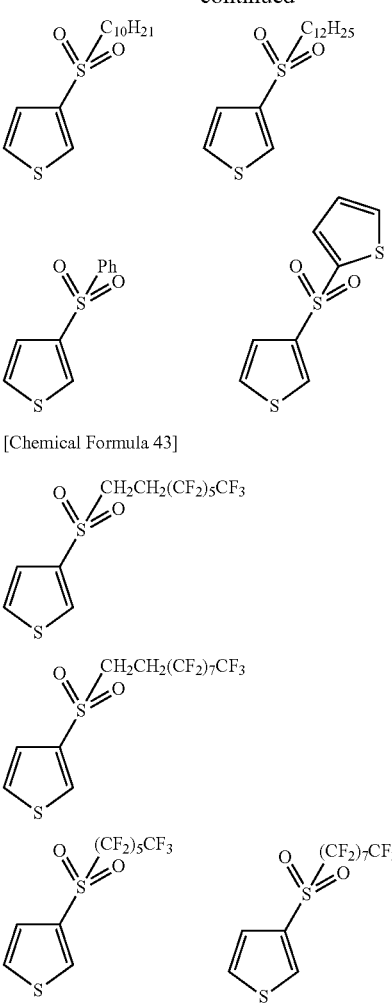
[Chemical Formula 44]
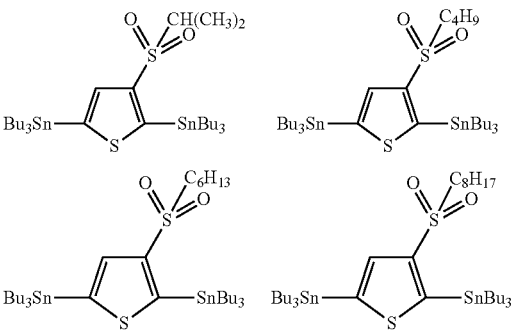

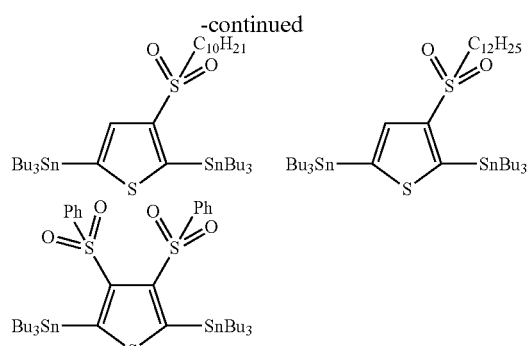
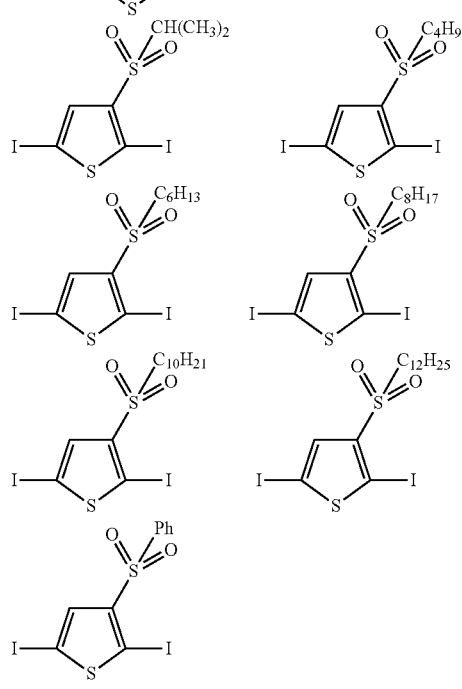
[Chemical Formula 45]
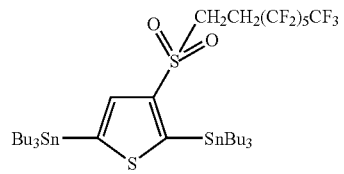
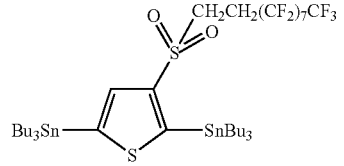
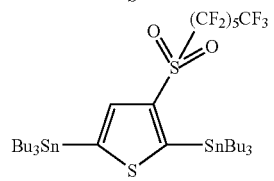
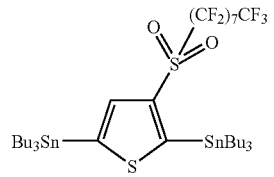
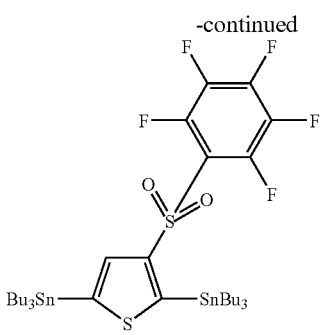
[Chemical Formula 46]
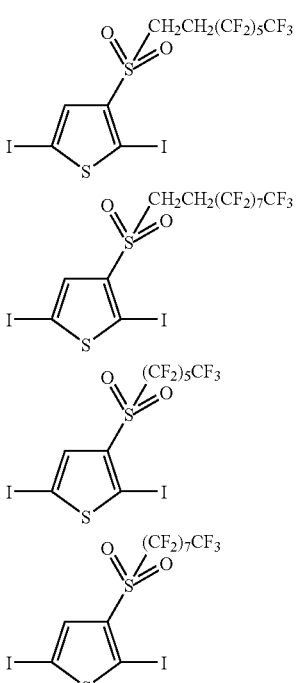
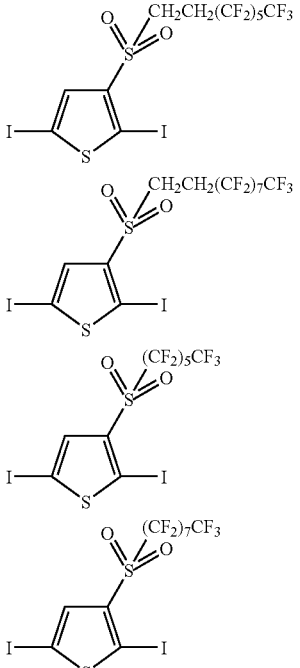
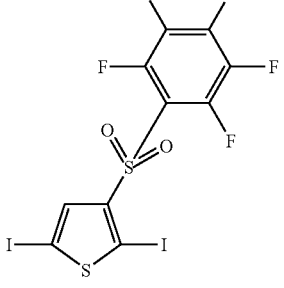
[Chemical Formula 47]
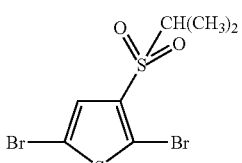
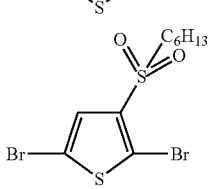
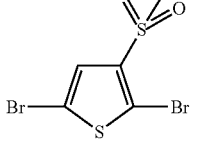

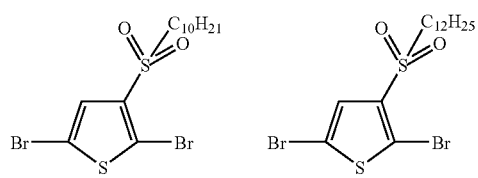
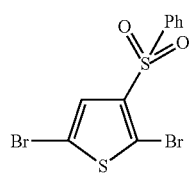
[Chemical Formula 48]
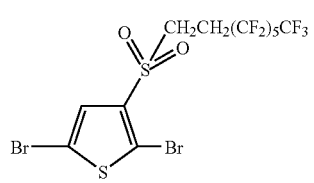
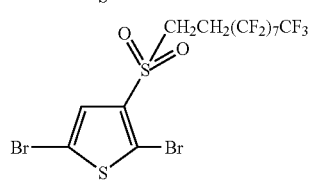
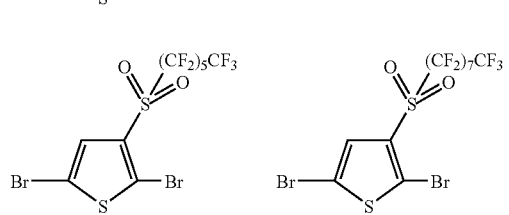
[Chemical Formula 49]
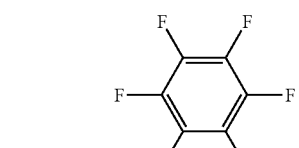
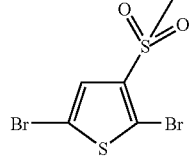
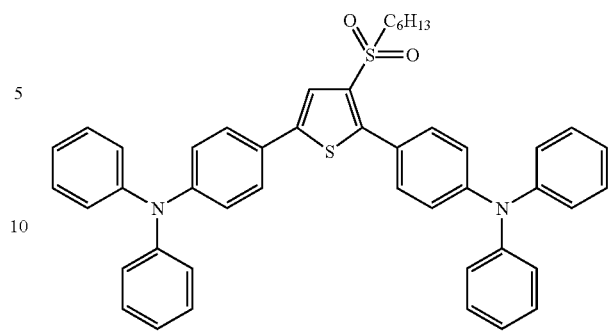
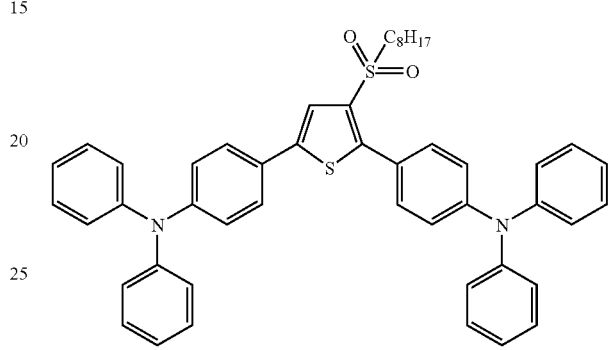
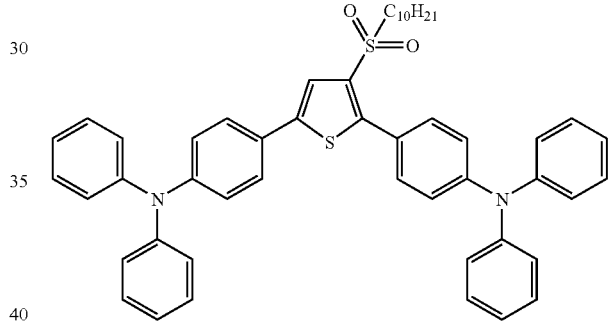
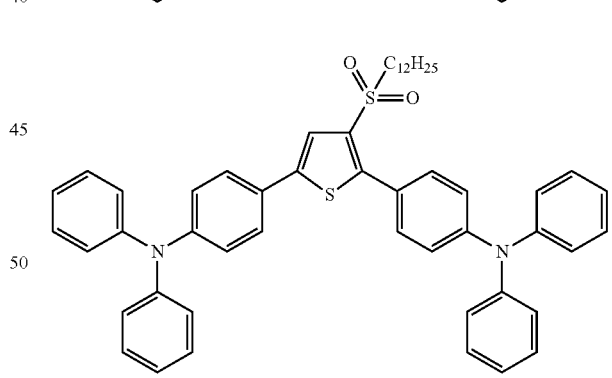
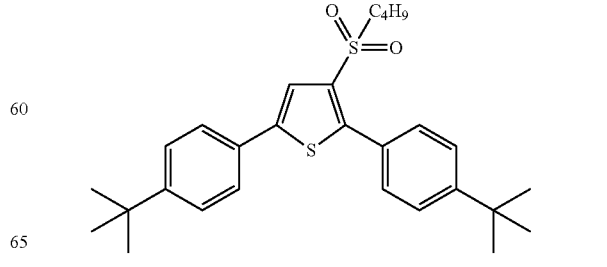

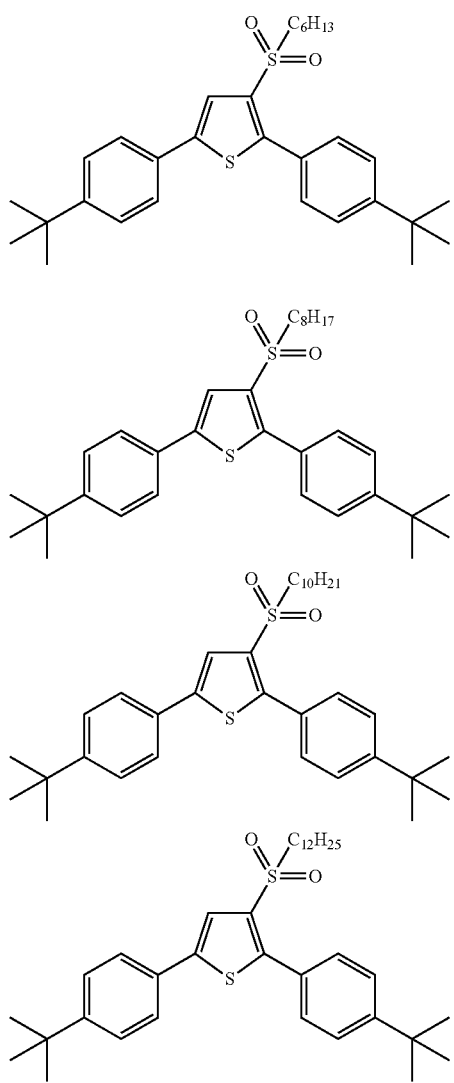
[Chemical Formula 50]
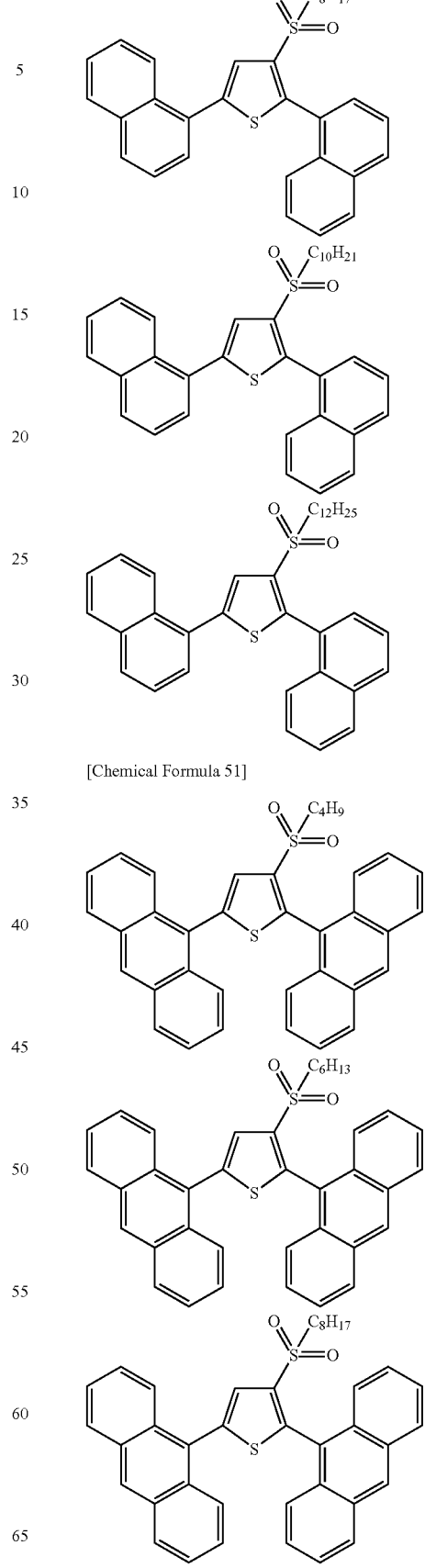
[Chemical Formula 51]

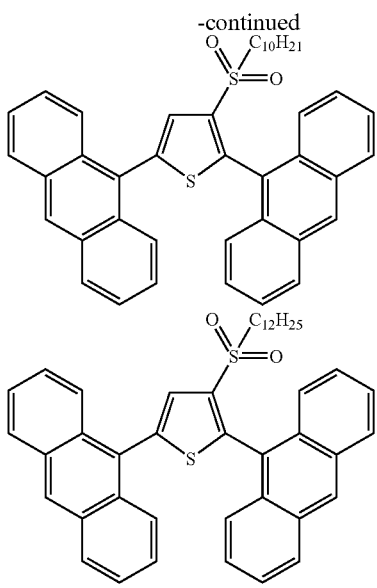

The sulfonylthiophene oligomer compounds according to the invention are represented by the formulas [2] and [16], respectively, and the sulfonylthiophene polymer compounds according to the invention are represented by the formulas [25] and [26], respectively.

In the sulfonylthiophene oligomer and polymer compounds represented by the respective formulas, $R^3$ and $R^{3'}$ are as mentioned above with respect to the formula [1]. In this case, preferred are also alkyl groups having 1 to 20 carbon atoms, haloalkyl groups having 1 to 20 carbon atoms and a phenyl group as in the above-described case.

$R^5$ and $R^6$ each independently represent an alkyl group having 1 to 20 carbon atoms, haloalkyl group having 1 to 20 carbon atoms, phenyl group which may be substituted by W, or thienyl group which may be substituted by W. It is to be mentioned that W is as mentioned above.

Among these, preferred as $R^5$ and $R^6$ are alkyl groups having 1 to 20 carbon atoms, haloalkyl groups having 1 to 20 carbon atoms, and a phenyl group.

$R^4$ and $R^7$ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, or phenyl group which may be substituted by W. W is as mentioned above.

Among these, preferred as $R^4$ and $R^7$ are a hydrogen atoms and alkyl groups having 1 to 20 carbon atoms, with a hydrogen atom being more preferred.

Z in the formulas [2] and [25] is at least one divalent organic group selected from the above-described formulas [3] to [11], with a divalent organic group represented by the formula [3] being particularly preferred. $R^8$ to $R^{30}$ in the formulas [3] to [11] each independently represent a hydrogen atom, alkyl group having 1 to 20 carbon atoms, haloalkyl group having 1 to 20 carbon atoms, alkoxy group having 1 to 10 carbon atoms, alkylthio group having 1 to 20 carbon atoms, dialkylamino group having 1 to 10 carbon atoms, or phenyl group which may be substituted by W. $R^{31}$ represents a hydrogen atom, alkyl group having 1 to 20 carbon atoms, haloalkyl group having 1 to 20 carbon atoms, alkoxy group having 1 to 10 carbon atoms, or phenyl group which may be substituted by W'. It is to be noted that W and W' are as mentioned above.

Specific examples of the phenyl group which may be substituted by W' include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-methoxyphenyl, m-methoxyphenyl, o-trifluoromethoxyphenyl, p-trifluoromethoxyphenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 2,4,6-trimethylphenyl, 2,4,6-tristrifluoromethylphenyl, 2,4,6-trimethoxyphenyl, and 2,4,6-tristrifluoromethoxyphenyl.

It is to be noted that specific examples of other substituents in $R^{18}$ to $R^{40}$ are as mentioned above.

In the formula [2], m, n and o each independently stand for 0 or an integer of 1 or greater, p stands for 0 or an integer of 1 or greater and m, n, o and p satisfy m+n+o≧1 and 2≦m+n+o+p≦50, particularly preferably 2≦m+n+o+p≦10, with any two of m, n and o being preferably zero.

In the formula [16], m', n' and o' each independently stand for 0 or an integer of 1 or greater, and m', n' and o' satisfy 2≦m'+n'+o'≦50, particularly preferably 2≦m'+n'+o'≦10, with any two of m', n' and o' being preferably zero.

In the formula [25], m", n" and o" each independently stand for 0 or an integer of 1 or greater, p' stands for 0 or an integer of 1 or greater, and m", n", o" and p' satisfy m"+n"+o"≧1 and 50<m"+n"+o"+p'<5,000, with the satisfaction of m"+n"+o"≧10 and 50<m"+n"+o"+p'<500 being particularly preferred.

In the formula [26], m''', n''' and o''' each independently stand for 0 or an integer of 1 or greater, and m''', n''' and o''' satisfy 50<m'''+n'''+o'''<5,000, with the satisfaction of 50<m'''+n'''+o'''<500 being preferred.

$Y^1$ and $Y^2$ in the sulfonylthiophene oligomer and polymer compounds of the respective formulas [2] and [25] each independently represent at least one monovalent organic group selected from the following formulas [12] to [15]:

[Chemical Formula 52]

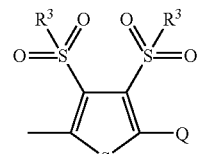
[12]

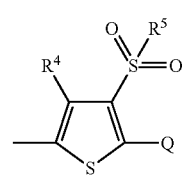
[13]

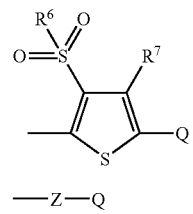
[14]

[15]

In these formulas [12] to [15], $R^3$ to $R^7$ and Z have the same meanings as defined above.

Q is both end groups of the sulfonylthiophene oligomer and polymer compounds, and these both end groups are each independently a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, with a hydrogen atom, bromine atom, iodine atom and tributylstannyl group being preferred. W is as mentioned above. It is to be noted that similar Q applies to the both end groups of the sulfonylthiophene oligomer and polymer compounds of the respective formulas [16] and [26].

The sulfonylbithiophene compounds of the invention are represented by the formulas [19] to [22], respectively. In the formulas [19] to [22], X represents —S— or —S(O)$_2$—. $R^{42}$, $R^{43}$, $R^{44}$ and $R^{45}$ each independently represent an alkyl group having 1 to 20 carbon atoms, haloalkyl group having 1 to 20 carbon atoms, or phenyl group which may be substituted by W, and W has the same meaning as defined above. Among these, preferred as $R^{42}$, $R^{43}$, $R^{44}$ and $R^{45}$ are alkyl groups having 1 to 20 carbon atoms, haloalkyl groups having 1 to 20 carbon atoms, and a phenyl group.

$R^{46}$ and $R^{47}$ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, or phenyl group which may be substituted by W. Specific examples of these substituents are as mentioned above. Among these, preferred as $R^{46}$ and $R^{47}$ are a hydrogen atom and alkyl groups having 1 to 20 carbon atoms, with a hydrogen atom being more preferred.

Specific examples of the thiophene compounds represented by the formulas [2], [16] and [19] to [22], respectively, include, but are not limited to, the following compounds:

[Chemical Formula 53]

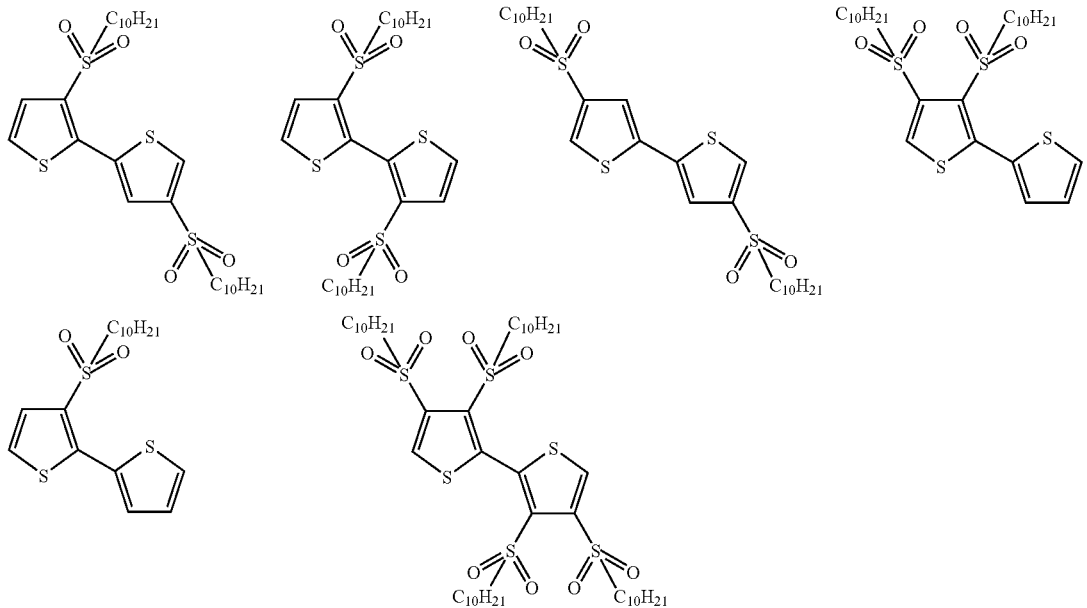

[Chemical Formula 54]

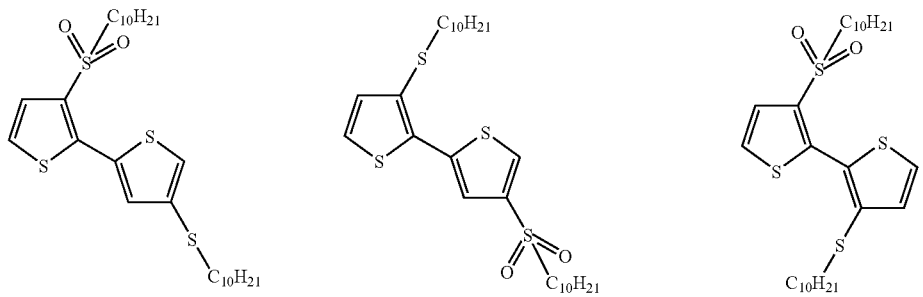

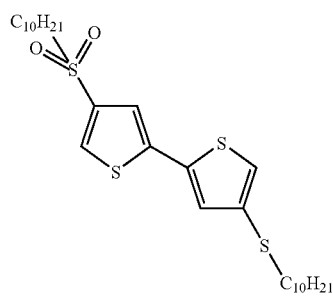
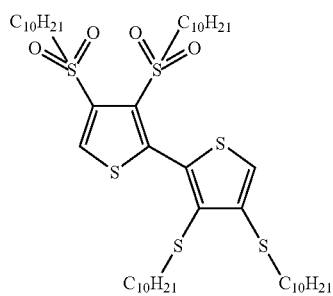
[Chemical Formula 55]
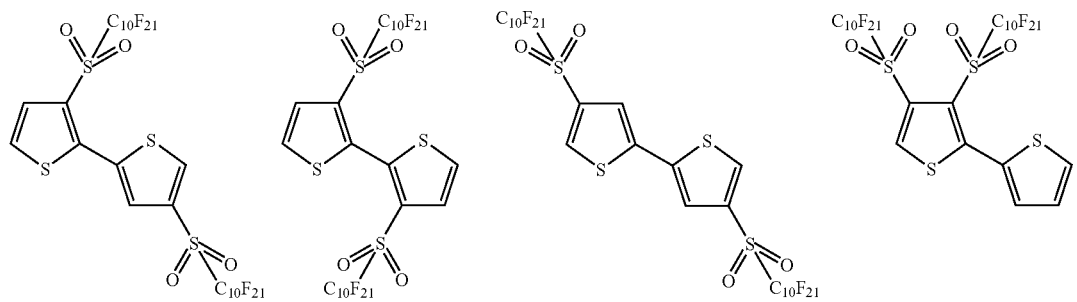
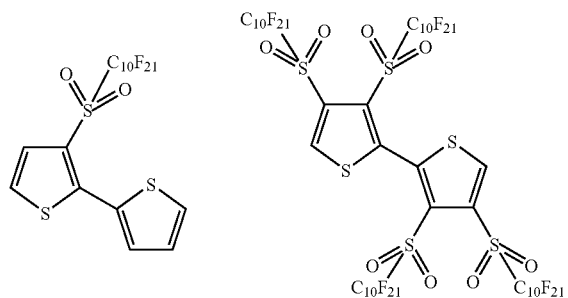
[Chemical Formula 56]
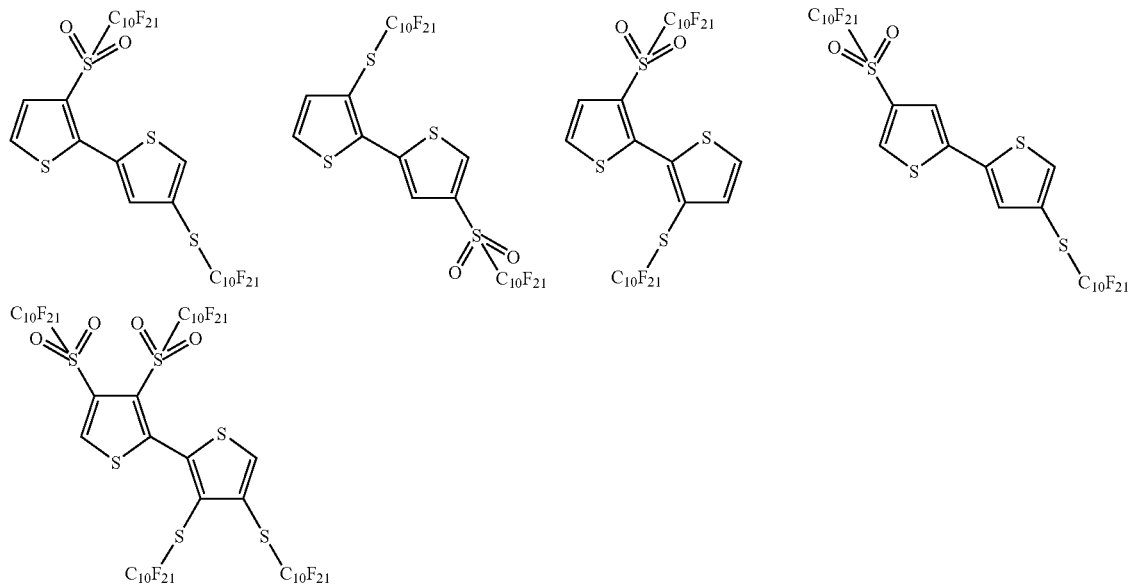

-continued
[Chemical Formula 57]
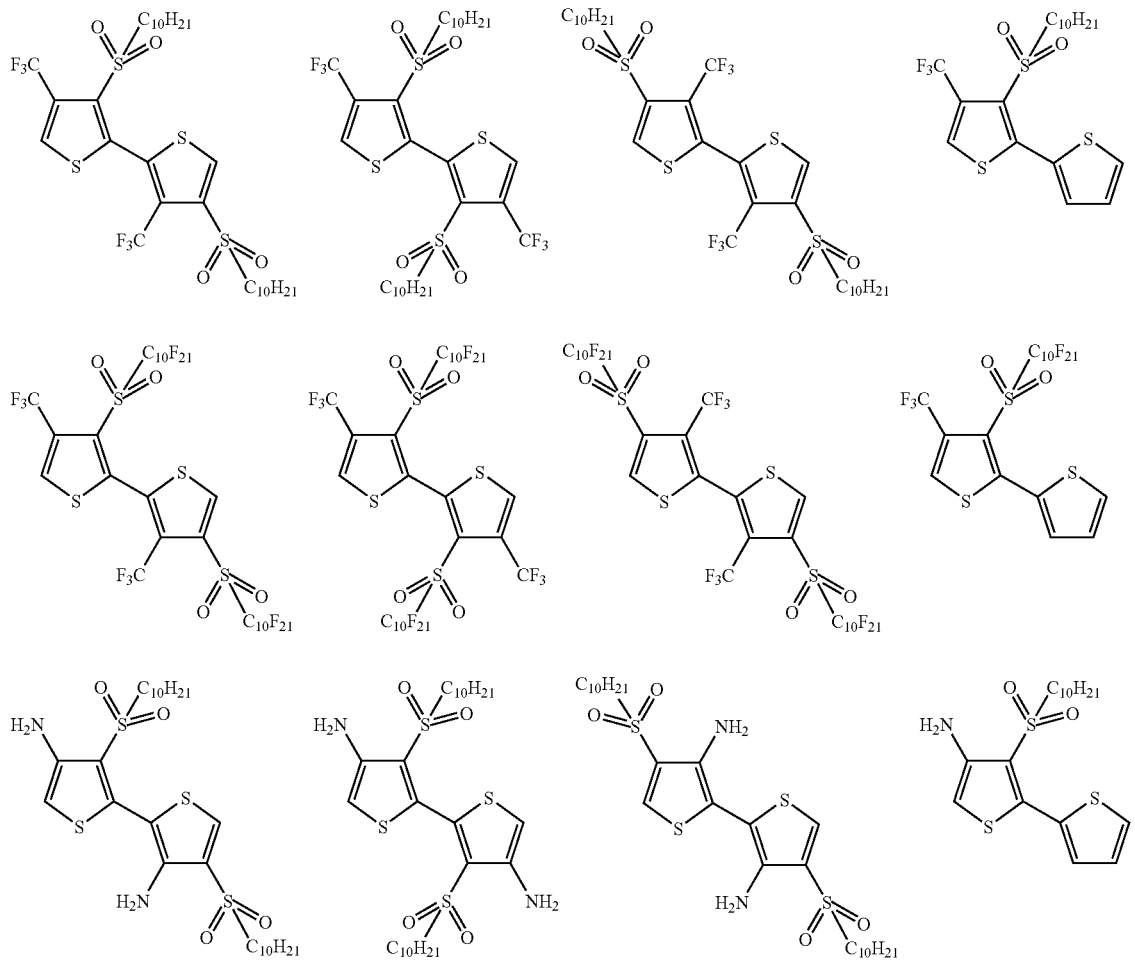
[Chemical Formula 58]
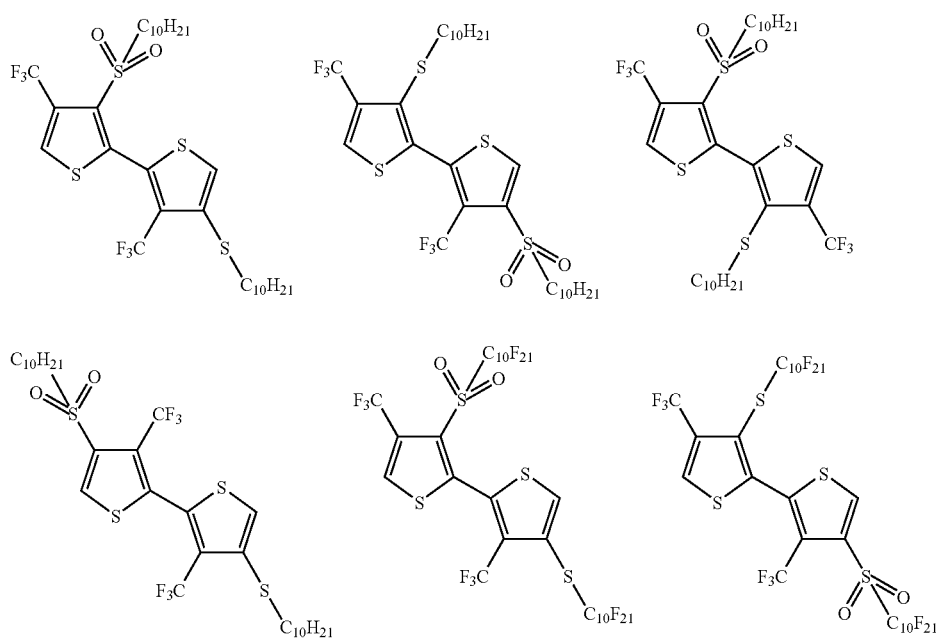

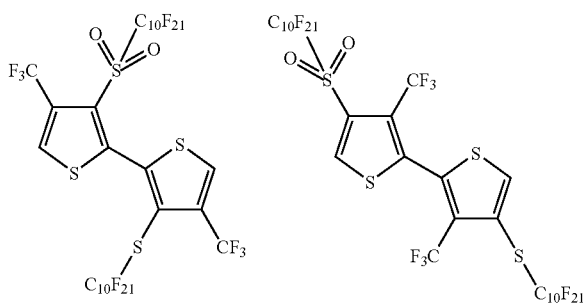
[Chemical Formula 59]
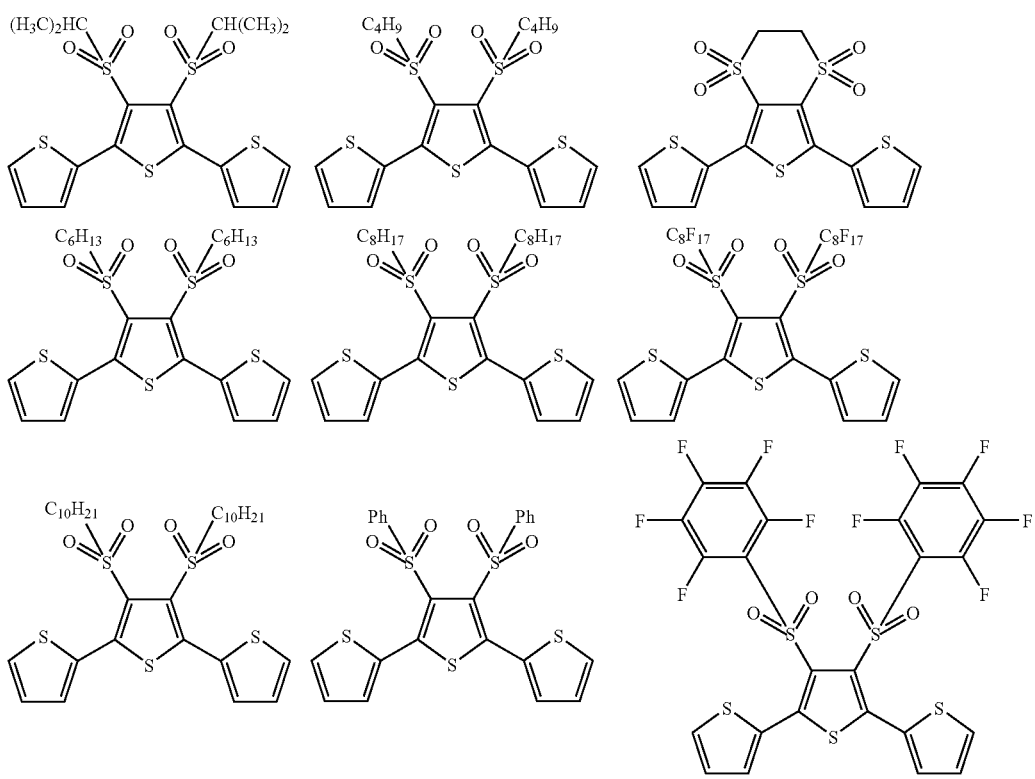
[Chemical Formula 60]
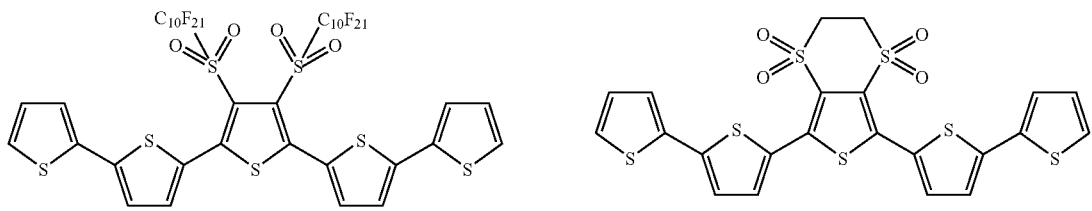
[Chemical Formula 61]
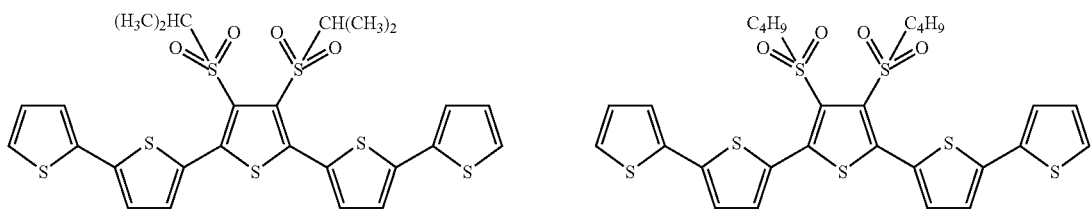

-continued
51
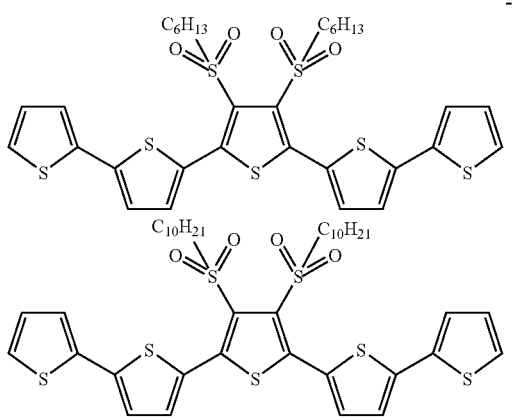
52
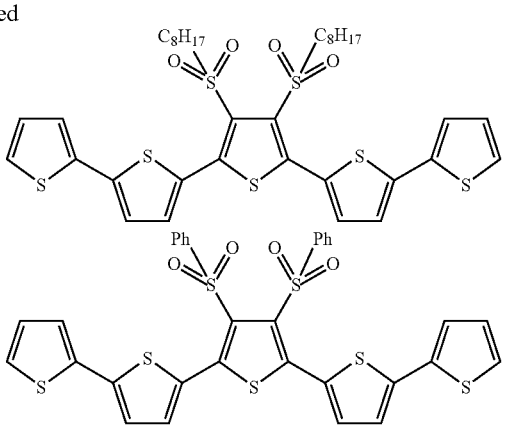
[Chemical Formula 62]
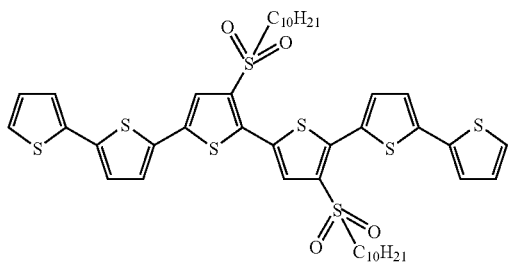
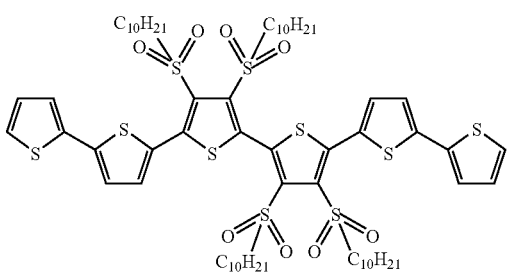
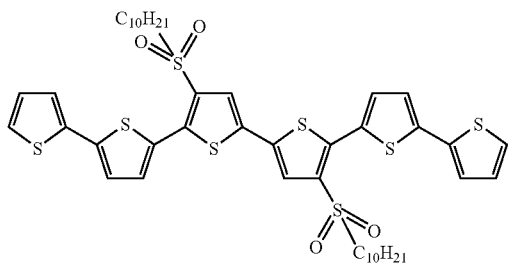
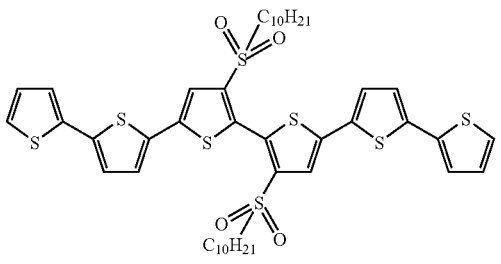
[Chemical Formula 63]
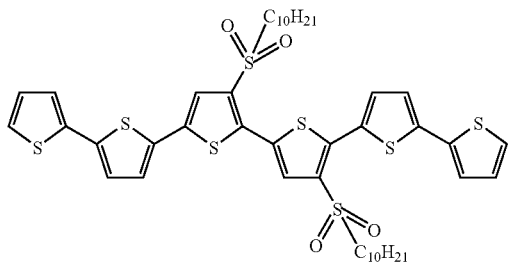
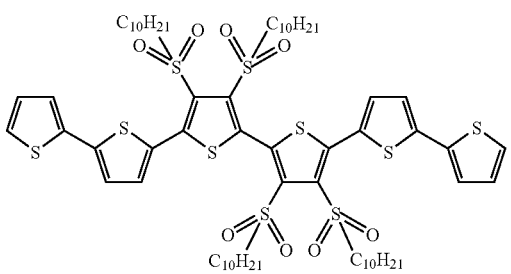
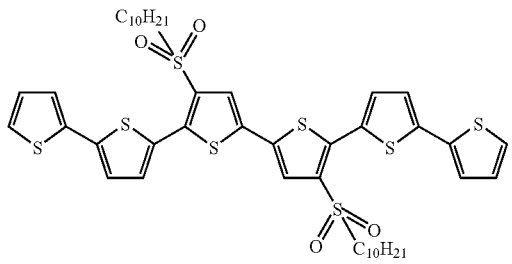
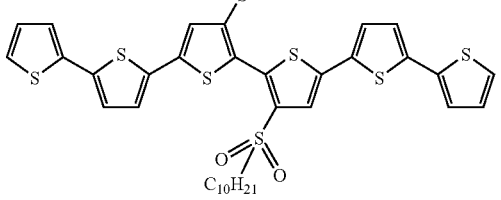

-continued
[Chemical Formula 64]
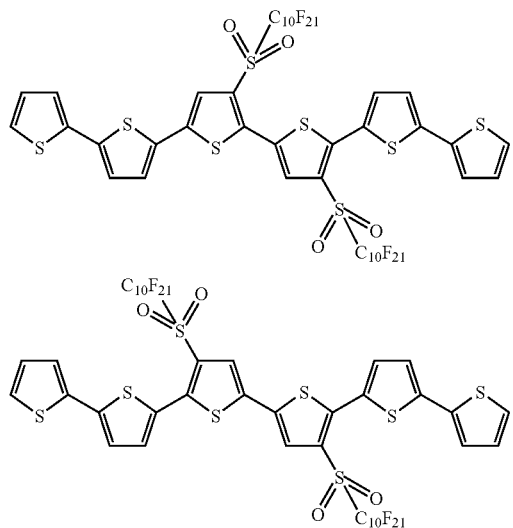
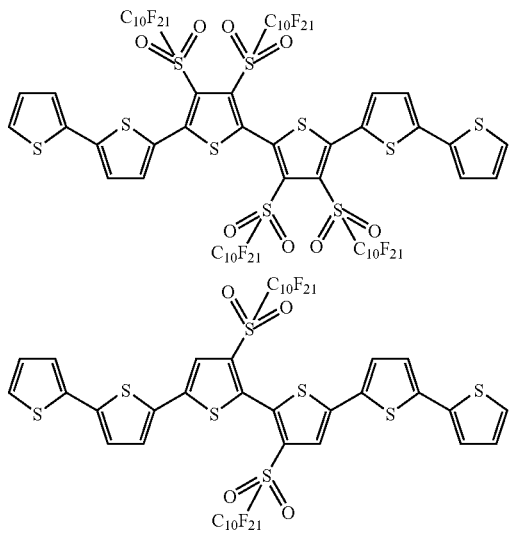
[Chemical Formula 65]
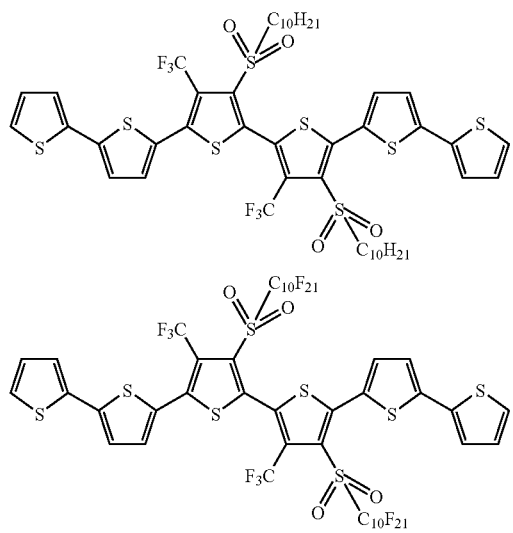
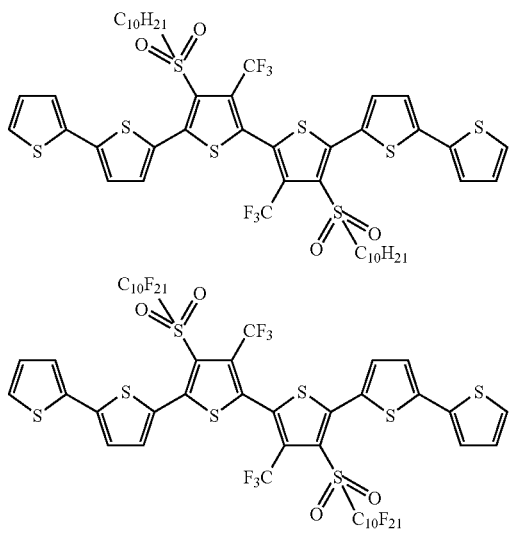
[Chemical Formula 66]
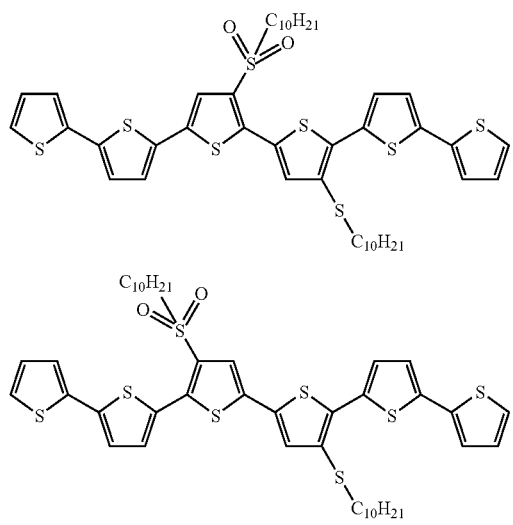
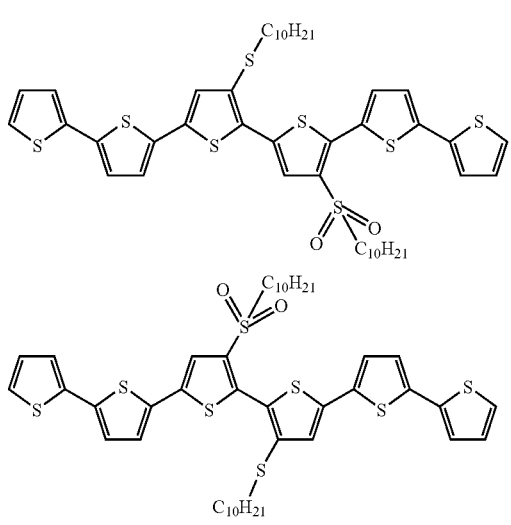

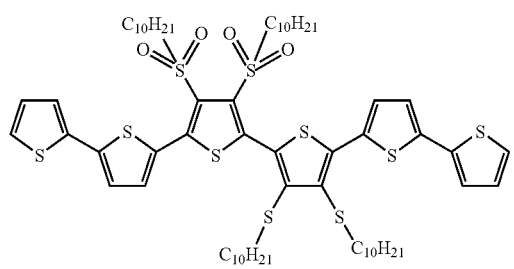
[Chemical Formula 67]
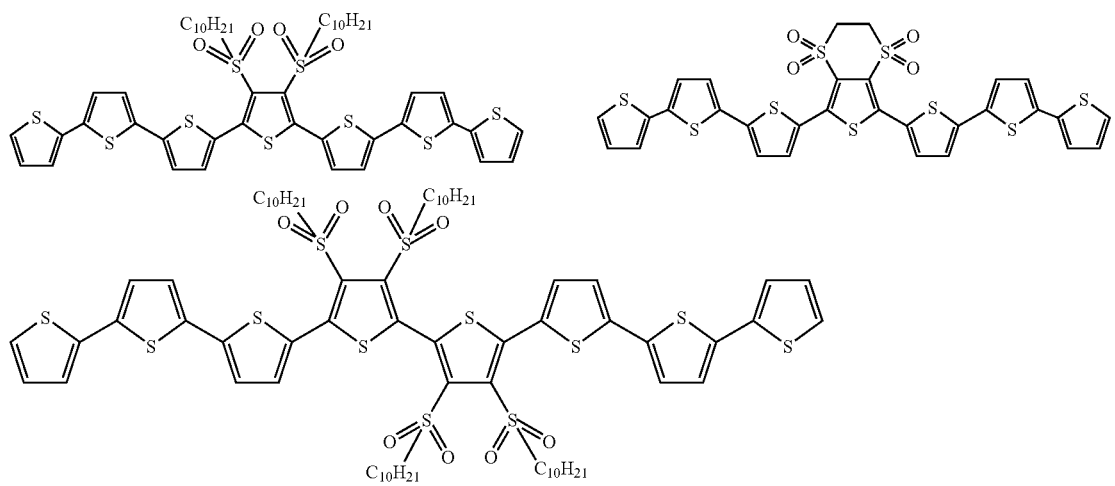
[Chemical Formula 68]
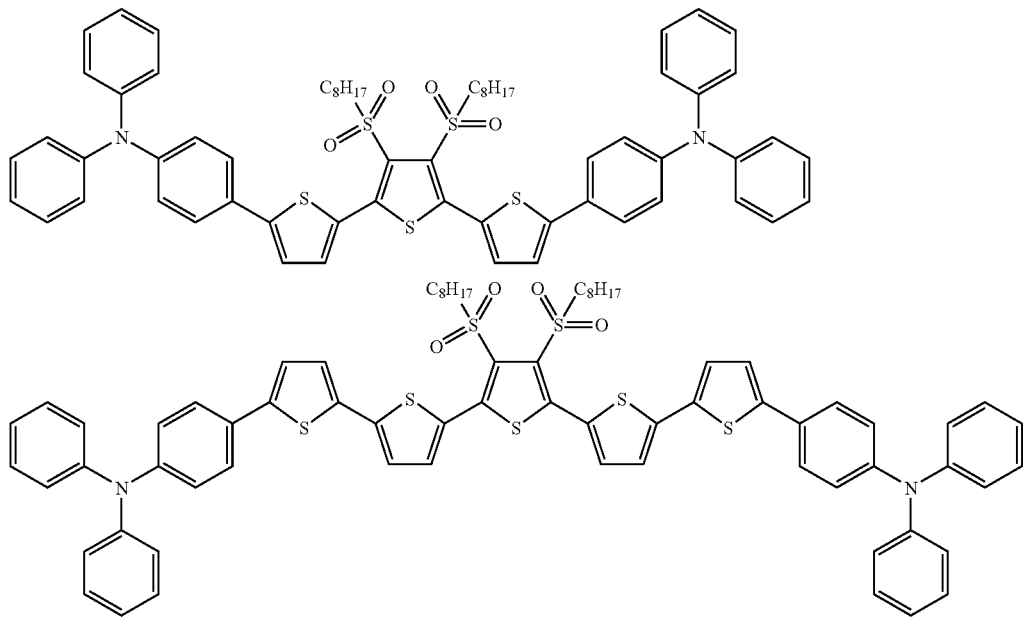
[Chemical Formula 69]
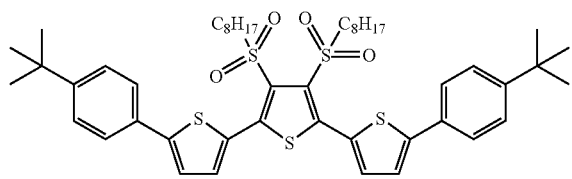

-continued
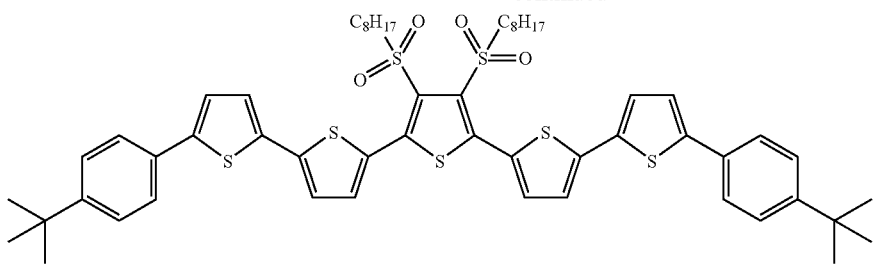
[Chemical Formula 70]
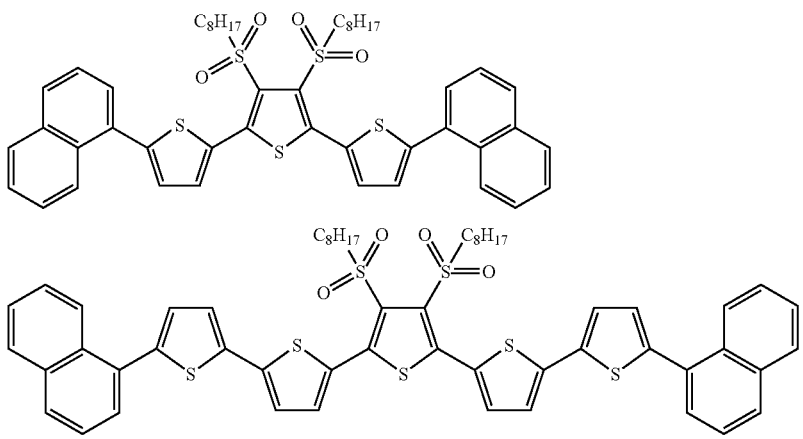
[Chemical Formula 71]
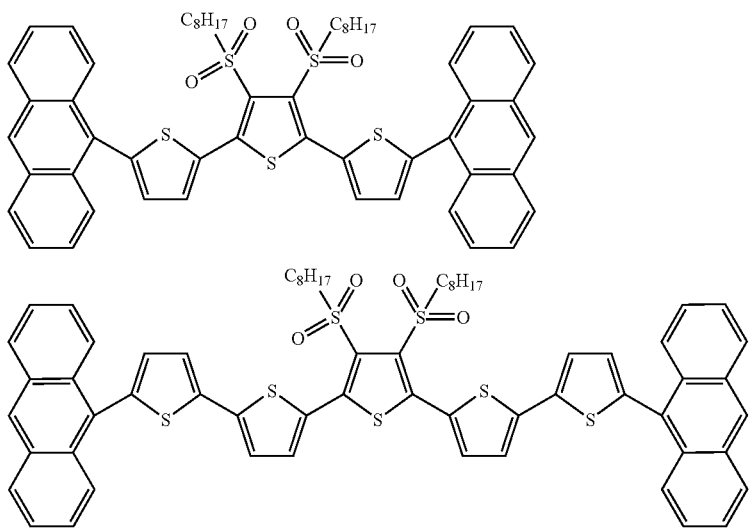
[Chemical Formula 72]
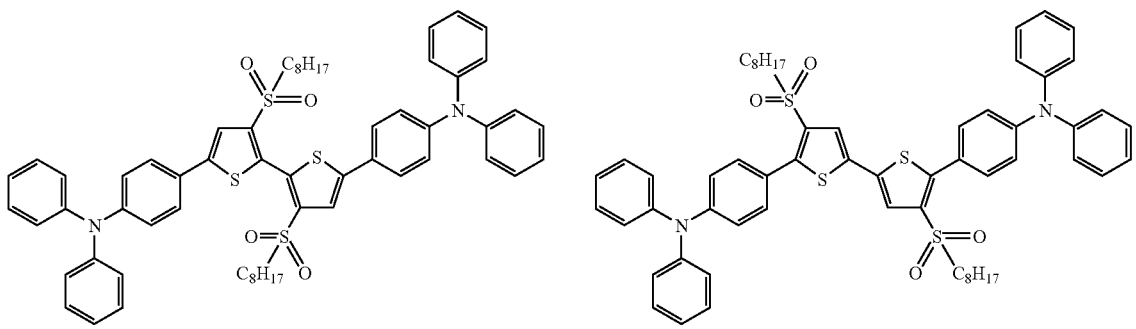

-continued
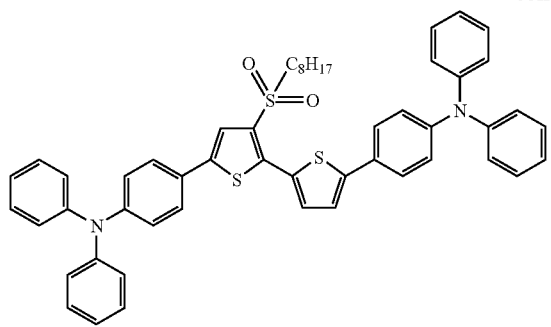
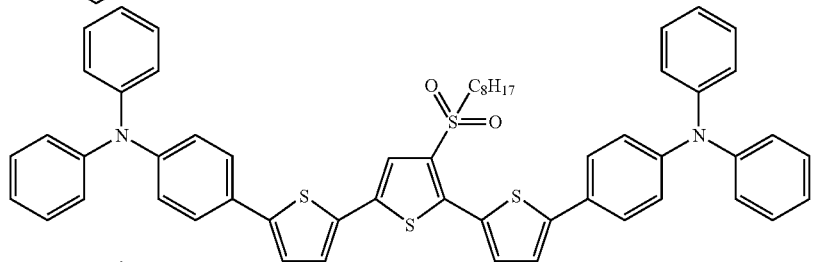
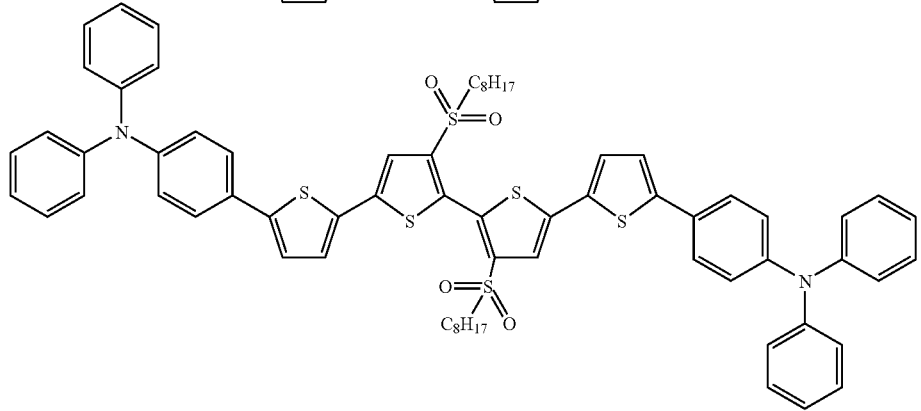
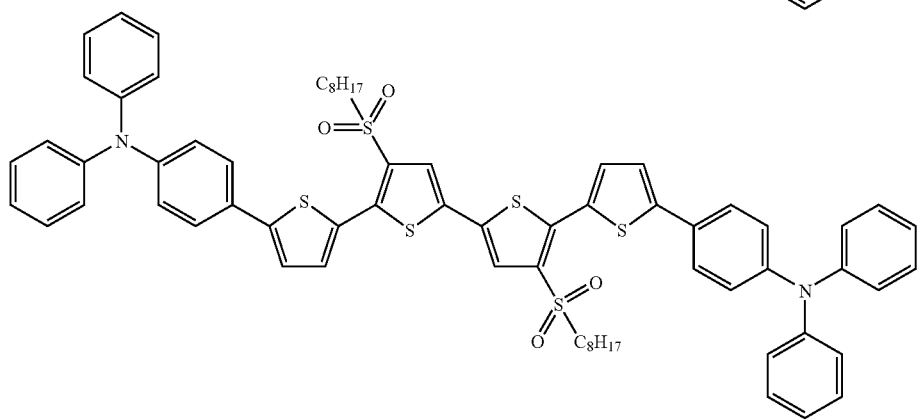
[Chemical Formula 73]
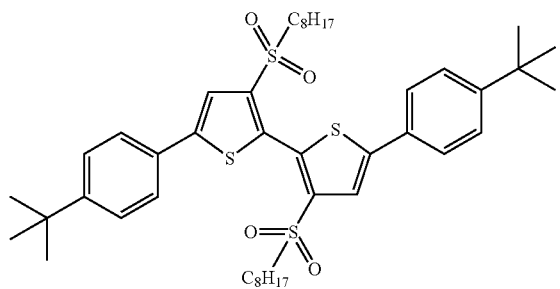 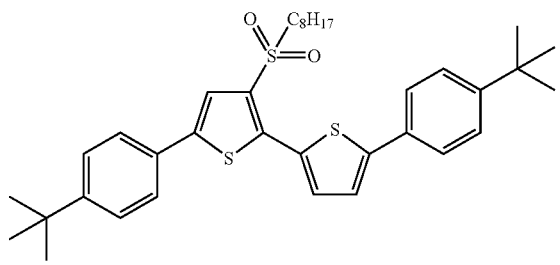

-continued
61
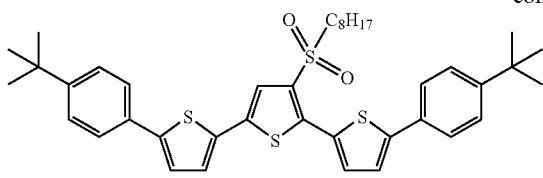
62
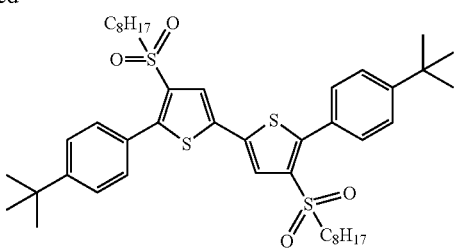
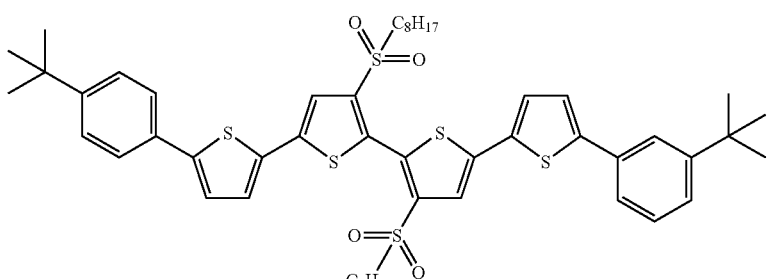
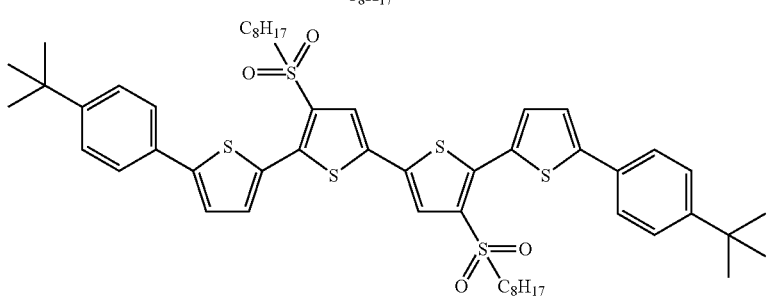
[Chemical Formula 74]
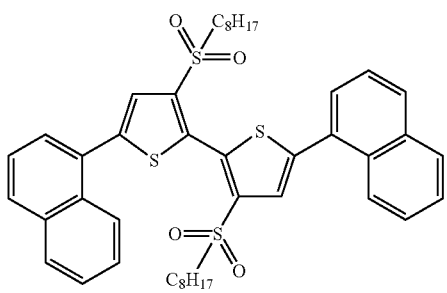
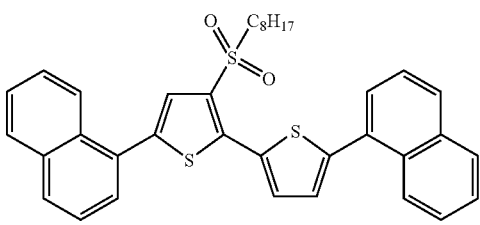
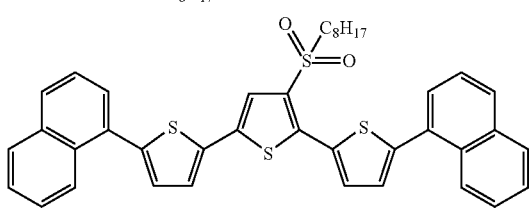
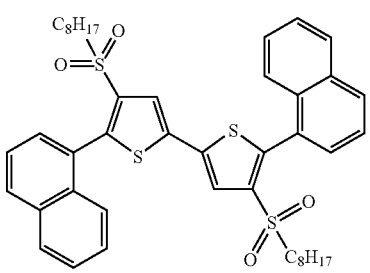
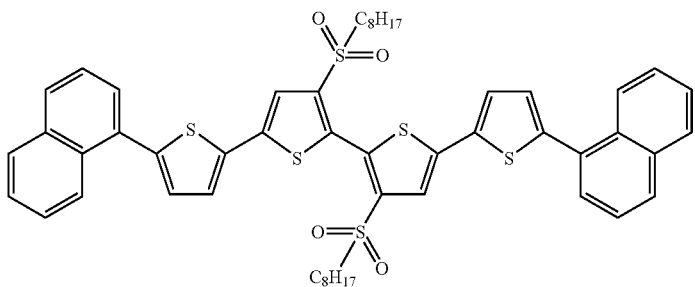

-continued

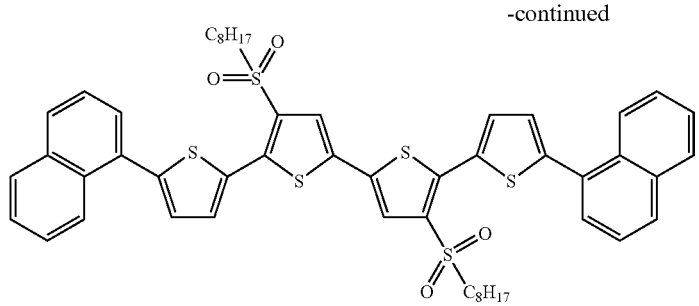

[Chemical Formula 75]

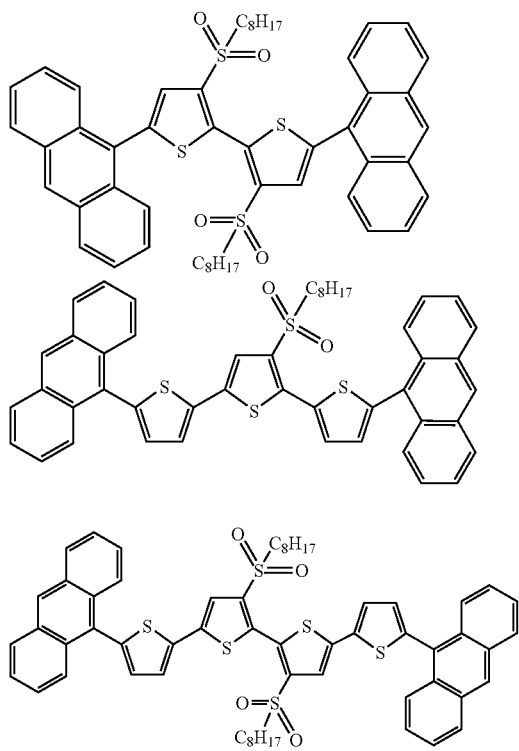

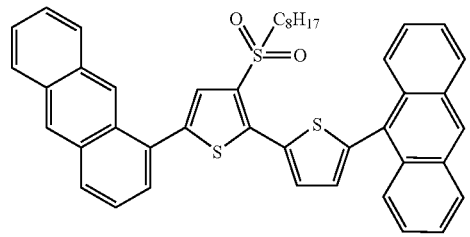

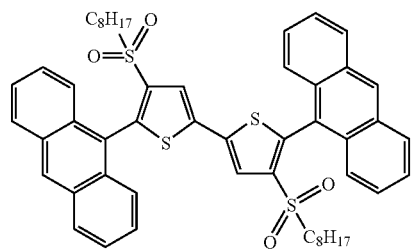

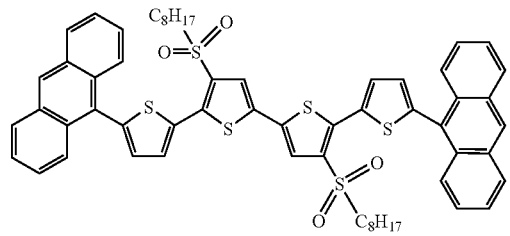

Taking the compound of the formula [18] as an example, a description will next be made about the process for the production of the sulfonylthiophene compounds according to the present invention.

The compound of the formula [18] can be obtained by a process that as shown by the below-described scheme, uses a sulfanylthiophene compound represented by the formula [17] as a starting material and selectively oxidizes it.

[Chemical Formula 76]

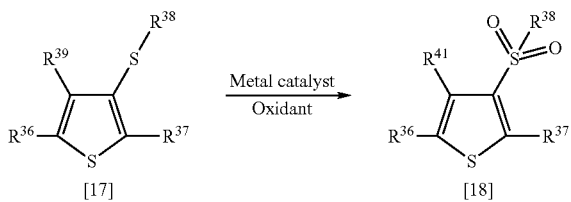

This reaction produces the sulfonylthiophene compound, which is represented by the formula [18], by reacting the sulfanylthiophene compound represented by the formula [17] with an oxidant in the presence of a metal catalyst.

Illustrative oxidant are hydrogen peroxide solution, tertiary butyl hydroperoxide, cumene hydroperoxide, permanganate salts, and periodate salts. Among these, periodate salts are preferred, with sodium periodate being more preferred, when the selectivity of the reaction is taken into consideration.

The amount of the oxidant to be used may range preferably from 0.5 to 5 molar times, especially appropriately from 1.0 molar time to 2.5 molar times, relative to the alkylthio group (sulfanyl group) which the sulfanylthiophene compound as a substrate possesses.

In this process, the existence of the metal catalyst is important. Illustrative of the metal catalyst are ruthenium catalysts, titanium catalysts, aluminum catalysts, and other metal catalysts. Specific examples include ruthenium(III) chloride n-hydrate, ruthenium(III) chloride nonhydrate, ruthenium (III) bromide n-hydrate, ruthenium(III) bromide nonhydrate, ruthenium(III) iodide n-hydrate, ruthenium(III) iodide nonhydrate, ruthenium(III) acetylacetonate, ruthenium(IV) oxide n-hydrate, ruthenium(IV) oxide anhydride, titanium (III) chloride nonhydrate, titanium(IV) tetraisopropoxide, and aluminum(III) oxide anhydride.

Among these, ruthenium(III) halides and ruthenium(IV) oxide compounds are preferred from the selectivity of the reaction, with ruthenium(III) chloride n-hydrate, ruthenium (III) chloride nonhydrate, ruthenium(IV) oxide n-hydrate and ruthenium(IV) oxide anhydride being preferred.

The amount of the metal catalyst to be used may range preferably from 0.1 to 50 mole %, especially preferably from 1 to 20 mole % based on the alkylthio group (sulfanyl group) which the sulfanylthiophene compound as a substrate possesses.

In this process, the selection of a reaction solvent is also important. As a reaction solvent, a water-soluble solvent or a mixture of a water-soluble solvent and water is preferred. Examples of the water-soluble solvent include water-soluble acid solvents and organic solvents having 1 to 4 carbon atoms, represented by acetone, acetonitrile, hydrochloric acid, acetic acid, methanol, ethanol, n-propanol, i-propanol, n-butanol, t-butanol, N,N-dimethylformamide, N,N-dimethylsulfoxide, and tetrahydrofuran. Among these, acetone and acetonitrile are preferred, with acetone being most suited from economy and reaction selectivity. When a water-soluble organic solvent and water are mixed into a mixed solvent, the ratio of the water-soluble organic solvent to water can be optional although a range of from 3:1 to 1:3 or so in terms of weight ratio is suited.

The amount of the solvent may range preferably from 1 to 100 times by weight, especially suitably from 5 to 50 times by weight relative to the sulfanylthiophene compound as a substrate.

The reaction temperature may range generally from −100 to 100° C., preferably from −20 to 40° C.

The progress of the reaction can be determined based on an analysis by thin layer chromatography (TLC) or high-pressure liquid chromatography (LC).

After completion of the reaction, the target product can be obtained by conducting general post-treatment and, if necessary, performing purification.

It is to be noted that the manner of the above-described oxidation reaction can be determined as desired and the reaction can be conducted batchwise or continuously. It can also be conducted at normal pressure or elevated pressure. In view of the heat to be evolved as a result of the progress of the reaction, it is, however, preferred to conduct the reaction batchwise in such a manner that the sulfanylthiophene compound, metal catalyst and solvent are mixed beforehand and the oxidant is then added in portions to the resultant mixture.

A description will be made about the substituents on the compounds of the respective formulas [17] and [18].

In each of the above formulas, $R^{36}$ and $R^{37}$ each independently represent a hydrogen atom, cyano group, phenyl group which may be substituted by W", hydroxyl group, amino group, formyl group, carboxyl group, alkyl group having 1 to 20 carbon atoms, haloalkyl group having 1 to 20 carbon atoms, monoalkylamino group having 1 to 10 carbon atoms, or dialkylamino group having 1 to 10 carbon atoms, $R^{38}$ represents an alkyl group having 1 to 20 carbon atoms, haloalkyl group having 1 to 20 carbon atoms, or phenyl group which may be substituted by W", $R^{39}$ represents a hydrogen atom, halogen atom, cyano group, nitro group, phenyl group which may be substituted by W", hydroxyl group, mercapto group, amino group, formyl group, carboxyl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, or —S—$R^{40}$, $R^{40}$ represents a hydrogen atom, alkyl group having 1 to 20 carbon atoms, or phenyl group which may be substituted by W", and W" represents a cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, alkylcarbonyl group having 1 to 10 carbon atoms, alkoxycarbonyl group having 1 to 10 carbon atoms, or phenyl group.

It is to be noted that specific examples of the halogen atom, alkyl group having 1 to 20 carbon atoms, haloalkyl group having 1 to 20 carbon atoms, monoalkylamino group having 1 to 10 carbon atoms, dialkylamino group having 1 to 10 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, alkylcarbonyl group having 1 to 10 carbon atoms and alkoxycarbonyl group having 1 to 10 carbon atoms are as mentioned above.

Specific examples of the phenyl group which may be substituted by W" include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-chlorophenyl, m-chlorophenyl, p-chlorophenyl, o-bromophenyl, m-bromophenyl, p-bromophenyl, o-fluorophenyl, p-fluorophenyl, o-methoxyphenyl, m-methoxyphenyl, p-methoxyphenyl, o-trifluoromethoxyphenyl, p-trifluoromethoxyphenyl, o-nitrophenyl, m-nitrophenyl, p-nitrophenyl, o-dimethylaminophenyl, m-dimethylaminophenyl, p-dimethylaminophenyl, p-cyanophenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 3,5-dichlorophenyl, 3,5-dibromophenyl, 3,5-difluorophenyl, 3,5-dinitrophenyl, 3,5-dicyanophenyl, 2,4,6-trimethylphenyl, 2,4,6-tristrifluoromethylphenyl, 2,4,6-trimethoxyphenyl, 2,4,6-tristrifluoromethoxyphenyl, 2,4,6-trichlorophenyl, 2,4,6-tribromophenyl, 2,4,6-trifluorophenyl, o-biphenylyl, m-biphenylyl, and p-biphenylyl.

As $R^{36}$ and $R^{37}$, substituents which give a smaller steric-hindrance effect are suited. Preferred are a hydrogen atom, halogen atoms, cyano group, alkyl groups having 1 to 3 carbon atoms (methyl, ethyl, n-propyl, etc.), haloalkyl groups having 1 to 3 carbon atoms ($CF_3$, $CH_2CF_3$, $CH_2CH_2CF_3$, etc.), phenyl group, and phenyl groups substituted by halogen atom (p-chlorophenyl, p-bromophenyl, p-fluorophenyl, etc.), with a hydrogen atom being more preferred.

As $R^{38}$, a linear substituent which gives a smaller steric-hindrance effect is also suited. Preferred are alkyl groups having 1 to 10 carbon atoms (methyl, ethyl, n-propyl, n-butyl, n-pentyl, n-hexyl, n-heptyl, n-octyl, n-nonyl, n-decyl, etc.), haloalkyl groups having 1 to 10 carbon atoms ($CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2Cl$, $CHCl_2$, $CCl_3$, $CH_2CH_2Cl$, $CH_2Br$, $CHBr_2$, $CBr_3$, $CH_2CH_2Br$, $CF_2CF_2CF_3$, $CF_2CF_2CF_2CF_2CF_2CF_3$, $CH_2CH_2CF_2CF_2CF_2CF_3$), phenyl group, and phenyl groups substituted by alkyl group having 1 to 3 carbon atoms (o-methylphenyl, m-methylphenyl, p-methylphenyl, etc.).

As $R^{39}$, a linear substituent which gives a smaller steric-hindrance effect is also suited. Preferred are a hydrogen atom, halogen atoms, alkyl groups having 1 to 10 carbon atoms (methyl, ethyl, n-propyl, n-butyl, n-pentyl, n-hexyl, n-heptyl, n-octyl, n-nonyl, n-decyl, etc.), phenyl group, phenyl groups substituted by alkyl group having 1 to 3 carbon atoms (o-methylphenyl, m-methylphenyl, p-methylphenyl, etc.), and thioalkyl groups represented by —S—$R^{40}$. As $R^{40}$, a linear substituent which gives a smaller steric-hindrance effect is also suited. Preferred are alkyl groups having 1 to 10 carbon atoms (methyl, ethyl, n-propyl, n-butyl, n-pentyl, n-hexyl, n-heptyl, n-octyl, n-nonyl, n-decyl, etc.), haloalkyl groups having 1 to 10 carbon atoms ($CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2Cl$, $CHCl_2$, $CCl_3$, $CH_2CH_2Cl$, $CH_2Br$, $CHBr_2$, $CBr_3$, $CH_2CH_2Br$, $CF_2CF_2CF_3$, $CF_2CF_2CF_2CF_2CF_3$, $CH_2CH_2CF_2CF_2CF_3$), phenyl group, and phenyl groups substituted by alkyl group having 1 to 3 carbon atoms (o-methylphenyl, m-methylphenyl, p-methylphenyl, etc.).

As $R^{41}$, a substituent which gives a smaller steric-hindrance effect is also suited. Preferred are a hydrogen atom, halogen atoms, alkyl groups having 1 to 10 carbon atoms (methyl, ethyl, n-propyl, n-butyl, n-pentyl, n-hexyl, n-heptyl, n-octyl, n-nonyl, n-decyl, etc.), phenyl group, phenyl groups substituted by alkyl group having 1 to 3 carbon atoms (o-methylphenyl, m-methylphenyl, p-methylphenyl, etc.), and sulfonyl groups represented by $—S(O)_2—R^{40}$. As $R^{40}$, a substituent which gives a smaller steric-hindrance effect is suited. Preferred are alkyl groups having 1 to 10 carbon atoms (methyl, ethyl, n-propyl, n-butyl, n-pentyl, n-hexyl, n-heptyl, n-octyl, n-nonyl, n-decyl, etc.), haloalkyl groups having 1 to 10 carbon atoms ($CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2Cl$, $CHCl_2$, $CCl_3$, $CH_2CH_2Cl$, $CH_2Br$, $CHBr_2$, $CBr_3$, $CH_2CH_2Br$, $CF_2CF_2CF_3$, $CF_2CF_2CF_2CF_2CF_3$, $CH_2CH_2CF_2CF_2CF_3$), phenyl group, and phenyl groups substituted by alkyl group having 1 to 3 carbon atoms (o-methylphenyl, m-methylphenyl, p-methylphenyl, etc.). The above-described process is particularly suited for the synthesis of compounds in which $R^{36}$ and $R^{37}$ are hydrogen atoms, $R^{38}$ is an alkyl group having 1 to 10 carbon atoms or a haloalkyl group having 1 to 10 carbon atoms, $R^{39}$ is a thioalkyl group represented by $—S—R^{40}$, and $R^{40}$ is an alkyl group having 1 to 10 carbon atoms or a haloalkyl group having 1 to 10 carbon atoms.

Taking the compounds of the respective formulas [34] and [35] as examples, a description will be made about the process for the production of the mono and bissulfonylthiophene compounds of the invention.

The sulfonylthiophene compounds of the respective formulas [34] and [35] can be obtained by a process that as will be shown by the below-described scheme, uses a butynediol compound represented by the formula [27] as a starting material and cyclizes it.

[Chemical Formula 77]

Step 1

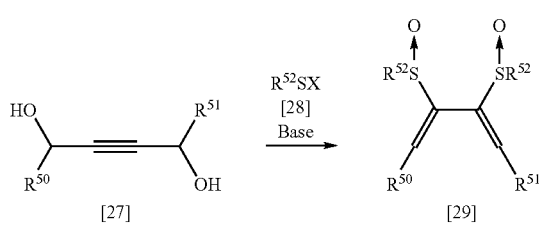

Step 2

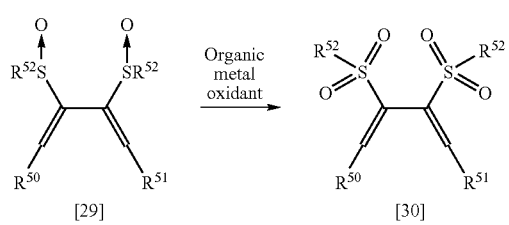

[Chemical Formula 78]

Step 3

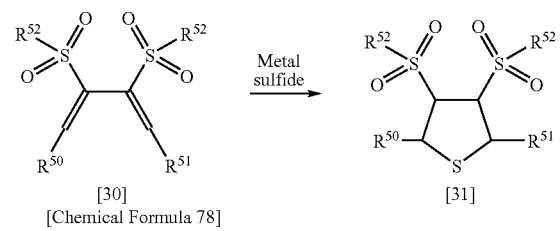

Step 4

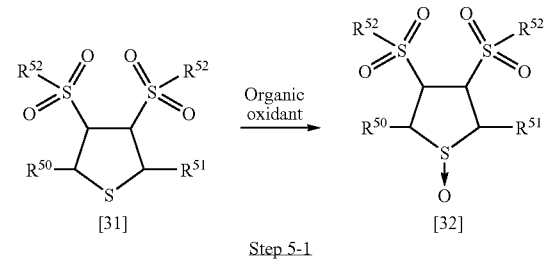

Step 5-1

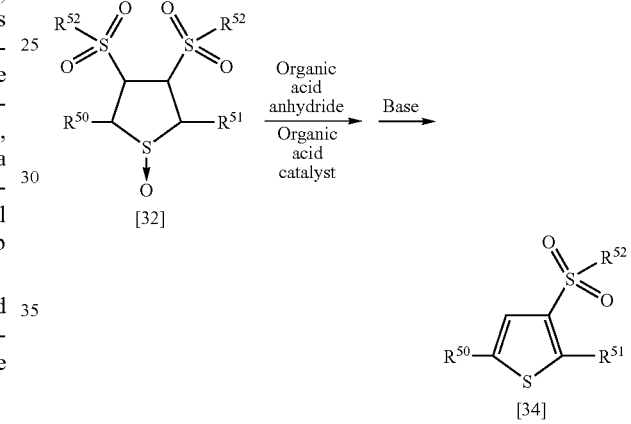

Step 5-2

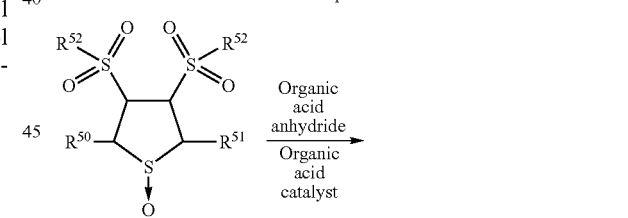

[1] Step 1

This step reacts a butynediol compound represented by the formula [27] and a sulfenyl compound represented by the formula [28] in the presence of a base to produce a bissulfanylbutadiene compound represented by the formula [29].

Examples of the sulfenyl compound include 1-butanesulfenyl chloride, 2-butanesulfenyl chloride, 1-hexanesulfenyl chloride, 2-hexanesulfenyl chloride, 1-octanesulfenyl chloride, 2-octanesulfenyl chloride, 1-decanesulfenyl chloride, and 2-decanesulfenyl chloride. Among these, 1-butanesulfenyl chloride is preferred.

The amount of the sulfenyl compound to be used may range preferably from 0.1 to 5 molar times, especially suitably from 1.8 to 2.2 molar times, relative to the butynediol compound as the substrate.

It is important to conduct this reaction in the presence of a base. Usable examples of the base include alkylamines such as diethylamine, triethylamine, diisopropylamine, diisopropylethylamine and di-n-butylamine, aromatic amines such as pyridine and picoline, and inorganic bases such as sodium hydrogencarbonate and potassium carbonate. Among these, triethylamine is preferred.

The amount of the base to be used may range preferably from 1 to 10 molar times, especially suitably from 1.8 to 2.2 molar times, relative to the butynediol compound as the substrate.

As the reaction solvent, various solvents can be used insofar as they do not affect the reaction. In particular, halogenated hydrocarbons such as methylene chloride, chloroform and 1,2-dichloroethane and ether compounds such as tetrahydrofuran (THF), 1,4-dioxane, 1,2-dimethoxyethane and diethylene glycol dimethyl ether are preferred, with methylene chloride being most suited.

The amount of the solvent may range preferably from 1 to 100 times by weight, especially suitably from 20 to 50 times by weight, relative to the butynediol compound as the substrate.

The reaction temperature may range generally from $-100$ to $100°$ C., preferably from $-100$ to $30°$ C.

The progress of the reaction can be determined based on an analysis by thin layer chromatography or gas chromatography.

After completion of the reaction, the target product can be obtained by conducting general post-treatment and, if necessary, performing purification.

[2] Step 2

This step treats the bissulfanylbutadiene compound represented by the formula [29] with an organic oxidant to produce a bissulfonylbutadiene compound represented by the formula [30].

Examples of the organic oxidant include peracid compounds such as m-chloroperbenzoic acid, perbenzoic acid and peracetic acid; quinone compounds such as 2,3-dichloro-5,6-dicyano-p-benzoquinone; and peroxides such as 2,3,5,6-tetrachloro-p-benzoquinone, t-butyl hydroxide and cumene hydroxide. Taking reactivity into consideration, however, m-chloroperbenzoic acid is preferred.

The amount of the organic oxidant to be used may range preferably from 1.0 to 2.0 molar times, especially suitably from 1.1 to 1.5 molar times, relative to the bissulfanylbutadiene compound as the substrate.

Illustrative of a reaction solvent are aromatic hydrocarbons such as toluene and xylene; and halogenated hydrocarbons such as methylene chloride, chloroform, 1,2-dichloroethane and 1,2-dichloropropane, with methylene chloride being preferred.

The amount of the solvent may range preferably from 1 to 100 times by weight, especially suitably from 20 to 50 times by weight, relative to the bissulfanylbutadiene compound as the substrate.

The reaction temperature may range generally from $-100$ to $100°$ C., preferably from 0 to $40°$ C.

The progress of the reaction can be determined based on an analysis by thin layer chromatography.

After completion of the reaction, the target product can be obtained by conducting general post-treatment and, if necessary, performing purification.

[3] Step 3

This step reacts the bissulfonylbutadiene compound represented by the formula [30] with a metal sulfide to produce a 3,4-bissulfonylthiolane compound represented by the formula [31].

Examples of the metal sulfide include sodium sulfide and potassium sulfide, with sodium sulfide being preferred when reactivity is taken into consideration.

The amount of the metal sulfide to be used may range preferably from 0.8 to 3 molar times, especially suitably from 1.0 to 1.3 molar times, relative to the bissulfonylbutadiene compound as the substrate.

As a reaction solvent, an alcohol solvent is preferred. Illustrative are alkyl alcohols having 1 to 10 carbon atoms represented by methanol, ethanol, n-propanol, i-propanol, n-octanol, and n-decanol, with ethanol being preferred.

The amount of the solvent may range preferably from 1 to 100 times by weight, especially suitably from 20 to 50 times by weight, relative to the bissulfonylbutadiene compound as the substrate.

The reaction temperature may range generally from $-100$ to $100°$ C., preferably from 0 to $40°$ C. The progress of the reaction can be determined based on an analysis by thin layer chromatography.

After completion of the reaction, the target product can be obtained by conducting general post-treatment and, if necessary, performing purification.

[4] Step 4

This step treats the 3,4-bissulfonylthiolane compound represented by the formula [31] with an organic oxidant to produce a 3,4-bissulfonylsulfuran compound represented by the formula [32].

Examples of the organic oxidant include peracid compounds such as m-chloroperbenzoic acid, perbenzoic acid and peracetic acid; quinone compounds such as 2,3-dichloro-5,6-dicyano-p-benzoquinone; and peroxides such as 2,3,5,6-tetrachloro-p-benzoquinone, t-butyl hydroxide and cumene hydroxide. Taking reactivity into consideration, however, m-chloroperbenzoic acid is preferred.

The amount of the organic oxidant to be used may range preferably from 1.0 to 2.0 molar times, especially suitably from 1.1 to 1.5 molar times, relative to the 3,4-bissulfonylthiolane compound as the substrate.

Illustrative of a reaction solvent are aromatic hydrocarbons such as toluene and xylene; and halogenated hydrocarbons such as methylene chloride, chloroform, 1,2-dichloroethane and 1,2-dichloropropane, with methylene chloride being preferred.

The amount of the solvent may range preferably from 1 to 100 times by weight, especially suitably from 20 to 50 times by weight, relative to the 3,4-bissulfonylthiolane compound as the substrate.

The reaction temperature may range generally from $-100$ to $100°$ C., preferably from 0 to $40°$ C.

The progress of the reaction can be determined based on an analysis by thin layer chromatography.

After completion of the reaction, the target product can be obtained by conducting general post-treatment and, if necessary, performing purification.

[5] Step 5-1

This step reacts the 3,4-bissulfonylsulfuran compound represented by the formula [32] with an organic acid anhydride in the presence of an organic acid catalyst and then conducts treatment with a base to produce a 3,4-bissulfonylthiophene compound represented by the formula [33].

Usable examples of the organic acid anhydride include aliphatic carboxylic acid anhydrides and aromatic carboxylic acid anhydrides. Economical aliphatic carboxylic acid anhydrides are preferred, with acetic anhydride being particularly preferred.

The amount of the organic acid anhydride to be used may range preferably from 0.8 to 5.0 molar times, especially suitably from 1.0 to 1.3 molar times, relative to the 3,4-bissulfonylsulfuran compound as the substrate.

Illustrative of the organic acid catalyst are aliphatic acids such as formic acid, acetic acid and propionic acid, and sulfonic acids such as benzenesulfonic acid, p-toluenesulfonic acid, methanesulfonic acid, ethanesulfonic acid and trifluoromethanesulfonic acid. Sulfonic acids are preferred, with methanesulfonic acid being particularly preferred.

The amount of the organic acid catalyst to be used may range preferably from 0.1 to 50 mole %, especially suitably from 10 to 30 mole %, based on the 3,4-bissulfonylsulfuran compound as the substrate.

Illustrative of the base include alkylamines such as diethylamine, triethylamine, diisopropylamine, diisopropylethylamine and di-n-butylamine, aromatic amines such as pyridine and picoline, and inorganic bases such as sodium hydrogencarbonate and potassium carbonate. Among these, potassium carbonate is preferred.

The amount of the base to be used may range preferably from 1 to 10 molar times, especially suitably from 1.0 to 2.0 molar times, relative to the 3,4-bissulfonylsulfuran compound as the substrate.

As a reaction solvent, an organic solvent which takes no direct part in the reaction can be used, although the organic acid anhydride may be added in an excess amount to serve as a solvent. Examples of the organic solvent include aromatic hydrocarbons such as toluene and xylene; and halogenated hydrocarbons such as methylene chloride, chloroform, 1,2-dichloroethane and 1,2-dichloropropane. Halogenated hydrocarbons are preferred, with methylene chloride being especially suited.

The amount of the solvent may range preferably from 1 to 100 times by weight, especially suitably from 20 to 50 times by weight, relative to the 3,4-bissulfonylsulfuran compound as the substrate.

The reaction temperature may range generally from −100 to 100° C., preferably from −20 to 40° C.

The progress of the reaction can be determined based on an analysis by thin layer chromatography.

After completion of the reaction, the target product can be obtained by conducting general post-treatment and, if necessary, performing purification.

[6] Step 5-2

This step reacts the 3,4-bissulfonylsulfuran compound represented by the formula [32] with an organic acid anhydride in the presence of an organic acid catalyst to produce a 3,4-bissulfonyldihydrothiophene compound represented by the formula [33] and then treat it with an inorganic oxidant to produce a 3,4-bissulfonylthiophene compound represented by the formula [35].

Usable examples of the organic acid anhydride include aliphatic carboxylic acid anhydrides and aromatic carboxylic acid anhydrides. Economical aliphatic carboxylic acid anhydrides are preferred, with acetic anhydride being particularly preferred.

The amount of the organic acid anhydride to be used may range preferably from 0.8 to 5.0 molar times, especially suitably from 1.0 to 1.3 molar times, relative to the 3,4-bissulfonylsulfuran compound as the substrate.

Illustrative of the organic acid catalyst are aliphatic acids such as formic acid, acetic acid and propionic acid, and sulfonic acids such as benzenesulfonic acid, p-toluenesulfonic acid, methanesulfonic acid, ethanesulfonic acid and trifluoromethanesulfonic acid. Sulfonic acids are preferred, with methanesulfonic acid being particularly preferred.

The amount of the organic acid catalyst to be used may range preferably from 0.1 to 50 mole %, especially suitably from 10 to 30 mole %, based on the 3,4-bissulfonylsulfuran compound as the substrate.

In this case, an organic solvent which takes no direct part in the reaction can be used, although the organic acid anhydride may be added in an excess amount to serve as a solvent. Examples of the organic solvent include aromatic hydrocarbons such as toluene and xylene; and halogenated hydrocarbons such as methylene chloride, chloroform, 1,2-dichloroethane and 1,2-dichloropropane. Halogenated hydrocarbons are preferred, with methylene chloride being especially suited.

The amount of the solvent may range preferably from 1 to 100 times by weight, especially suitably from 20 to 50 times by weight, relative to the 3,4-bissulfonylsulfuran compound as the substrate.

The reaction temperature may range generally from −100 to 100° C., especially preferably from −20 to 40° C. The progress of the reaction can be determined based on an analysis by thin layer chromatography.

After completion of the reaction, the target product can be obtained by conducting general post-treatment and, if necessary, performing purification.

Examples of the inorganic oxidant include thionyl chloride, permanganate salts, and periodate salts. Taking reactivity into consideration, thionyl chloride is suited. The amount of the inorganic oxidant may range preferably from 1.0 to 5.0 times by weight, especially suitably from 2.5 to 3.5 times by weight, relative to the 3,4-bissulfonyldihydrothiophene compound as the substrate.

Examples of a reaction solvent include aromatic hydrocarbons such as toluene and xylene; and halogenated hydrocarbons such as methylene chloride, chloroform, 1,2-dichloroethane and 1,2-dichloropropane. Halogenated hydrocarbons are preferred, with methylene chloride being especially suited.

The amount of the solvent may range preferably from 1 to 100 times by weight, especially suitably from 20 to 50 times by weight, relative to the 3,4-bissulfonyldihydrothiophene compound as the substrate.

The reaction temperature may range generally from −100 to 100° C., especially preferably from 0 to 70° C.

The progress of the reaction can be determined based on an analysis by thin layer chromatography.

After completion of the reaction, the target product can be obtained by conducting general post-treatment and, if necessary, performing purification.

It is to be noted that the reaction in each of the above-described steps can be conducted either batchwise or continuously and either at normal pressure or elevated pressure.

A description will be made about the substituents on the compounds of the respective formulas [27] to [35].

In each of the above formulas, $R^{50}$ and $R^{51}$ each independently represent a hydrogen atom, halogen atom, cyano group, phenyl group which may be substituted by W''', alkyl group having 1 to 10 carbon atoms, or haloalkyl group having 1 to 10 carbon atoms, $R^{52}$ represents a hydrogen atom, alkyl group having 1 to 10 carbon atoms, or phenyl group which may be substituted by W", and W" represents a halogen atom, cyano group, nitro group, alkyl group having 1 to 10 carbon atoms, haloalkyl group having 1 to 10 carbon atoms, alkenyl group having 1 to 10 carbon atoms, alkynyl group having 1 to 10 carbon atoms, alkoxy group having 1 to 10 carbon atoms, or phenyl group.

It is to be noted that specific examples of the halogen atom, alkyl group having 1 to 10 carbon atoms, haloalkyl group having 1 to 10 carbon atoms, alkenyl group having 1 to 10 carbon atoms, alkynyl group having 1 to 10 carbon atoms and alkoxy group having 1 to 10 carbon atoms are as mentioned above.

Specific examples of the phenyl group which may be substituted by W" include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-chlorophenyl, m-chlorophenyl, p-chlorophenyl, o-bromophenyl, m-bromophenyl, p-bromophenyl, o-fluorophenyl, p-fluorophenyl, o-methoxyphenyl, m-methoxyphenyl, p-methoxyphenyl, o-trifluoromethoxyphenyl, p-trifluoromethoxyphenyl, o-nitrophenyl, m-nitrophenyl, p-nitrophenyl, o-dimethylaminophenyl, m-dimethylaminophenyl, p-dimethylaminophenyl, p-cyanophenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 3,5-dichlorophenyl, 3,5-dibromophenyl, 3,5-difluorophenyl, 3,5-dinitrophenyl, 3,5-dicyanophenyl, 2,4,6-trimethylphenyl, 2,4,6-tristrifluoromethylphenyl, 2,4,6-trimethoxyphenyl, 2,4,6-tristrifluoromethoxyphenyl, 2,4,6-trichlorophenyl, 2,4,6-tribromophenyl, 2,4,6-trifluorophenyl, o-biphenylyl, m-biphenylyl, and p-biphenylyl.

As $R^{50}$ and $R^{51}$, substituents which give a smaller steric-hindrance effect are suited. Preferred are a hydrogen atom, halogen atoms, cyano group, alkyl groups having 1 to 3 carbon atoms (methyl, ethyl, n-propyl, etc.), haloalkyl groups having 1 to 3 carbon atoms ($CF_3$, $CH_2CF_3$, $CH_2CH_2CF_3$, etc.), phenyl group, and phenyl groups substituted by halogen atom (p-chlorophenyl, p-bromophenyl, p-fluorophenyl, etc.), with a hydrogen atom being more preferred.

As $R^{52}$, a substituent which gives a smaller steric-hindrance effect is suited. Preferred are a hydrogen atom, alkyl groups having 1 to 3 carbon atoms (methyl, ethyl, n-propyl, etc.), phenyl group, and phenyl groups substituted by alkyl group having 1 to 3 carbon atoms (o-methylphenyl, m-methylphenyl, p-methylphenyl, etc.).

The production process including the above-described steps 1 to 5-1 or 5-2 is a process most suited for the synthesis of the compounds in which $R^{50}$ and $R^{51}$ are hydrogen atoms.

No particular limitation is imposed on the process for the production of the sulfonylthiophene oligomer compounds represented by the formulas [2] and [16], respectively, and sulfonylbithiophene compounds represented by the formulas [19] to [22], respectively, and they can be obtained by converting the end substituents of the sulfonylthiophene compounds, which are represented by the formula [1] or [24], into suitable substituents and then causing coupling by a desired method to be described subsequently herein. Concerning the thus-obtained compounds represented by the formulas [2] and [16], respectively, the end substituents of their thiophene rings (or other spacers represented by the formulas [3] to [11], respectively) can be converted into suitable substituents and can then be coupled by a desired method.

No particular limitations is imposed on the coupling method, and usable examples include the biaryl coupling, the Stille coupling, the Suzuki coupling, the Ullmann coupling, the Heck reaction, the Sonogashira coupling, and the Grignard reaction.

A description will hereinafter be made of illustrative methods for changing the end substituents of the sulfonylthiophene compounds of the respective formulas [1], [2] and [16] for the purpose of conducting coupling.

No particular limitation is imposed on the halogenation method upon converting the end substituents of the sulfonylthiophene compounds into halogens. It is possible to use, for example, the method described in Hetero Cycles, p. 1927, 1996 or in Journal of Organic Chemistry (J. Org. Chem.), p. 3072, 1993.

No particular limitation is imposed on the trialkylsilylation method upon converting the end substituents of the sulfonylthiophene compounds into trialkylsilyl groups. The method described in J. Org. Chem., p. 3072, 1993 may be followed.

No particular limitation is imposed on the biaryl coupling method. For example, the method described in Tetrahedron, p. 3327, 1980 may be followed.

No particular limitation is imposed on the Stille coupling method. For example, the method described in J. Org. Synth., p. 553, 1998 may be followed. It is to be noted that the yield can be improved by adding a copper reagent to the reaction system as needed.

No particular limitation is imposed on the Suzuki coupling method. For example, the method described in Tetrahedron, p. 8301, 1994 may be followed.

No particular limitation is imposed on the Ullmann coupling method. For example, the method described in Org. Lett., p. 224, 1994 may be followed.

No particular limitation is imposed on the coupling method by the Heck reaction. For example, the method described in Org. Lett., p. 345, 1982 may be followed.

No particular limitation is imposed on the Sonogashira coupling method. For example, the method described in Tetrahedron letters (Tetrahedron. Lett.), p. 4467, 1975 may be followed.

No particular limitation is imposed on the coupling method by the Grignard reaction. For example, the method described in J. Org. Synth., p. 407, 1988 may be followed.

Further, the sulfonylthiophene compounds of the respective formulas [1], [24], [2] and [16] can be formed into such sulfonylthiophene polymer compounds as represented by the above-described formulas [25] and [26], respectively, by polymerization.

Although no particular limitation is imposed on the molecular weights of the sulfonylthiophene polymers, their weight average molecular weights may range preferably from 8,000 to 150,000, more preferably from 8,500 to 120,000. It is to be noted that these weight average molecular weights are polystyrene-converted values as determined by gel permeation chromatography.

Specific examples of the sulfonylthiophene polymers include, but are not limited to, the below-described compounds. In each of the following formulas, k stands for an integer of from 50 to 5,000, and may preferably be a number that gives the above-described weight average molecular weight.

[Chemical Formula 79]
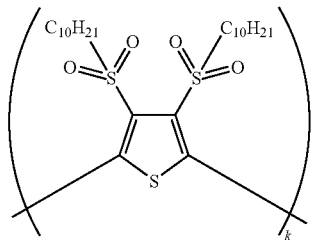 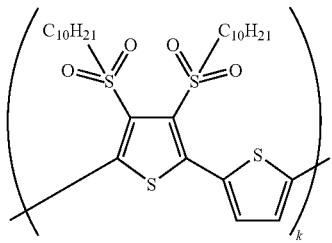
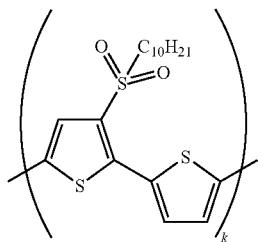 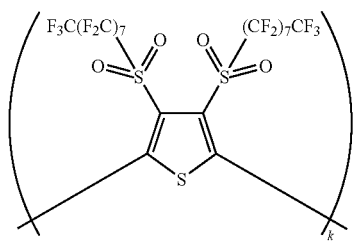
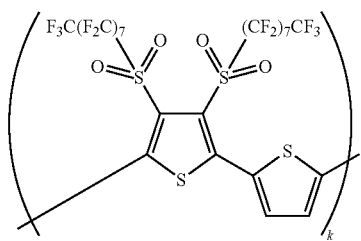 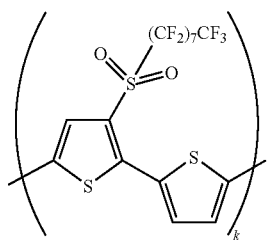
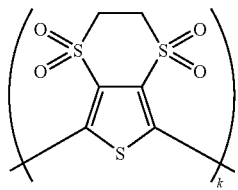 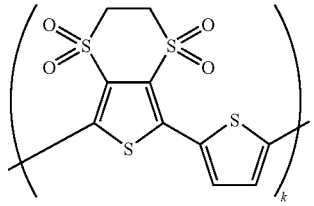
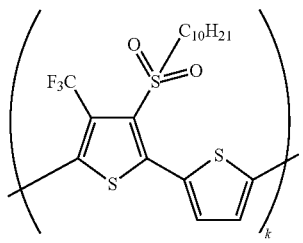
[Chemical Formula 80]
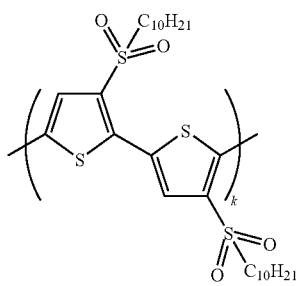 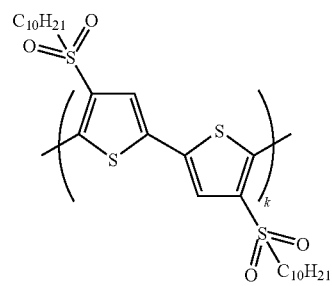

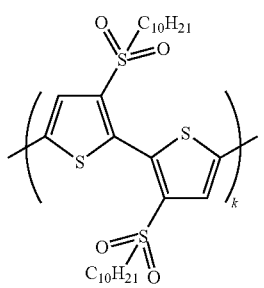
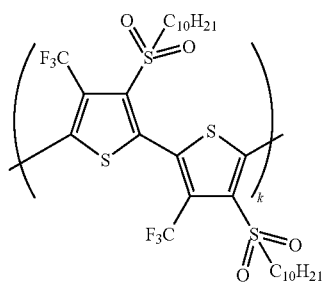
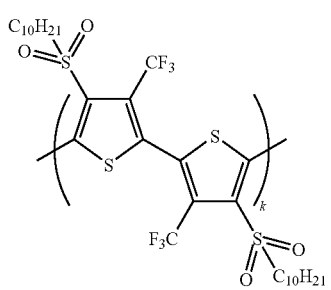
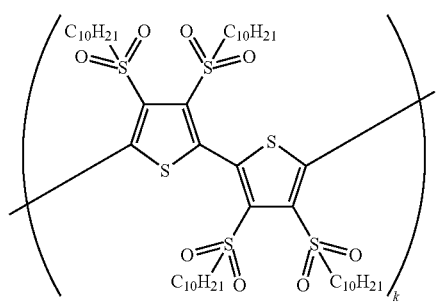
[Chemical Formula 81]
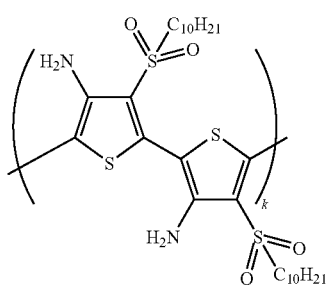
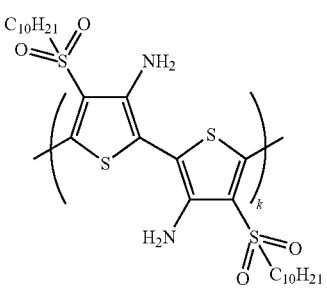
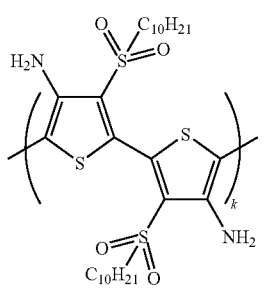
[Chemical Formula 82]
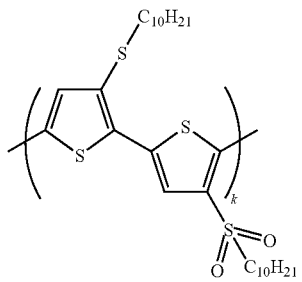
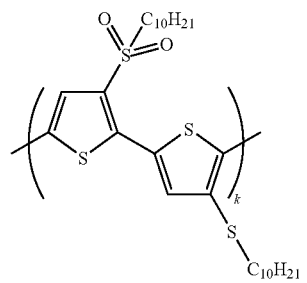

-continued
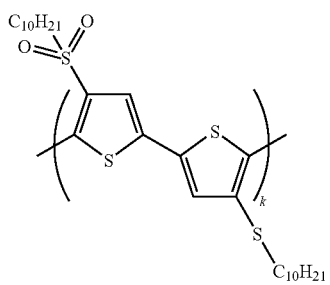
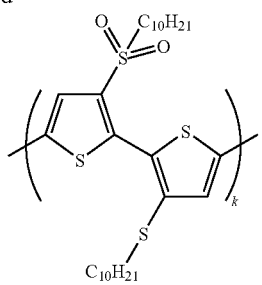
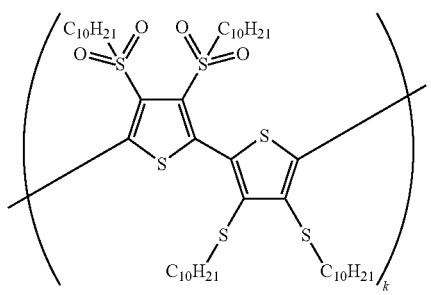
[Chemical Formula 83]
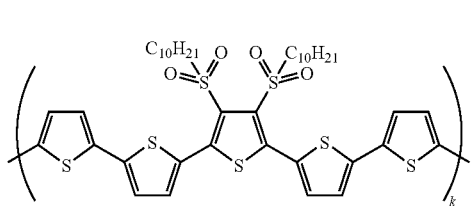
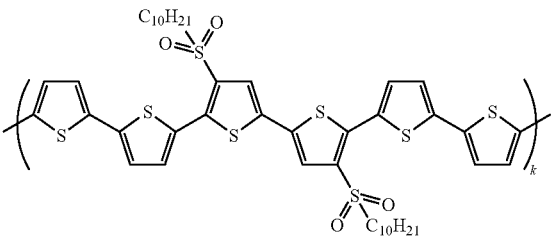
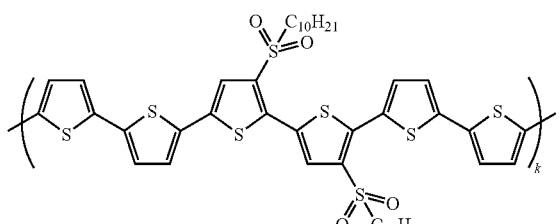
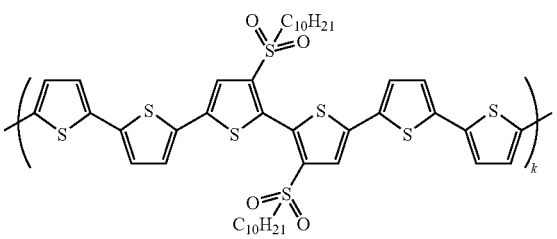
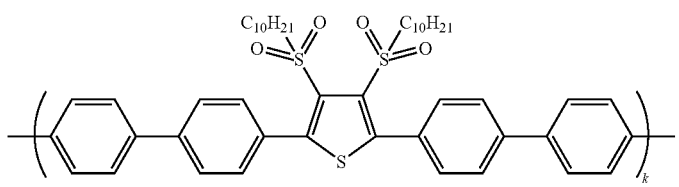
[Chemical Formula 84]
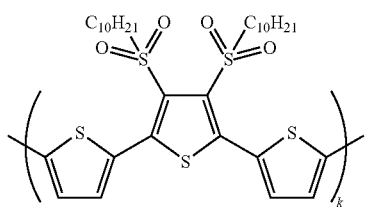
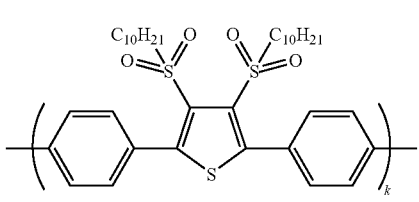
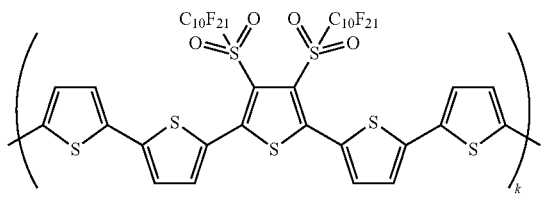
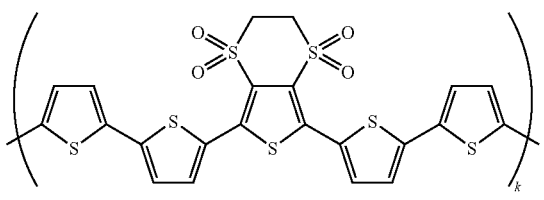

-continued

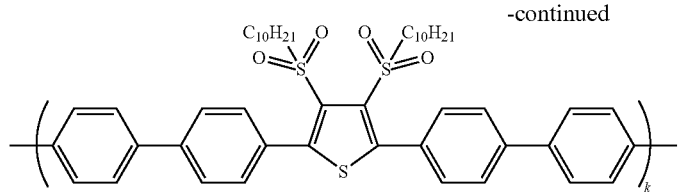

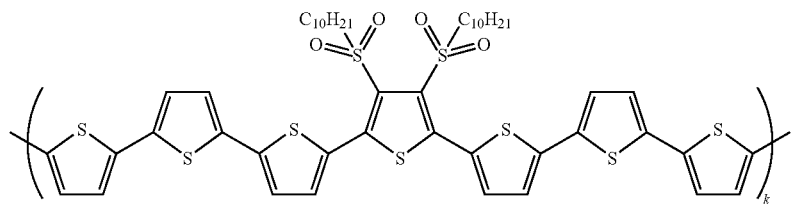

[Chemical Formula 85]

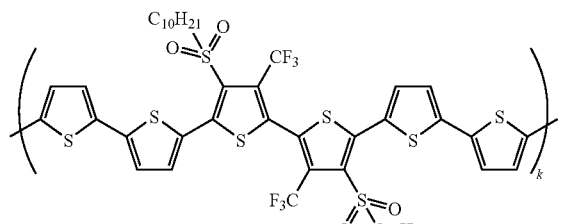
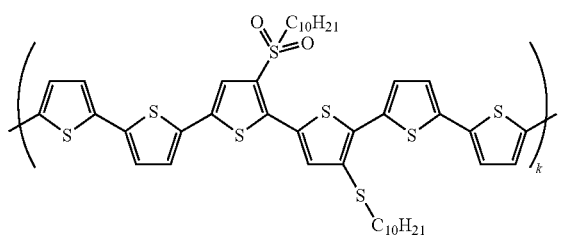

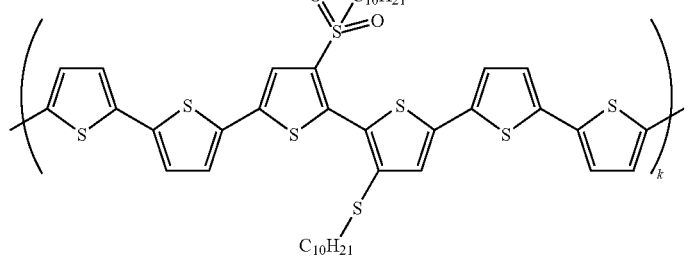

[Chemical Formula 86]

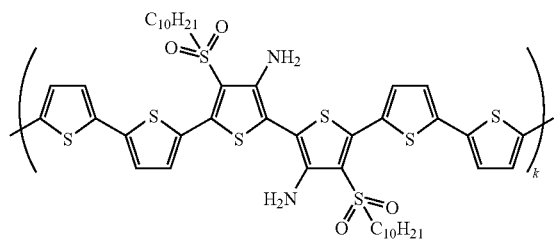
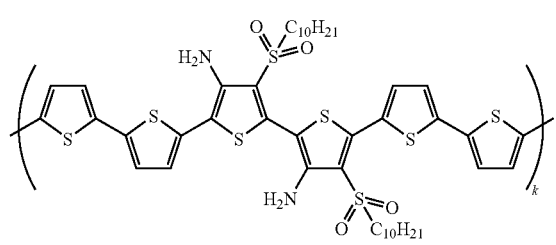

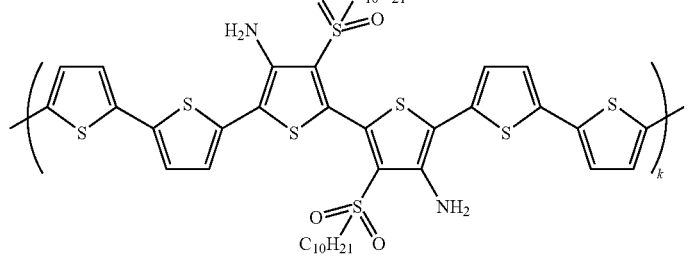

No particular limitation is imposed on the polymerization process insofar as it can polymerize the sulfonylthiophene compounds. Usable examples include chemical oxidative polymerization, electrolytic oxidative polymerization, and catalytic polymerization. When conducting a polymerization reaction on an electrode surface, chemical oxidative polymerization or electrolytic oxidative polymerization is preferred for the formability of a polymer on the electrode surface, with electrolytic oxidative polymerization being especially suited.

No particular limitation is imposed on an oxidant to be used in chemical oxidative polymerization. Illustrative are ammonium persulfate, tetraammonium peroxide, iron chloride, and cerium sulfate.

Electrolytic oxidative polymerization can be conducted, for example, by adding an oxidant to a sulfonylthiophene compound and thoroughly stirring the resulting mixture, adding an organic solvent to prepare a uniform solution, and using a three-electrode beaker cell or the like equipped with a platinum mesh counter electrode or the like. Described specifically, polymerization is conducted by the potential sweep method making use of an electrochemical measurement system, the constant potential method or the like while using a platinum plate, the surfaces of which have been scratched with emery paper or the like, as a test electrode substrate and Ag/Ag$^+$ as a reference electrode. As a result, the target thiophene polymer deposits in the form of a film on the electrode.

Examples of the oxidant useful in the electrolytic oxidative polymerization include hydrochloric acid, sulfuric acid, perchloric acid, trifluoromethanesulfonic acid, and paratoluenesulfonic acid. Among these, perchloric acid is suited.

Examples of the organic solvent include N,N-dimethylformamide, tetrahydrofuran, acetonitrile, dichloromethane, dimethylsulfoxide, methanol, and ethanol, with the use of acetonitrile or N,N-dimethylformamide being particularly suited.

Catalytic polymerization is a process that reacts at least one compound, which is selected from the sulfonylthiophene compounds of [1], [24], [2] and [16], in the presence of a metal catalyst to produce a sulfonylthiophene polymer.

No particular limitation is imposed on the sulfonylthiophene compound to be used in catalytic polymerization, but preferred is a sulfonylthiophene compound the end substituents of which are halogen atoms. As these halogen atoms, bromine atoms are suited.

As the metal catalyst, a nickel complex or the like can be mentioned. Specific examples include combinations of nickel (0) complexes represented by bis(1,5-cyclooctadiene)nickel (0) and tetrakis(triphenylphosphine)nickel(0) or nickel(II) complexes represented by nickel chloride, bis(triphenylphosphine)nickel(II) dichloride, [1,2-bis(diphenylphosphino) ethane]nickel(II) dichloride, [1,3-bis(diphenylphosphino) propane]nickel(II) dichloride and tris(2,2'-bipyridyl)nickel (II) dibromide and various ligands represented by 1,5-cyclooctadiene, 2,2'-bipyridine and triphenylphosphine. Among these, the combination of bis(1,5-cyclooctadiene) nickel and 1,5-cyclooctadiene or 2,2'-bipyridine is preferred from the standpoint that the resulting polymer has a high degree of polymerization.

The amount of the metal catalyst to be used may range preferably from 0.05 to 2.0 molar times, especially preferably from 0.05 to 0.8 molar time, relative to the halogen atoms which the sulfonylthiophene compound as the substrate possesses.

The amount of the ligand to be used may range preferably from 0.05 to 2.0 molar times, especially preferably from 0.05 to 0.8 molar time, relative to the halogen atoms which the phosphorylthiophene compound as the substrate possesses.

Preferred examples of a reaction solvent include amide compounds such as N,N-dimethylformamide and N,N-dimethylacetamide; aromatic hydrocarbons such as benzene, toluene and xylene; and ether compounds such as tetrahydrofuran (THF), 1,4-dioxane, 1,2-dimethoxyethane, and diethylene glycol dimethyl ether. Among these, 1,4-dioxane is suited in that the resulting polymer has a high degree of polymerization.

The amount of the solvent may range preferably from 1 to 100 times by weight, especially suitably from 20 to 50 times by weight, relative to the halogenated thiophene compound as the substrate.

The reaction temperature may range generally from −100 to 100° C., especially preferably from 40 to 80° C.

The progress of the reaction can be determined by gel permeation chromatography.

After completion of the reaction, the target product can be obtained by conducting general post-treatment and, if necessary, performing purification.

The above-described sulfonylthiophene compound of the formula [1], [24], [2] or [16] can be reacted with an aryl compound represented by the formula [99] in the presence of a base, metal catalyst and ligand so as to lead to bisarylthiophene compound.

[Chemical Formula 87]

$$R^{99}\text{-X} \qquad [99]$$

wherein $R^{99}$ represents a phenyl group which may be substituted by W, naphthyl group which may be substituted by W, or anthranyl group which may be substituted by W, X represents a halogen atom, and W has the same meaning as defined above.

In the above reaction, the amount of the aryl compound to be used may range preferably from 2.0 to 5.0 molar times, especially suitably from 2.0 to 3.0 molar times, relative to the sulfonylthiophene compound.

Illustrative of the base are carbonate compounds of alkaline earth metals represented by cesium carbonate, potassium carbonate and the like, amine compounds represented by triethylamine and the like, and alkyl metal compounds represented by n-butyl lithium and the like. Among these, the carbonate compounds of alkaline earth metals represented by cesium carbonate, potassium carbonate and the like are preferred, with cesium carbonate being particularly suited for the availability of a high yield.

The amount of the base to be used may range preferably from 2.0 to 5.0 molar times, especially suitably from 2.0 to 3.0 molar times, relative to the sulfonylthiophene compound.

Illustrative of the ligand are phosphine compounds containing one or more alkyl groups having 1 to 10 carbon atoms represented by tri-n-butylphosphine, tricyclohexylphosphine and the like, and phosphine compounds containing one or more phenyl groups represented by triphenylphosphine, biphenyl di-t-butylphosphine and the like. Among these, biphenyl di-t-butylphosphine is preferred for the availability of a high yield.

The amount of the ligand to be used may range preferably from 0.1 to 0.5 molar time, especially preferably from 0.1 to 0.3 molar time, relative to the thiophene compound as the substrate.

Illustrative of the metal catalyst are tetrakis(triphenylphosphine)palladium(0), dichlorobis(triphenylphosphine)palladium(II), palladium acetate, dichloro[1,2-bis(diphenylphosphino)ethane] palladium(II), and dichloro[1,3-bis (diphenylphosphino) propane]palladium(II). Among these, palladium acetate is most suited for the availability of a high yield.

The amount of the metal catalyst to be used may range preferably from 0.01 to 0.2 molar time, particularly suitably from 0.05 to 0.15 molar time, relative to the thiophene compound as the substrate.

Preferred examples of a reaction solvent include amide compounds such as N,N-dimethylformamide and N,N-dimethylacetamide; aromatic hydrocarbons such as benzene, toluene and xylene; and ether compounds such as tetrahydrofuran (THF), 1,4-dioxane, 1,2-dimethoxyethane and diethylene glycol dimethyl ether. N,N-dimethylformamide and 1,4-dioxane are most suited for the availability of a high yield.

The amount of the solvent may range preferably from 1 to 100 times by weight, especially suitably from 5 to 20 times by weight, relative to the sulfonylthiophene compound as the substrate.

The reaction temperature may preferably range from 100 to 150° C. as this temperature range allows the reaction to proceed quickly, although the reaction temperature generally ranges from 0 to 200° C.

The progress of the reaction can be determined based on an analysis by thin layer chromatography or liquid chromatography.

After completion of the reaction, the target product can be obtained by conducting general post-treatment and, if necessary, performing purification.

The sulfonylthiophene compounds according to the present invention can be used in films, electroluminescence devices, semiconductors, cells, solar cells, organic electroluminescence devices, active materials for nonlinear materials, electrodes and the like by utilizing their excellent properties. The sulfonylthiophene compounds themselves have electroconductivity, and therefore, can be used as n-type semiconductors by reducing them with a reductant or through electrochemical doping.

It is to be noted that to the sulfonylthiophene compounds according to the present invention, additives such as heat stabilizers, light stabilizers, fillers and reinforcements can be added as needed upon forming them into films and other formed products.

EXAMPLES

The present invention will hereinafter be described more specifically based on Examples, although the present invention is by no means limited to the following Examples.

The following analyzers and analysis conditions were used in the Examples.

[1] Gas Chromatography (GC)
Model: Hewlett Packard: "HP6800", column: "DB-624" (30 m×0.53 mmφ×3 μm), column temperature: 40 (retained for 0 min.) to 290° C. (retained for 0 min.), 10° C./min. (ramp rate), injection port temperature: 180° C., detector temperature: 250° C., carrier gas: helium, detection method: FID method.

[2] Mass Spectrometry (MASS)
Model: "LX-1000" (JEOL Ltd.), detection method: FAB method.
Model: "JMS-SX102A" (JEOL Ltd.), detection method: FAB method.

[3] $^1$H-NMR
Model: "JNM-A500" (JEOL Ltd.), measurement solvent: $CDCl_3$, $DMSO-d_6$.
Model: "AVANCE 400S" (Bruker), measurement solvent: $CDCl_3$, $DMSO-d_6$.

[4] $^{13}$C-NMR
Model: "JNM-A500" (JEOL Ltd.), measurement solvent: $CDCl_3$, $DMSO-d_6$.
Model: "AVANCE 400S" (Bruker), measurement solvent: $CDCl_3$, $DMSO-d_6$.

[5] IR
Model: "BIORAD FTS-40", KBr tablet method.
Model: "JIR-Winspec 50" (JEOL Ltd.), detection method: neat method.

[6] High-Pressure Liquid Chromatography (LC)
Model: Hewlett Packard: "HP1100", column: "Inertsil ODS-3" (5 μm, 250 mm×4.6 mmφ+guard column 10 mm×4.0 mmφ), column temperature: 40° C., detector: UV 220 nm, eluent: $H_2O/CH_3CN$=graded from 6/4 (retained at 0 min.) to $CH_3CN$ over 15 min (retained for 45 min.), 10° C./min., flow rate: 2.0 mL/min.

[7] Thin-Layer Chromatography (TLC)
"MERCK Silica Gel Plate" was used. Determined at UV 254 nm by heating phosphorus molybdate.

[8] Cyclic Volutammetry (CV)
Model: Electrochemical analyzer "Model 660B" (ALC/HCH Instruments).

[9] Gel Permeation Chromatography (GPC)
Model: TOSOH: "HLC-8220GPC", column: "SHODEX GPC KF-804L"+"SHODEX GPC KF-805L", column temperature: 40° C., detector: UV detector (254 nm) and RI detector, eluent: THF, flow rate: 1.0 mL/min.

[10] Organic EL Luminescence Efficiency Measurement System
Model: "EL1003" (manufactured by Precise Gauge Co., Ltd.)

Example 1

Synthesis of 3,4-bissulfonylthiophenes

[Chemical Formula 88]

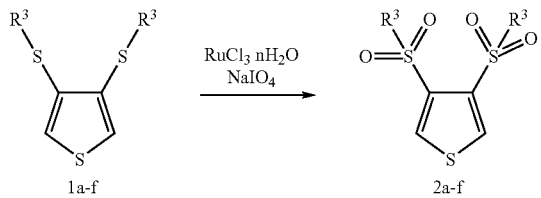

A 3,4-bissulfanylthiophene compound 1a-f and ruthenium (III) chloride n-hydrate (0.05 equivalent, commercial product) were added to a reaction vessel, and were stirred at room temperature until they were fully dissolved. The reaction vessel was cooled, and while retaining the solution at room temperature and paying attention to heat evolution, sodium periodate (4.20 equivalents, commercial product) was added in portions. After completion of the addition, the mixture was stirred further for 5 hours at room temperature. The reaction mixture was extracted with diethyl ether. The organic layer was washed three times with water, and dried over anhydrous sodium sulfate. The solvent was distilled off, and the resultant crude product was purified through a silica gel column (ethyl acetate:hexane=1:2) to afford the corresponding compound 2a-f as a white solid.

TABLE 1

| | | | | 2 | |
| --- | --- | --- | --- | --- | --- |
| Entry | $R^3$ | Solvent | Product | Yield(%) | Rf(TLC)* |
| 1 | $C_4H_9$ | $CH_3CN/H_2O$ | 2a | 83 | 0.5 |
| 2 | $C_6H_{13}$ | acetone/$H_2O$ | 2b | 94 | 0.7 |
| 3 | $C_8H_{17}$ | acetone/$H_2O$ | 2c | 34 | 0.7 |
| 4 | $C_{10}H_{21}$ | acetone/$H_2O$ | 2d | 71 | 0.8 |
| 5 | $CH(CH_3)_2$ | $CH_3CN/H_2O$ | 2e | 85 | 0.4 |
| 6 | Ph | acetone/$H_2O$ | 2f | 53 | 0.2 |

*AcOEt:Hexane = 1:2 as eluent (a) 3,4-Bis(butane-1-sulfonyl)thiophene 2a m/z (EI): 324 (M$^+$) (calculated: 324.05 (M$^+$)).
$^1$H-NMR ($CDCl_3$): 0.91(6H,t,J=7.3 Hz), 1.40-1.46(4H, m), 1.68-1.72(4H,m), 3.55(4H,t,J=8.0 Hz), 8.30(2H,s) ppm.
$^{13}$C-NMR ($CDCl_3$): 13.4(s), 21.3(s), 24.3(s), 55.5(s), 137.5(s), 139.0(s) ppm.

(b) 3,4-Bis(hexane-1-sulfonyl)thiophene 2b m/z (FAB+): 381 (M+H$^+$) (calculated: 381.12 (M+H$^+$)).
$^1$H-NMR (CDCl$_3$): 0.86(6H,t,J=8.0 Hz), 1.25-1.28(8H,m), 1.38-1.41(4H,m), 1.70-1.74(4H,m), 3.55(4H,t,J=8.0 Hz), 8.32(2H,s) ppm.
$^{13}$C-NMR (CDCl$_3$): 13.8(s), 22.1(s), 22.3(s), 27.6(s), 31.0(s), 55.7(s), 137.5(s), 139.0(s) ppm.

(c) 3,4-Bis(octane-1-sulfonyl)thiophene 2c m/z (FAB+): 437 (M+H$^+$) (calculated: 437.19 (M+H$^+$)).
$^1$H-NMR (CDCl$_3$): 0.86(6H,t,J=6.9 Hz), 1.24-1.29(16H,m), 1.37-1.40(4H,m), 1.69-1.74(4H,m), 3.54(4H,t,J=8.0 Hz), 8.30(2H,s) ppm.
$^{13}$C-NMR (CDCl$_3$): 14.0(s), 22.4(s), 22.5(s), 28.0(s), 28.8(s), 31.5(s), 55.7(s), 137.5(s), 138.9(s) ppm.

(d) 3,4-Bis(decane-1-sulfonyl)thiophene 2d m/z (EI): 492 (M$^+$) (calculated: 492.24 (M$^+$)).
$^1$H-NMR (CDCl$_3$): 0.87(6H,t,J=6.4 Hz), 1.24-1.28(24H,m), 1.36-1.40(4H,m), 1.69-1.73(4H,m), 3.54(4H,t,J=8.0 Hz), 8.30(2H,s) ppm.
$^{13}$C-NMR (CDCl$_3$): 14.1(s), 22.4(s), 22.6(s), 28.0(s), 28.9(s), 29.2(s), 29.4(s), 31.8(s), 55.8(s), 137.7(s), 139.0(s) ppm.

(e) 3,4-Bis(propane-2-sulfonyl)thiophene 2e m/z (FAB+): 297 (M+H$^+$) (calculated: 297.03 (M+H$^+$)).
$^1$H-NMR (CDCl$_3$): 1.32(12H,d,J=6.8 Hz), 4.04-4.11(2H,m), 8.30(2H,s) ppm.
$^{13}$C-NMR (CDCl$_3$): 15.0(s), 54.6(s), 136.1(s), 139.5(s) ppm.

(f) 3,4-Bis(benzenesulfonyl)thiophene 2f m/z (FAB+): 365 (M+H$^+$) (calculated: 365.00 (M+H$^+$)).
$^1$H-NMR (CDCl$_3$): 7.52(4H,t,J=7.6 Hz), 7.59(2H,t,J=7.4 Hz), 8.04(4H,d,J=7.4 Hz), 8.38(2H,s) ppm.
$^{13}$C-NMR (CDCl$_3$): 128.4(s), 128.9(s), 133.6(s), 138.4(s), 139.6(s), 140.6(s) ppm.

Example 2

Synthesis of 3,4-bissulfonyl-2,5-bis(tributyl-stannyl)-thiophenes

[Chemical Formula 89]

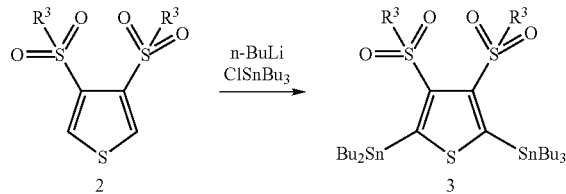

One of the 3,4-bissulfonylthiophenes 2a-f obtained as described above was placed in a reaction vessel, followed by dissolution in THF under a nitrogen atmosphere. The solution was cooled to −78° C. n-Butyl lithium (1.58 M hexane solution, 2.20 equivalents, commercial product) was gradually added dropwise, and at the same temperature, the resultant mixture was stirred for 1 hour. Subsequently, tributylstannyl chloride (2.50 equivalents, commercial product) was added dropwise, followed by stirring for 3 hours. After completion of the reaction, a disodium hydrogenphosphate/sodium dihydrogenphosphate buffer which had been adjusted to pH 7 was added to quench the reaction, and the reaction mixture was extracted with ethyl acetate. The organic layer was washed with saturated brine and dried over anhydrous sodium sulfate. The solvent was eliminated, and the resultant crude product was purified by a silica gel column and PTLC (ethyl acetate:hexane=1:7) to afford the corresponding compound 3a-f in an yellow oil form. The thus-obtained target product was used as it was in the reaction of Example 3.

TABLE 3

| | | | 3 | |
|---|---|---|---|---|
| Entry | R$^3$ | Product | Yield (%) | Rf(TLC)* |
| 1 | C$_4$H$_9$ | 3a | 76 | 0.7 |
| 2 | C$_6$H$_{13}$ | 3b | 91 | 0.8 |
| 3 | C$_8$H$_{17}$ | 3c | 94 | 0.8 |
| 4 | C$_{10}$H$_{21}$ | 3d | 89 | 0.9 |
| 5 | CH(CH$_3$)$_2$ | 3e | 70 | 0.7 |
| 6 | Ph | 3f | 68 | 0.5 |

*AcOEt:Hexane = 1:7 as eluent

(a) 3,4-Bis(butane-1-sulfonyl)-2,5-bis(tributylstannyl)-thiophene 3a m/z (FAB+): 905 (M+H$^+$) (calculated: 905.27 (M+H$^+$)).
$^1$H-NMR (CDCl$_3$): 0.86-0.94(24H,m), 1.19-1.56(40H,m), 17.6(4H,brs), 3.50(4H,brs) ppm.
$^{13}$C-NMR (CDCl$_3$): 13.1(s), 13.5(s), 13.6(s), 21.6(s), 23.7(s), 27.2(s), 28.9(s), 56.1(s), 142.9(s), 165.0(s) ppm.

(b) 3,4-Bis(hexane-1-sulfonyl)-2,5-bis(tributylstannyl)-thiophene 3b m/z (FAB+): 961 (M+H$^+$) (calculated: 961.33 (M+H$^+$)).
$^1$H-NMR (CDCl$_3$): 0.85-0.92(24H,m), 1.19-1.41(36H,m), 1.52-1.60(12H,m), 1.78(4H,brs), 3.52(4H,brs) ppm.
$^{13}$C-NMR (CDCl$_3$): 13.1(s), 13.6(s), 13.9(s), 21.6(s), 22.3(s), 27.2(s), 28.0(s), 28.9(s), 31.1(s), 56.3(s), 142.9(s), 164.9(s) ppm.

(c) 3,4-Bis(octane-1-sulfonyl)-2,5-bis(tributylstannyl)-thiophene 3c m/z (FAB+): 1017 (M+H$^+$) (calculated: 1017.40 (M+H$^+$)).
$^1$H-NMR (CDCl$_3$): 0.84-0.94(24H,m), 1.19-1.39(44H,m), 1.52-1.60(12H,m), 1.78(4H,brs), 3.50(4H,brs) ppm.
$^{13}$C-NMR (CDCl$_3$): 13.1(s), 13.6(s), 14.0(s), 21.6(s), 22.6(s), 27.2(s), 28.3(s), 28.4(s), 28.8(s), 28.9(s), 29.0(s), 31.7(s), 56.3(s), 143.0(s), 164.9(s) ppm.

(d) 3,4-Bis(decane-1-sulfonyl)-2,5-bis(tributylstannyl)-thiophene 3d m/z (FAB+): 1073 (M+H$^+$) (calculated: 1073.46 (M+H$^+$)).
$^1$H-NMR (CDCl$_3$): 0.86-0.94(24H,m), 1.19-1.38(52H,m), 1.52-1.60(12H,m), 1.78(4H,brs), 3.50(4 H,brs) ppm.
$^{13}$C-NMR (CDCl$_3$): 13.1(s), 13.6(s), 14.1(s), 21.7(s), 22.6(s), 27.3(s), 28.3(s), 28.4(s), 28.8(s), 28.9(s), 29.1(s), 29.2(s), 29.3(s), 29.4(s), 31.9(s), 56.4(s), 143.0(s), 165.0(s) ppm.

(e) 3,4-Bis(propane-2-sulfonyl)-2,5-bis(tributylstannyl)-thiophene 3e m/z (FAB+): 877 (M+H$^+$) (calculated: 877.24 (M+H$^+$)).
$^1$H-NMR (CDCl$_3$): 0.89(18H,t,J=7.3 Hz), 0.95(6H,d, J=6.4 Hz), 1.17-1.37(24H,m), 1.44(6H,d,J=6.4 Hz), 1.50-1.60(12H,m), 4.25-4.32(2H,m) ppm.

$^{13}$C-NMR (CDCl$_3$): 13.1(s), 13.6(s), 17.2(s), 27.2(s), 28.8 (s), 54.6(s), 54.7(s), 140.1(s), 166.1(s) ppm.

(f) 3,4-Bis(benzenesulfonyl)-2,5-bis(tributylstannyl)-thiophene 3f m/z (FAB+): 945 (M+H$^+$) (calculated: 945.21 (M+H$^+$)).

$^1$H-NMR (CDCl$_3$): 0.87(18H,t,J=7.3 Hz), 1.18-1.23(12H, m), 1.25-1.35(12H,m), 1.50-1.58(12H,m), 7.40(4H,t,J=7.6 Hz), 7.49(4H,t,J=7.4 Hz), 7.63(4H,d,J=7.2 Hz) ppm.

$^{13}$C-NMR (CDCl$_3$): 13.2(s), 13.6(s), 27.2(s), 28.9(s), 126.4(s), 128.3(s), 132.4(s), 142.0(s), 142.8(s), 166.4(s) ppm.

Example 3

Synthesis of 3',4-bissulfonyl-[2,2'; 5',2"; 5",2'"; 5'", 2""]-quinquethiophenes

[Chemical Formula 90]

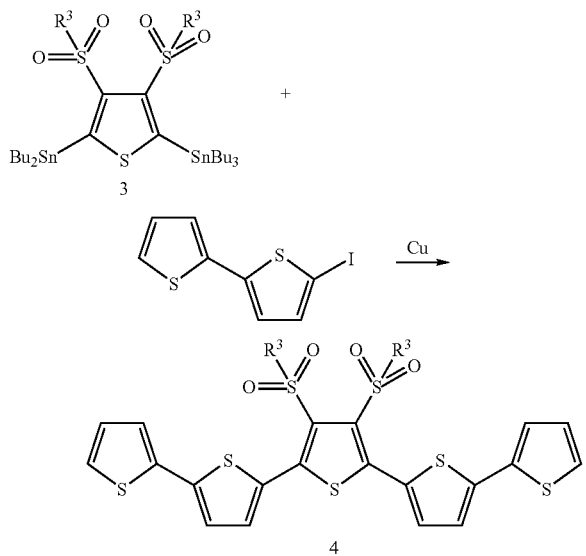

One of the 3,4-bissulfonyl-2,5-bis(tributylstannyl)-thiophenes 3a-f obtained as described above and copper(I) chloride (2.2 equivalents, commercial product) were placed in a reaction vessel. They were dissolved in THF under a nitrogen atmosphere, followed by the addition of 2-iodobithiophene (2.1 equivalents) at room temperature. Subsequently, the reaction mixture was heated, and under reflux conditions, was stirred for 20 hours. After the reaction, the reaction mixture was allowed to cool down to room temperature. Subsequent to the addition of an aqueous solution of hydrochloric acid, the mixture was extracted with ethyl acetate. The organic layer was washed with saturated brine and dried over anhydrous sodium sulfate. The solvent was distilled off under reduced pressure, and the resultant crude product was purified through a silica gel column (ethyl acetate:hexane=1:2) and further by GPC to afford the corresponding compound 4a-f in an yellow amorphous form.

TABLE 4

| | | | 4 | |
|---|---|---|---|---|
| Entry | R$^3$ | Product | Yield (%) | Rf(TLC)* |
| 1 | C$_4$H$_9$ | 4a | 83 | 0.6 |
| 2 | C$_6$H$_{13}$ | 4b | 68 | 0.7 |
| 3 | C$_8$H$_{17}$ | 4c | 74 | 0.8 |
| 4 | C$_{10}$H$_{21}$ | 4d | 69 | 0.8 |
| 5 | CH(CH$_3$)$_2$ | 4e | 87 | 0.6 |
| 6 | Ph | 4f | 78 | 0.4 |

*AcOEt:Hexane = 1:2 as eluent (a) 3",4"-Bis(butane-1-sulfonyl)-[2,2'; 5',2"; 5",2'"; 5'",2""]-quinquethiophene 4a m/z (FAB$^+$): 652 (M$^+$) (calculated: 652.00 (M$^+$)).
$^1$H-NMR (CDCl$_3$): 0.96(6H,t,J=7.3 Hz), 1.45-1.54(4H, m), 1.84-1.92(4H,m), 3.70(4H,t,J=7.9 Hz), 7.03(2H,dd,J=3.6 Hz, 1.5 Hz), 7.14(2H,d,J=3.8 Hz), 7.17(2H,d,J=3.8 Hz), 7.26 (2H,d,J=5.1 Hz), 7.31(2H,d,J=3.8 Hz) ppm.
$^{13}$C-NMR (CDCl$_3$): 13.5(s), 21.6(s), 23.5(s), 57.2(s), 123.6(s), 124.9(s), 125.5(s), 128.0(s), 128.5(s), 131.7(s), 135.7(s), 136.0(s), 141.5(s), 144.8(s) ppm.

(b) 3",4"-Bis(hexane-1-sulfonyl)-[2,2'; 5',2"; 5",2'"; 5'",2""]-quinquethiophene 4b m/z (FAB+): 709 (M+H$^4$) (calculated: 709.07 (M+H$^+$)).
$^1$H-NMR(CDCl$_3$): 0.88(6H,t,J=6.9Hz), 1.30-1.33(8H,m), 1.43-1.45(4H,m), 1.87-1.89(4H,m), 3.69(4H,t,J=7.9Hz), 7.03(2H,dd,J=0.9, 3.9Hz), 7.14(2H,d,J=3.8Hz), 7.17(2H,d, J=3.8Hz), 7.21(2H,d,J=3.6Hz), 7.27(2H,d,J=5.1Hz) ppm.
$^{13}$C-NMR (CDCl$_3$): 13.9(s), 21.5(s), 22.3, 27.9(s), 31.1(s), 57.3(s), 123.6(s), 124.6(s), 125.5(s), 127.9(s), 128.5(s), 131.7 (s), 135.8(s), 135.9(s), 141.5(s), 144.7(s) ppm.

(c) 3',4"-Bis(octane-1-sulfonyl)-[2,2'; 5',2"; 5",2'"; 5'",2""]-quinquethiophene 4c m/z (FAB$^+$): 765 (M+H$^+$) (calculated: 765.14 (M+H$^+$))
$^1$H-NMR (CDCl$_3$): 0.86(6H,t,J=6.8 Hz), 1.25-1.30(16H, m), 1.43-1.46(4H,m), 1.87-1.91(4H,m), 3.69(4H,t,J=7.9 Hz), 7.02(2H,dd,J=5.0 Hz, 3.7 Hz), 7.13(2H,d,J=3.8 Hz), 7.17 (2H,d,J=3.8 Hz), 7.21(2H,d,J=3.6 Hz), 7.26(2H,d,J=5.1 Hz) ppm.
$^{13}$C-NMR (CDCl$_3$): 14.0(s), 21.5(s), 22.5(s), 28.3(s), 28.9 (s), 31.6(s), 57.2(s), 123.6(s), 124.6(s), 125.5(s), 127.9(s), 128.4(s), 131.7(s), 135.7(s), 135.9(s), 141.5(s), 144.7(s) ppm.

(d) 3',4"-Bis(decane-1-sulfonyl)-[2,2'; 5',2"; 5",2'"; 5'",2""]-quinquethiophene 4d m/z (FAB$^+$): 821 (M+H$^+$) (calculated: 821.20 (M+H$^+$)).
$^1$H-NMR (CDCl$_3$): 0.87(6H,t,J=6.9 Hz), 1.25-1.31(24H, m), 1.40-1.50(4H,m), 1.83-1.92(4H,m), 3.68(4H,t,J=7.9 Hz), 7.04-7.05(2H,m), 7.15(2H,d,J=3.8 Hz), 7.18(2H,d,J=3.8 Hz), 7.22(2H,dd,J=3.6 Hz, 1.1 Hz), 7.28(2H,dd,J=5.1 Hz, 1.1 Hz) ppm.
$^{13}$C-NMR (CDCl$_3$): 14.1(s), 21.6(s), 22.6(s), 28.3(s), 29.0 (s), 29.2(s), 29.2(s), 29.4(s), 31.8(s), 57.3(s), 123.6(s), 124.7 (s), 125.5(s), 127.9(s), 128.5(s), 131.7(s), 135.8(s), 136.0(s), 141.5(s), 144.7(s) ppm.

(e) 3",4"-Bis(propane-2-sulfonyl)-[2,2'; 5',2"; 5",2'"; 5'",2""]-quinquethiophene 4e m/z (FAB$^+$): 624 (M+H$^+$) (calculated: 624.98 (M+H$^+$)).
$^1$H-NMR (CDCl$_3$): 1.33(12H,d,J=6.9 Hz), 4.25-4.32(2H, m), 7.00-7.03(2H,m), 7.12(2H,d,J=3.8 Hz), 7.21-7.22(4H, m), 7.24-7.26(2H,m) ppm.

$^{13}$C-NMR (CDCl$_3$): 15.1(s), 55.5(s), 123.2(s), 124.5(s), 125.4(s), 127.9(s), 128.0(s), 132.5(s), 133.3(s), 136.0(s), 141.3(s), 145.9(s) ppm.

(f) 3'',4''-Bis(benzenesulfonyl)-[2,2'; 5',2''; 5'',2'''; 5''',2'''']-quinquethiophene 4f m/z (FAB$^+$): 692 (M+H$^+$) (calculated: 692.95 (M+H$^+$)).
$^1$H-NMR (CDCl$_3$): 7.03(2H,dd,J=4.8 Hz, 3.9 Hz), 7.08 (2H,d,J=3.8 Hz), 7.16(2H,d,J=3.6 Hz), 7.18(2H,d,J=3.8 Hz), 7.27(2H,t,J=4.7 Hz), 7.41(4H,t,J=7.8 Hz), 7.52(2H,dd,J=7.3 Hz, 0.4 Hz), 7.83(2H,d,J=7.7 Hz) ppm.
$^{13}$C-NMR (CDCl$_3$): 123.7(s), 124.7(s), 125.6(s), 127.6(s), 128.0(s), 128.5(s), 132.9(s), 133.0(s), 135.9(s), 137.2(s), 141.9(s), 142.0(s), 143.7(s) ppm.

Example 4

Synthesis of 3',4'-bis(decane-1-sulfonyl)-[2,2'; 5',2'']-terthiophene and 3''',4'''-bis(decane-1-sulfonyl)-[2,2'; 5',2''; 5'',2'''; 5''',2''''; 5'''',2'''''; 5''''',2'''''']-septithiophene

[Chemical Formula 91]

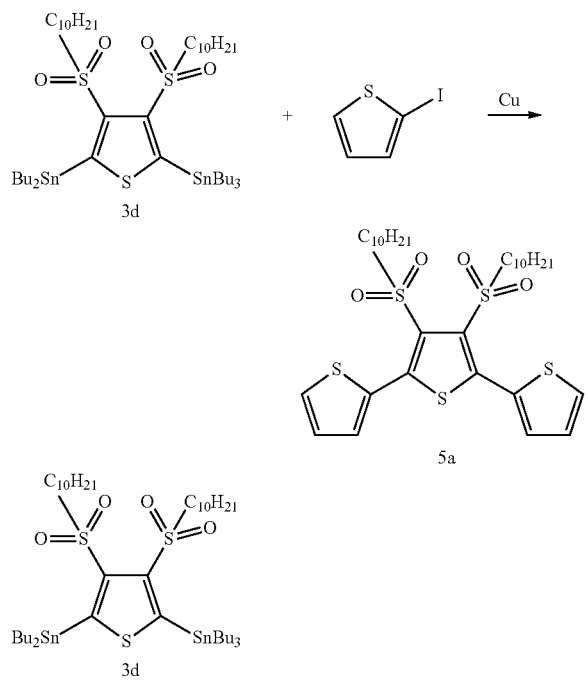

Synthesis was conducted in a similar manner as in Example 3.

(a) 3',4'-bis(decane-1-sulfonyl)[2,2'; 5',2'']-terthiophene 5a m/z (FAB$^+$) 657 (M+H$^+$) (calculated: 657.23 (M+H$^+$)).
$^1$H-NMR (CDCl$_3$): 0.88(6H,t,J=6.8 Hz), 1.26-1.30(24H, m), 1.39-1.42(4H,m), 1.82-1.88(4H,m), 3.66(4H,t,J=8.0 Hz), 7.09(2H,dd,J=5.1 Hz, 3.6 Hz), 7.25(2H,dd,J=3.7 Hz, 1.3 Hz), 7.51(2H,dd,J=5.1 Hz, 1.2 Hz) ppm.
$^{13}$C-NMR (CDCl$_3$): 14.0(s), 21.5(s), 22.6(s), 28.3(s), 29.0 (s), 29.2(s), 29.4(s), 31.8(s), 57.3(s), 127.1(s), 129.2(s), 130.1 (s), 130.8(s), 136.0(s), 145.2(s) ppm.

(b) 3''',4'''-bis(decane-1-sulfonyl)-[2,2'; 5',2''; 5'', 2'''; 5''',2''''; 5'''',2'''''; 5''''',2'''''']-septithiophene 5b m/z (FAB$^+$): 984 (M$^+$) (calculated: 984.17 (M$^+$)).
$^1$H-NMR (CDCl$_3$): 0.86(6H,t,J=6.8 Hz), 1.24-1.32(24H, m), 1.41-1.49(4H,m), 1.85-1.93(4H,m), 3.69(4H,t,J=7.9 Hz), 7.03(2H,dd,J=1.5, 3.6 Hz), 7.09-7.14(6H,m), 7.18-7.20(4H, m), 7.24(2H,dd,J=1.1, 4.0 Hz) ppm.
$^{13}$C-NMR (CDCl$_3$): 14.0(s), 21.5(s), 22.6(s), 28.3(s), 29.0 (s), 29.2(s), 29.3(s), 29.4(s), 31.8(s), 57.3(s), 123.5(s), 124.0 (s), 124.3(s), 124.8(s), 125.2(s), 127.9(s), 128.5(s), 131.8(s), 134.5(s), 135.8(s), 136.6(s), 137.4(s), 141.2(s), 144.6(s) ppm.

Example 5

Synthesis of 3'', 3''',4'',4'''-tetrakis(decane-1-sulfonyl)-[2,2'; 5',2''; 5'',2'''; 5''',2''''; 5'''',2''''']-sexithiophene

[Chemical Formula 92]

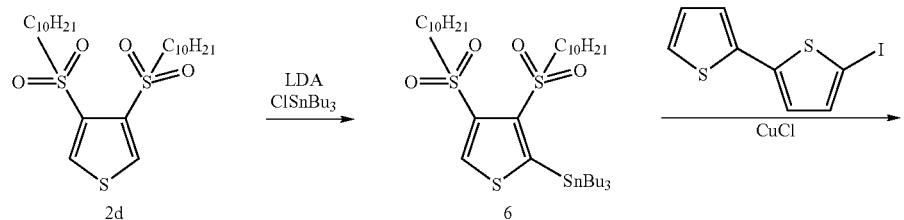

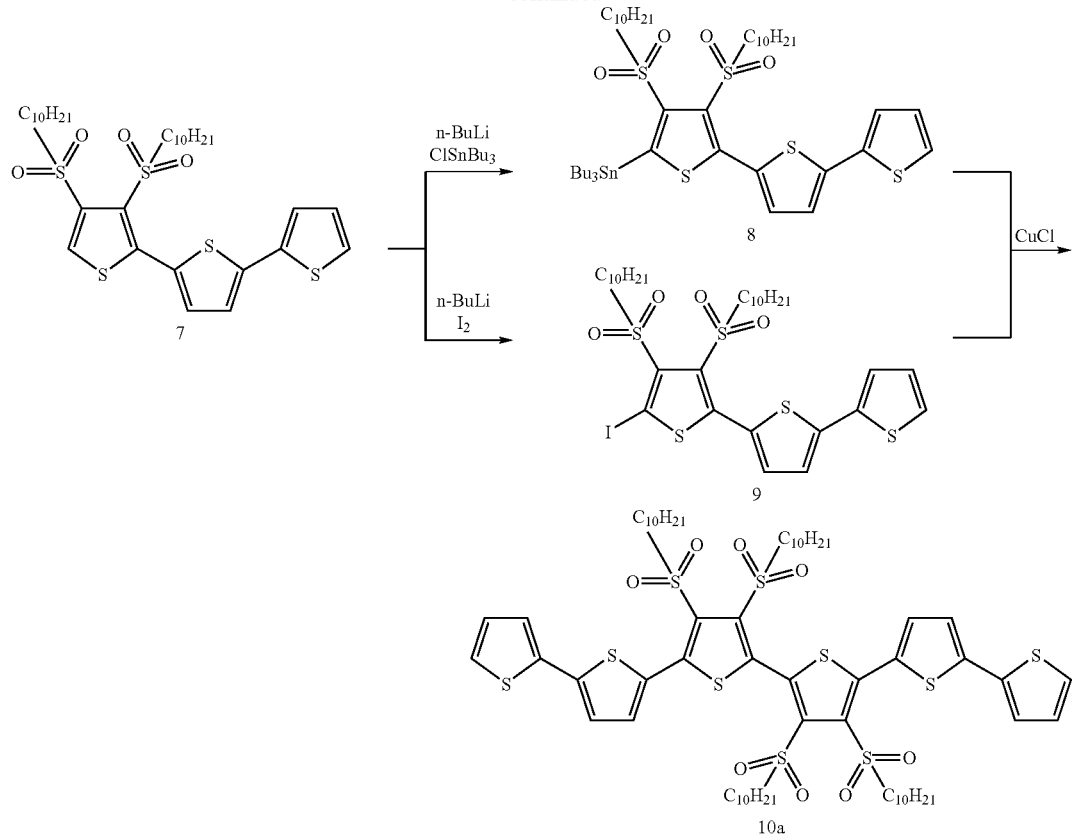

Following the scheme of the above diagram, synthesis was conducted. That is, 3,4-bis(decane-1-sulfonyl)thiophene 2d was converted into 3,4-bis(decane-1-sulfonyl)-[2,2'; 5',2"]-terthiophene 7. Subsequently, monotributylstannylation and monoiodation were conducted to synthesize the compounds 8 and 9, respectively. Those compounds were coupled with copper(I) chloride to derive 3',3'", 4",4'"-tetrakis(decane-1-sulfonyl)-[2,2'; 5',2"; 5",2'"; 5'",2""; 5"",2""']-sexithiophene 10a.

Specifically, the synthesis was conducted under the following conditions.

3,4-Bis(decane-1-sulfonyl)thiophene 2d was placed in a reaction vessel, followed by dissolution in THF under an nitrogen atmosphere. The solution was cooled to −78° C. To the solution, n-butyl lithium (1.58 M hexane solution, 1.00 equivalent, commercial product) was gradually added dropwise, and at the same temperature, the resultant mixture was stirred for 1 hour. Subsequently, tributylstannyl chloride (1.10 equivalents, commercial product) was added dropwise, followed by stirring for 3 hours. After completion of the reaction, a disodium hydrogenphosphate/sodium dihydrogenphosphate buffer which had been adjusted to pH 7 was added to quench the reaction, and the reaction mixture was extracted with ethyl acetate. The organic layer was washed with saturated brine and dried over anhydrous sodium sulfate. The solvent was eliminated, and the resultant crude product was purified by a silica gel column and PTLC to afford the compound 6. The thus-obtained compound 6 was provided as it was for the subsequent reaction.

The above-obtained compound 6 and copper(I) chloride (1.10 equivalents, commercial product) were placed in a reaction vessel. They were dissolved in THF under a nitrogen atmosphere, followed by the addition of 2-iodobithiophene (1.10 equivalents) at room temperature. Subsequently, the reaction mixture was heated, and under reflux conditions, was stirred for 20 hours. After the reaction, the reaction mixture was allowed to cool down to room temperature. Subsequent to the addition of an aqueous solution of hydrochloric acid, the mixture was extracted with ethyl acetate. The organic layer was washed with saturated brine and dried over anhydrous sodium sulfate. The solvent was distilled off under reduced pressure, and the resultant crude product was purified through a silica gel column and further by GPC to afford the compound 7. The thus-obtained compound 7 was provided as it was for the subsequent reaction.

The above-obtained compound 7 was placed in a reaction vessel, followed by dissolution in THF under an nitrogen atmosphere. The solution was cooled to −78° C. To the solution, n-butyl lithium (1.58 M hexane solution, 1.00 equivalent, commercial product) was gradually added dropwise, and at the same temperature, the resultant mixture was stirred for 1 hour. Subsequently, tributylstannyl chloride (1.10 equivalents, commercial product) was added dropwise, followed by stirring for 3 hours. After completion of the reaction, a disodium hydrogenphosphate/sodium dihydrogenphosphate buffer which had been adjusted to pH 7 was added to quench the reaction, and the reaction mixture was extracted with ethyl acetate. The organic layer was washed with saturated brine and dried over anhydrous sodium sulfate. The solvent was eliminated, and the resultant crude product was purified by a silica gel column and PTLC to afford the compound 8. The thus-obtained compound 8 was provided as it was for the subsequent reaction.

The above-obtained compound 7 was dissolved in THF, and the resultant solution was cooled to −78° C. To the solution, n-butyl lithium (1.58 M hexane solution, 1.00 equivalent, commercial product) was gradually added dropwise, and at the same temperature, the resultant mixture was stirred for 3 hours. Subsequently, a solution of iodine (1.10 equivalent, commercial product) in THF was added dropwise, followed by stirring for 1 hour. The temperature of the reaction mixture was then allowed to rise to room temperature, followed by further stirring for 13 hours. After completion of the reaction, sodium thiosulfate was added, and the reaction mixture was extracted with ethyl acetate. The organic layer was washed with an aqueous solution of sodium thiosulfate and saturated brine and was then dried over anhydrous sodium sulfate. The solvent was eliminated, and the resultant crude product was purified through a silica gel column to afford the compound 9. The thus-obtained compound 9 was provided as it was for the subsequent reaction.

The above-obtained compound 8 and copper(I) chloride (1.00 equivalent, commercial product) were placed in a reaction vessel. They were dissolved in THF under a nitrogen acetate. The organic layer was washed with saturated brine and dried over anhydrous sodium sulfate. The solvent was distilled off under reduced pressure, and the resultant crude product was purified through a silica gel column and further by GPC to afford the compound 10a as a yellow oil.

m/z (FAB+): 1311 (M+H$^+$) (calculated: 1311.43 (M+H$^+$)).

$^1$H-NMR (CDCl$_3$): 0.85-0.88(12H,m), 1.24-1.45(56H,m), 1.79-1.89(8H,m), 3.50-3.84(8H,m), 7.04(2H,dd,J=5.0 Hz, 3.7 Hz), 7.16(2H,d,J=3.8 Hz), 7.23(2H,d,J=2.9 Hz), 7.26(2H, d,J=3.8 Hz), 7.28(2H,d,J=5.1 Hz) ppm.

$^{13}$C-NMR (CDCl$_3$): 14.0(s), 21.3(s), 21.7(s), 22.6(s), 28.2 (s), 28.3(s), 29.0(s), 29.1(s), 29.2(s), 29.2(s), 29.4(s), 31.8(s), 57.0(s), 57.2(s), 123.6(s), 124.7(s), 125.7(s), 127.4(s), 128.0 (s), 132.7(s), 133.8(s), 135.9(s), 139.4(s), 142.1(s), 146.8(s) ppm.

Example 6

Synthesis of 3",4"-bis(decane-1-sulfonyl)-3''',4'''-bis (decylsulfanyl)[2,2'; 5',2"; 5",2'''; 5''',2''''; 5'''',2''''']-sexithiophene

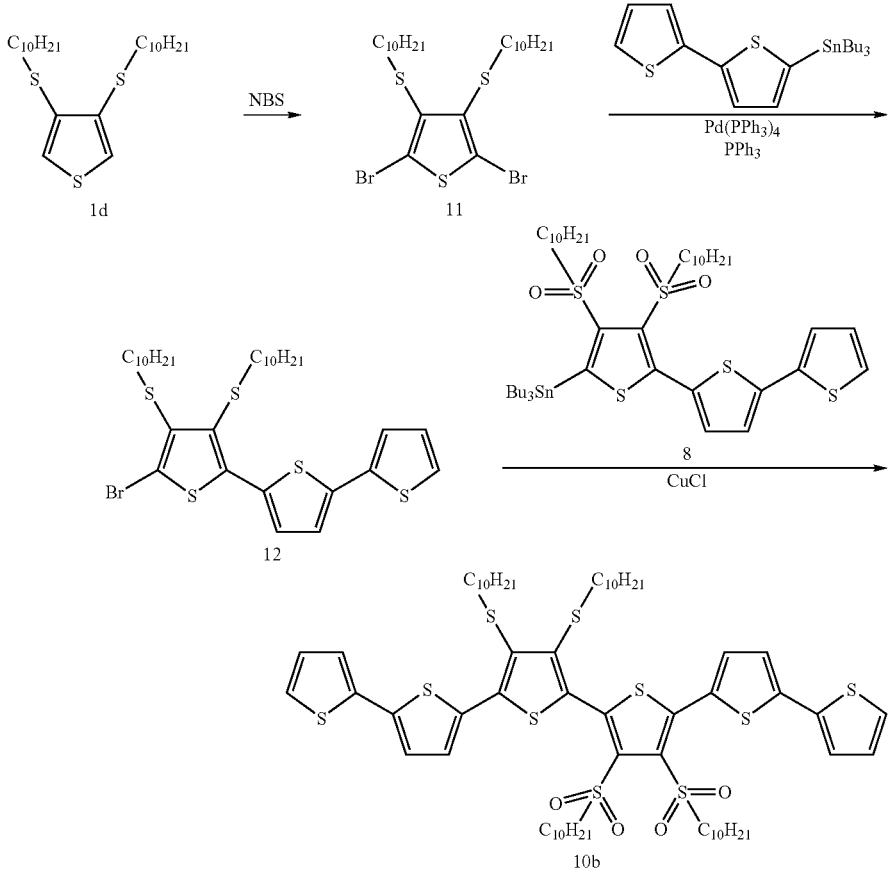

[Chemical Formula 93]

atmosphere, followed by the addition of the above-obtained compound 9(1.00 equivalent) at room temperature. Subsequently, the reaction mixture was heated, and under reflux conditions, was stirred for 20 hours. After the reaction, the reaction mixture was allowed to cool down to room temperature. Subsequent to the addition of an aqueous solution of hydrochloric acid, the mixture was extracted with ethyl Following the scheme of the above diagram, synthesis was conducted. That is, 3,4-bis(decylsulfanyl)thiophene 1d was converted into 2,5-dibromo-3,4-bis(decane-1-sulfanyl)-thiophene 11 by dibromination. 2,5-Dibromo-3,4-bis(decane-1-sulfanyl)thiophene was subsequently converted into 5-bromo-3,4-bis(decane-1-sulfanyl)-[2,2'; 5',2"]-terthiophene 12 by the Stille coupling. Using copper(I) chloride, 5-bromo-3,4-bis(decane-1-sulfanyl)-[2,2'; 5',2'']-terthiophene was coupled with the compound 8 to derive 3'',4''-bis(decane-1-sulfonyl)-3''',4'''-bis(decylsulfanyl)-[2,2'; 5',2''; 5'',2'''; 5''',2''''; 5'''',2''''']-sexithiophene 10b.

Specifically, the synthesis was conducted under the following conditions. 3,4-Bis(decylsulfanyl)thiophene 1d was dissolved in a 1:1 mixed solvent of chloroform and acetic acid, followed by the addition of commercial N-bromosuccinimide (2.10 equivalents, commercial product) at room temperature. Subsequently, the reaction mixture was stirred at room temperature for 24 hours. After the reaction, an aqueous solution of sodium thiosulfate was added, followed by extraction with methylene chloride. The solvent was distilled off under reduced pressure, and the resultant crude product was purified through a silica gel column to afford the compound 11. The thus obtained compound 11 was provided as it was for the subsequent reaction.

Dissolved at room temperature in toluene were the above-obtained compound 11, tetrakistriphenylphosphine palladium (0.08 equivalent, commercial product), and triphenylphosphine (0.32 equivalent, commercial product). To the resultant solution, 2-tributylstannylbithiophene (1.00 equivalent) was added at room temperature. Subsequently, the reaction mixture was heated, and under reflux conditions, was stirred for 2 hours. After the reaction, the reaction mixture was allowed to cool down to room temperature, and an aqueous solution of potassium fluoride was added, followed by stirring for 1 hour. The resulting solid matter was filtered off by "Celite", and the filtrate was extracted with ethyl acetate. The organic layer was washed with saturated brine and dried over anhydrous sodium sulfate. The solvent was distilled off, and the resultant crude product was purified by a PTLC plate to afford the compound 12. The thus-obtained compound 12 was provided as it was for the subsequent reaction.

The above-obtained compound 12 and copper(I) chloride (1.00 equivalent, commercial product) were placed in a reaction vessel. They were dissolved in THF under a nitrogen atmosphere, followed by the addition of the above-obtained compound 8(1.00 equivalent) at room temperature. Subsequently, the reaction mixture was heated, and under reflux conditions, was stirred for 20 hours. After the reaction, the reaction mixture was allowed to cool down to room temperature. Subsequent to the addition of an aqueous solution of hydrochloric acid, the mixture was extracted with ethyl acetate. The organic layer was washed with saturated brine and dried over anhydrous sodium sulfate. The solvent was distilled off under reduced pressure, and the resultant crude product was purified through a silica gel column and further by GPC to afford the compound 10b as a yellow solid.

m/z (FAB+): 1247 (M+H$^+$) (calculated: 1247.45 (M+H$^+$)).

$^1$H-NMR (CDCl$_3$): 0.84-0.89(12H,m), 1.22-1.42(56H,m), 1.42-1.59(4H,m), 1.85-1.87(4H,m), 2.90(4H,dd,J=12.3 Hz, 7.2 Hz), 3.66(2H,t,J=7.9 Hz), 3.79(2H,t,J=7.9 Hz), 7.04-7.06 (2H,m), 7.12(1H,d,J=3.9 Hz), 7.16(1H,d,J=3.8 Hz), 7.21-7.27(5H,m), 7.34-7.35(2H,d,J=3.8 Hz) ppm.

$^{13}$C-NMR (CDCl$_3$): 14.1(s), 21.3(s), 21.6(s), 22.7(s), 28.3 (s), 28.4(s), 28.7(s), 28.8(s), 29.1(s), 29.1(s), 29.2(s), 29.3(s), 29.3(s), 29.5(s), 29.5(s), 29.6(s), 29.7(s), 31.8(s), 31.9(s), 31.9(s), 36.3(s), 36.9(s), 56.9(s), 57.3(s), 123.1(s), 123.6(s), 124.0(s), 124.7(s), 124.9(s), 125.5(s), 127.6(s), 127.9(s), 128.0(s), 128.4(s), 129.6(s), 130.6(s), 132.0(s), 133.4(s), 134.8(s), 136.0(s), 136.9(s), 138.9(s), 139.2(s), 141.7(s), 142.5(s), 143.2(s), 146.0(s) ppm.

Example 7

Synthesis of 3'',4'',3''''''',4'''''''-tetrakis(decane-1-sulfonyl)-3'''',4''''''-bis(decylsulfanyl)-[2,2'; 5',2''; 5'',2'''; 5''',2''''; 5'''',2'''''; 5''''',2''''''; 5'''''',2'''''''; 5''''''',2'''''''']-novithiophene 13a and 3'',4'',3''''''',4'''''''-tetrakis (decane-1-sulfonyl)-3'''',4''''''-bis(decylsulfanyl)-[2,2'; 5',2''; 5'',2'''; 5''',2''''; 5'''',2'''''; 5''''',2''''''; 5'''''',2'''''''; 5''''''',2''''''''; 5'''''''',2''''''''']-undecithiophene 13b

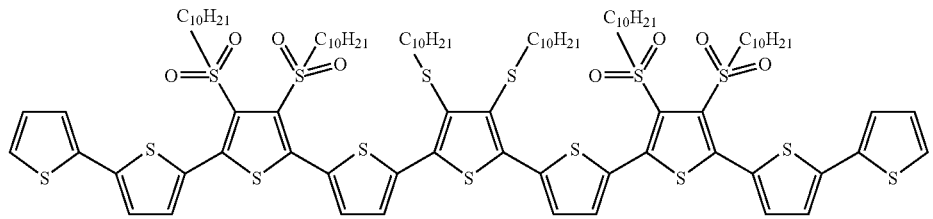

13a

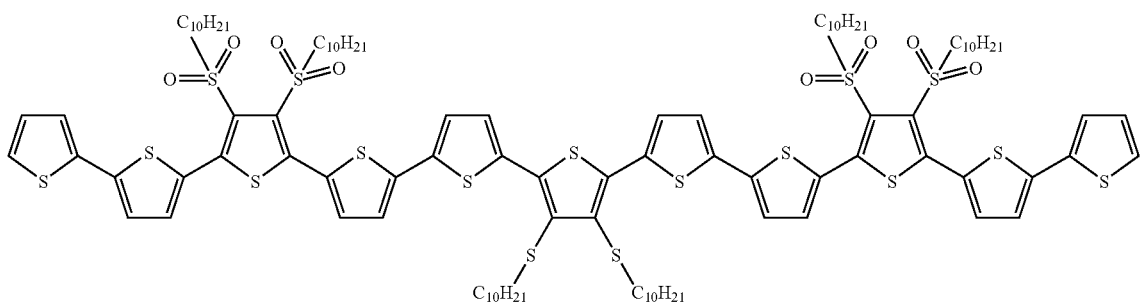

13b

Synthesis was conducted in a similar manner as in Examples 1 to 6. That is, 3,4-bis(decylsulfanyl)-thiophene 1d and 3,4-bis(decane-1-sulfonyl)thiophene 2d were converted by halogenation, tributylstannylation and coupling into 3',4', 3'''',4''''-tetrakis(decane-1-sulfonyl)-3'''',4''''-bis(decylsulfanyl)-[2,2'; 5',2''; 5'',2'''; 5''',2''''; 5'''',2''''';-5''''', 2''''''; 5''''''', 2'''''''; 5''''''',2'''''''']-novithiophene 13a and 3'',4'',3''''''',4'''''''-tetrakis(decane-1-sulfonyl)-3'''',4''''-bis(decylsulfanyl)-[2, 2'; 5',2''; 5'',2'''; 5''',2''''; 5'''',2''''';-5''''',2''''''; 5'''''',2'''''''; 5''''''', 2'''''''';  5'''''''',2''''''''';  5''''''''',2'''''''''']-undecithiophene 13b (a) 3'',4'',3''''''',4'''''''-tetrakis(decane-1-sulfonyl)-3'''', 4''''-bis(decylfanyl)-[2,2'; 5',2''; 5'',2'''; 5''',2''''; 5'''',2''''';-5''''',2''''''; 5'''''',2'''''''; 5''''''',2'''''''']-novithiophene 13a m/z (FAB+): 1901 (M+H$^+$) (calculated: 1901.65 (M+H$^+$)).
$^1$H-NMR (CDCl$_3$): 0.84-0.89(18H,m), 1.22-1.46(84H,m), 1.57-1.61(4H,m), 1.88-1.93(8H,m), 2.89(4H,t,J=7.4 Hz), 3.67-3.75(8H,m), 7.04(2H,dd,J=5.1 Hz, 3.6 Hz), 7.15(2H,d, J=3.8 Hz), 7.19(2H,d,J=3.8 Hz), 7.22-7.23(4H,m), 7.28(2H, dd,J=5.1 Hz, 1.1 Hz), 7.41(2H,d,J=4.2 Hz) ppm.
$^{13}$C-NMR (CDCl$_3$): 14.1(s), 21.6(s), 21.7(s), 22.6(s), 28.3 (s), 28.5(s), 28.9(s), 29.0(s), 29.1(s), 29.2(s), 29.2(s), 29.3(s), 29.3(s), 29.4(s), 29.5(s), 29.5(s), 31.8(s), 37.1(s), 57.3(s), 57.5(s), 123.6(s), 124.7(s), 125.5(s), 126.2(s), 127.9(s), 128.5 (s), 130.1(s), 131.4(s), 131.8(s), 133.6(s), 135.9(s), 136.0(s), 136.0(s), 137.7(s), 139.2(s), 141.6(s), 144.9(s) ppm.

(b) 3'',4'',3''''''',4'''''''-tetrakis(decane-1-sulfonyl)-3'''',4''''-bis(decylsulfanyl)-[2,2'; 5',2''; 5'',2'''; 5''', 2''''; 5'''',2''''';-5''''',2''''''; 5'''''',2'''''''; 5''''''', 2''''''''; 5'''''''',2''''''''';  5''''''''',2'''''''''']-undecithiophene 13b m/z (FAB+): 2065 (M+H$^+$) (calculated: 2065.62 (M+H$^+$)).
$^1$H-NMR (CDCl$_3$): 0.84-0.89(18H,m), 1.23-1.45(84H,m), 1.57-1.63(4H,m), 1.88-1.90(8H,m), 2.90(4H,t,J=7.4 Hz), 3.67-3.72(8H,m), 7.04(2H,dd,J=5.1 Hz, 3.7 Hz), 7.14-7.23 (12H,m), 7.28(2H,dd,J=5.1 Hz, 1.1 Hz), 7.38(2H,d,J=3.9 Hz) ppm.
$^{13}$C-NMR (CDCl$_3$): 14.1(s), 21.6(s), 22.6(s), 28.3(s), 28.9 (s), 29.1(s), 29.2(s), 29.3(s), 29.3(s), 29.5(s), 29.5(s), 31.8(s), 37.1(s), 57.3(s), 123.7(s), 123.8(s), 124.7(s), 125.5(s), 128.0 (s), 128.5(s), 128.9(s), 131.8(s), 131.9(s), 132.9(s), 135.4(s), 135.9(s), 136.0(s), 137.0(s), 137.6(s), 141.3(s), 141.6(s), 144.7(s), 144.8(s) ppm.

Example 8

Synthesis of poly{3,4-bis(octane-1-sulfonyl)-[2,2']-bithiophene} by Chemical Polymerization

[Chemical Formula 95]

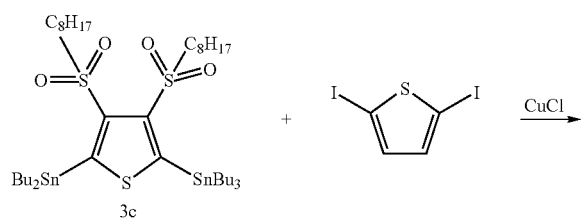

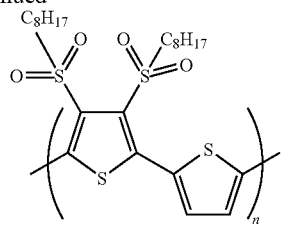

3,4-Bis(octane-1-sulfonyl)-2,5-bis(tributylstannyl)-thiophene 3c (163 mg; 0.231 mmol) and 2,5-diiodothiophene (77.8 mg; 0.231 mmol) were dissolved in N,N-dimethylformamide (2 mL), followed by the addition of commercial copper(I) chloride (96.0 mg; 0.970 mmol). The resulting mixture was stirred at room temperature for 6 hours to prepare a dispersion of an orange color. A portion of the dispersion was sampled, washed thoroughly with dimethylformamide (1 mL) and THF (1 mL), filtered by using a syringe and a chromatographic disk, and then analyzed by GPC. As a result, a polymer peak of Mw=1800 or so was observed.

Example 9

Synthesis of poly{3'',4''-bis(decane-1-sulfonyl)-[2,2'; 5',2''; 5'',2'''; 5''',2'''']-quinquethiophene} by Electrolytic Polymerization Using a three-electrode beaker cell equipped with a platinum mesh counter electrode, electrolytic oxidation was conducted by the constant potential electrolysis method to conduct the synthesis of the target compound. Employed was a solution of 3'',4''-bis(decane-1-sulfonyl)-[2,2'; 5',2''; 5'',2'''; 5''',2'''']-quinquethiophene 4d (20.5 mg) and commercial tetrabutylammonium perchlorate (863.4 mg) in acetonitrile (25 mL). Using a platinum plate (1.0 cm$^2$ per side) as a test electrode substrate and Ag/Ag$^+$ as a reference electrode, electrolytic polymerization was conducted for 600 seconds while controlling the potential range within 1000 mV by an electrochemical measurement system (BAS, Inc.). As a result, a dark blue (changed to an orange color after a short time) solid polymer deposited as the target compound on the electrode.
<Polymerized Product>
IR(KBr): 529, 668, 802, 1122, 1143, 1319, 2853, 2923 cm$^{-1}$.
<Starting Material>

3',4''-bis(decane-1-sulfonyl)-[2,2'; 5',2''; 5'',2'''; 5''', 2'''']-quinquethiophene 4d IR(KBr): 479, 523, 565, 598, 612, 627, 702, 782, 797, 808, 838, 957, 1139, 1208, 1234, 1271, 1314, 1334, 1410, 1421, 1470, 1650, 1657, 1698, 2851, 2920, 3747 cm$^{-1}$.

Example 10

Cyclic Volutammetry (CV) Measurement

Figure 2:
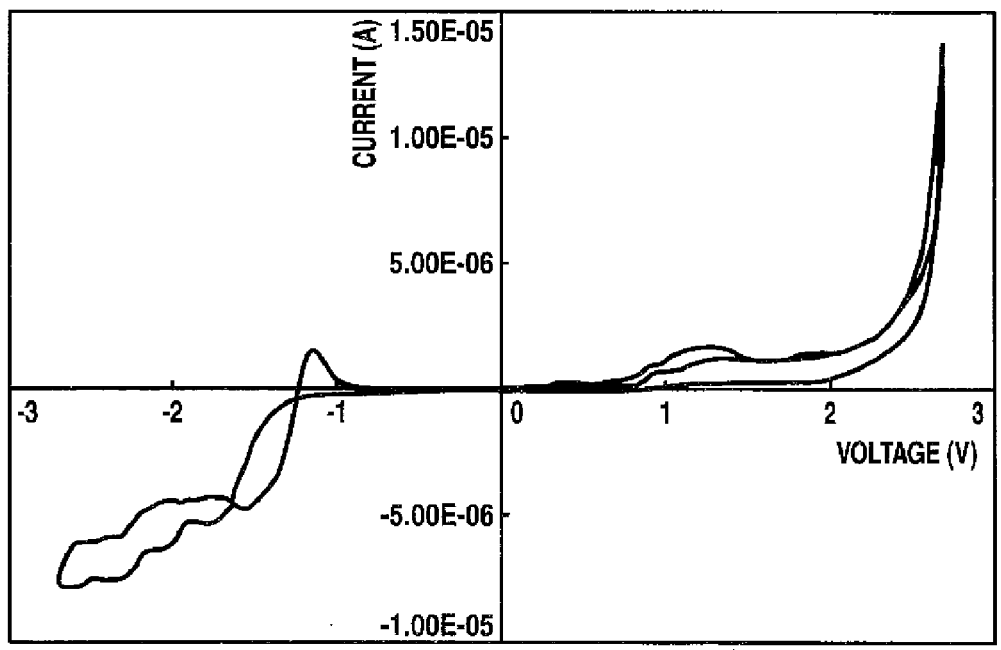
Figure 3:
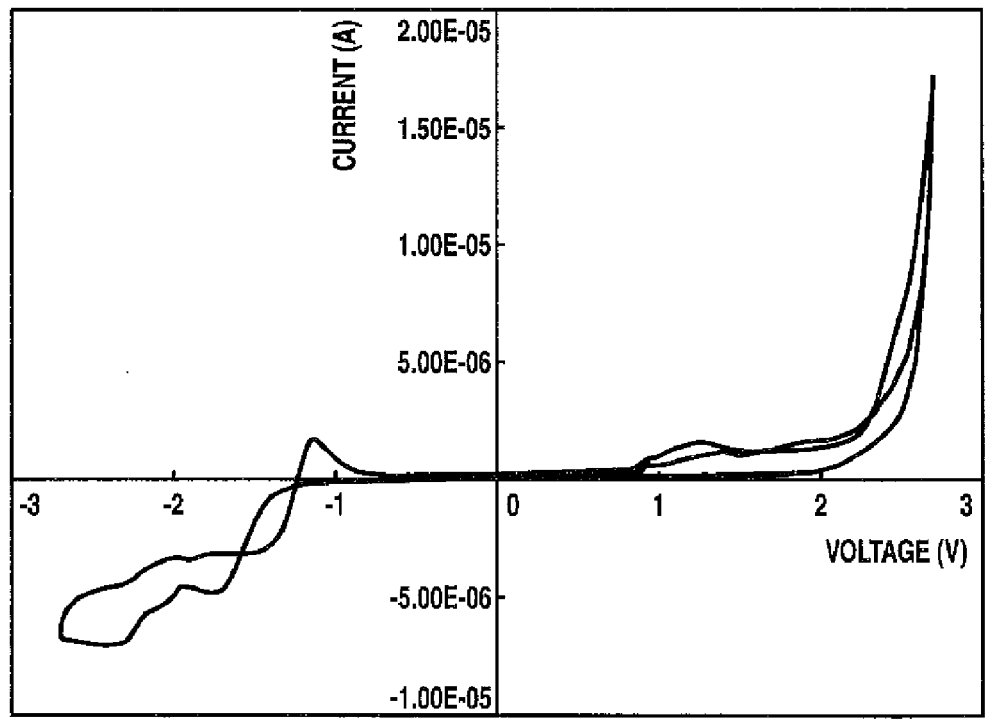
FIG. 3 is a diagram showing cyclic volutammetry of a thiophene derivative 4d.
Figure 4:
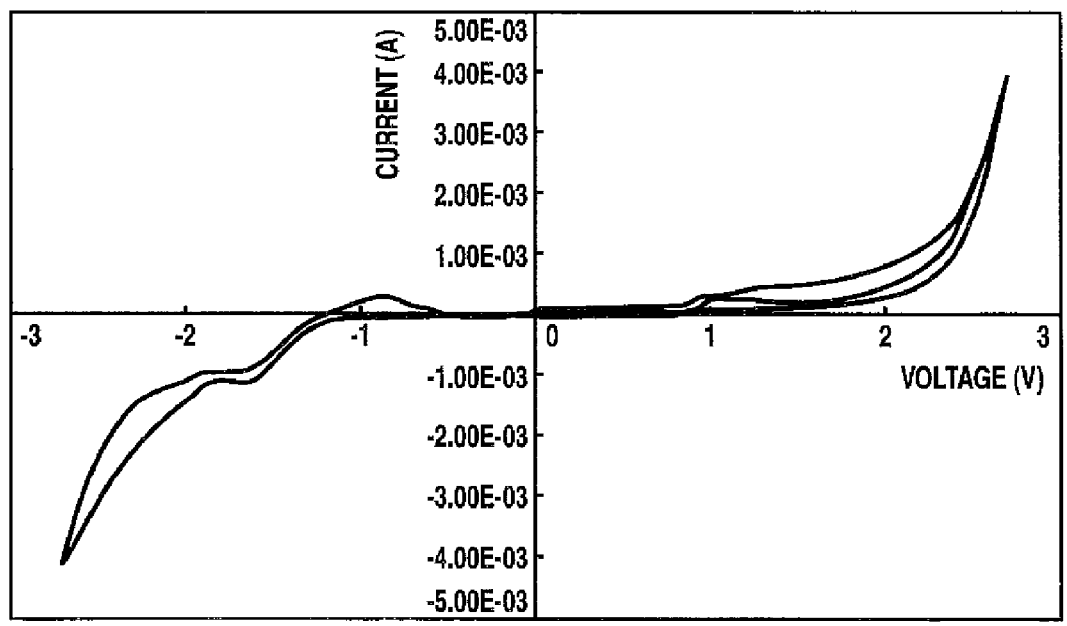
FIG. 4 is a diagram showing cyclic volutammetry of a thiophene derivative 4e.
Figure 5:
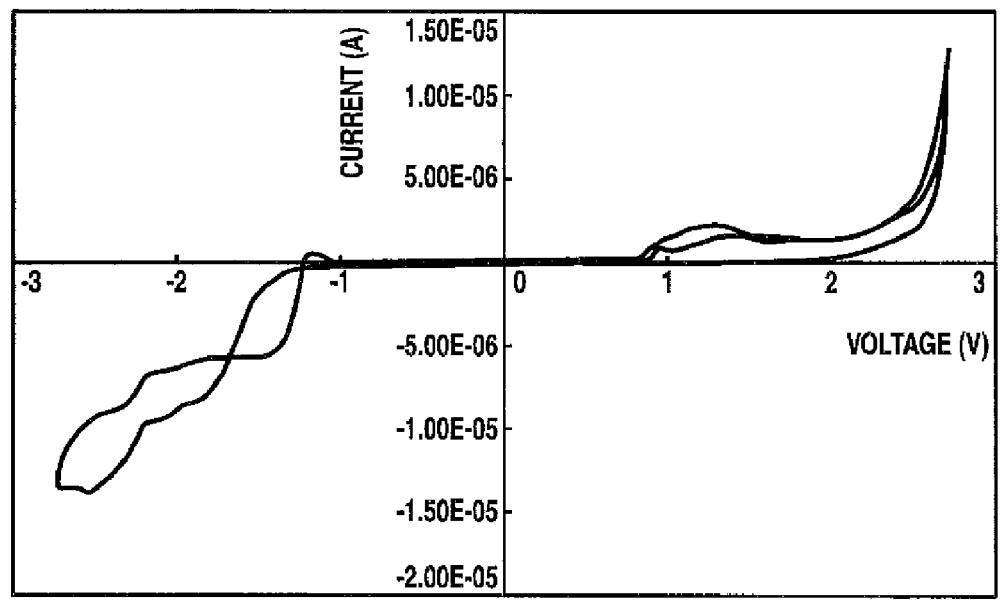
FIG. 5 is a diagram showing cyclic volutammetry of a thiophene derivative 4f.
Figure 6:
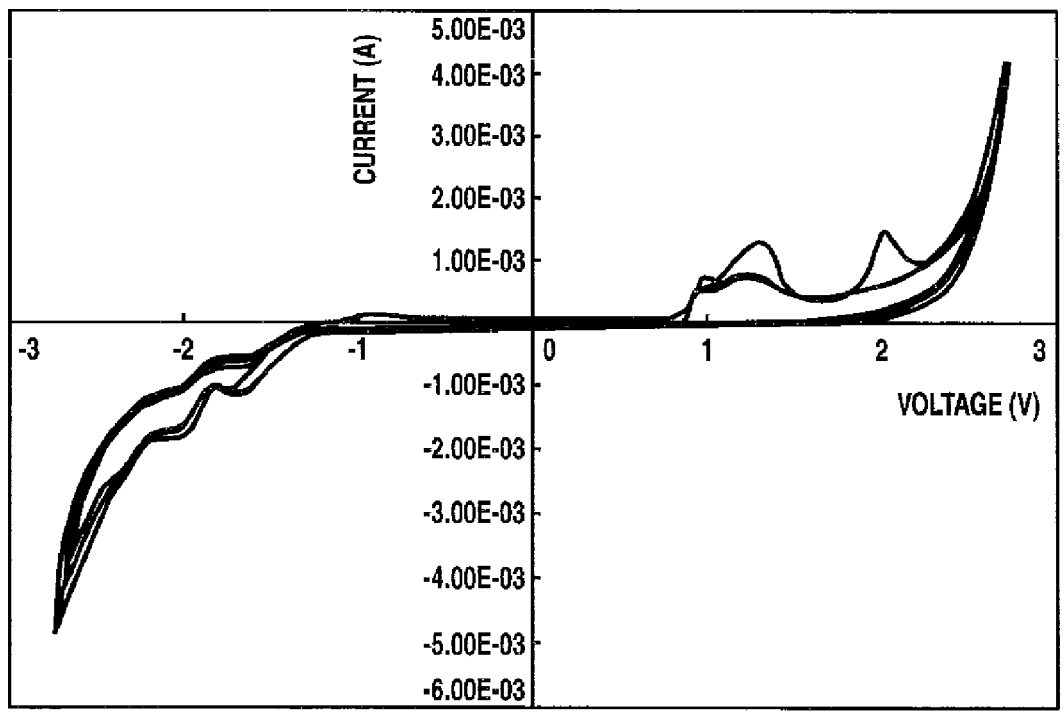
FIG. 6 is a diagram showing cyclic volutammetry of a polymerization product of the thiophene derivative 4b.
Figure 7:
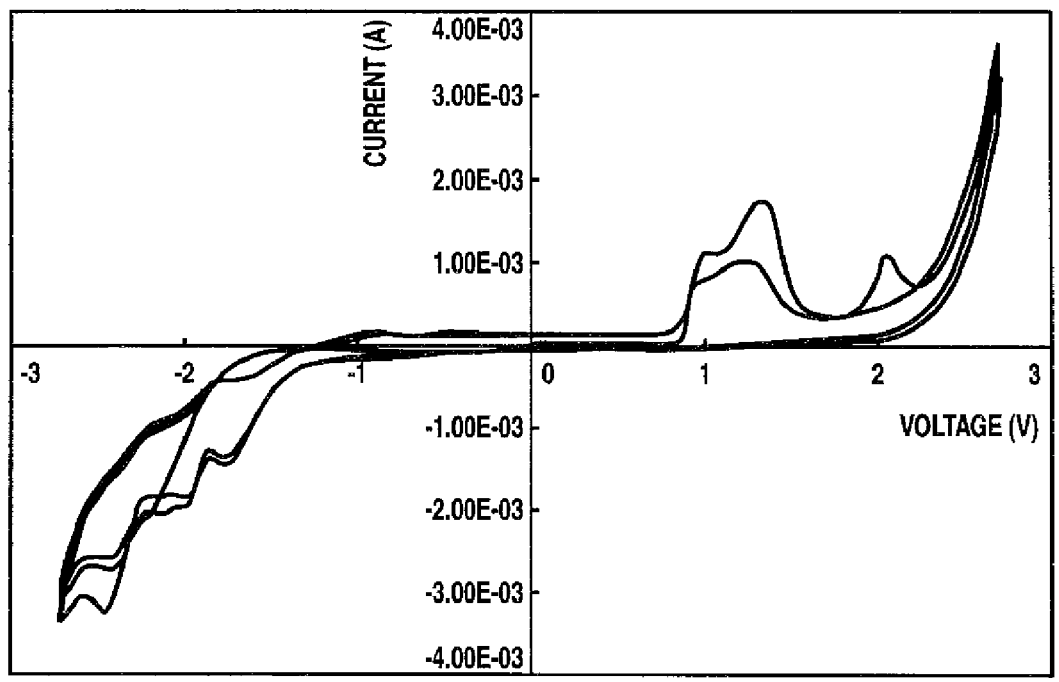
FIG. 7 is a diagram showing cyclic volutammetry of a polymerization product of the thiophene derivative 4c.
Figure 8:
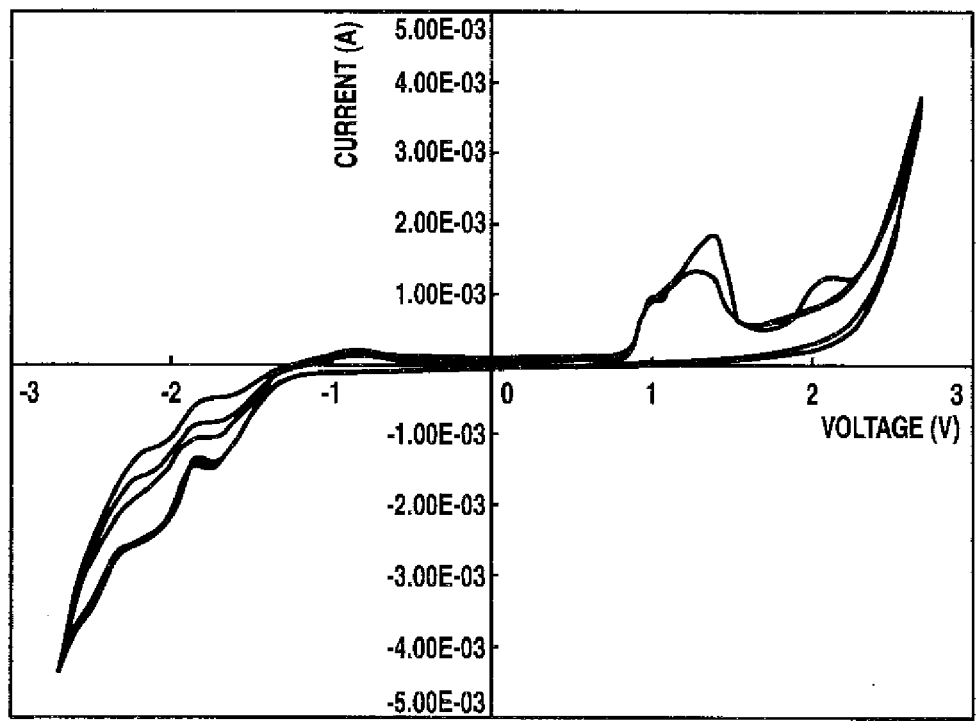
FIG. 8 is a diagram showing cyclic volutammetry of a polymerization product of the thiophene derivative 4d.
Figure 9:
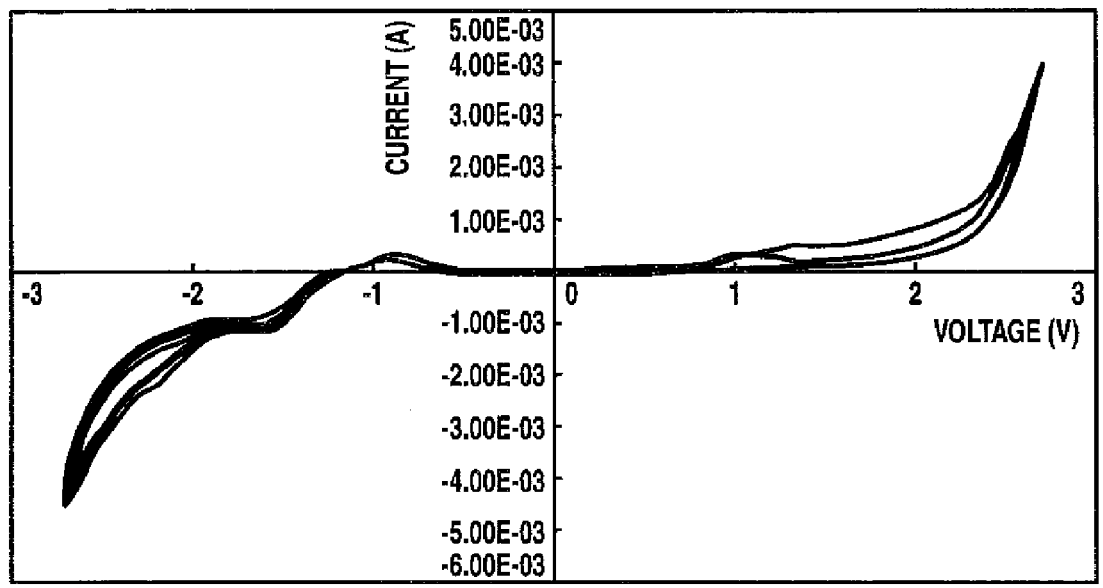
FIG. 9 is a diagram showing cyclic volutammetry of a polymerization product of the thiophene derivative 4e.
Figure 10:
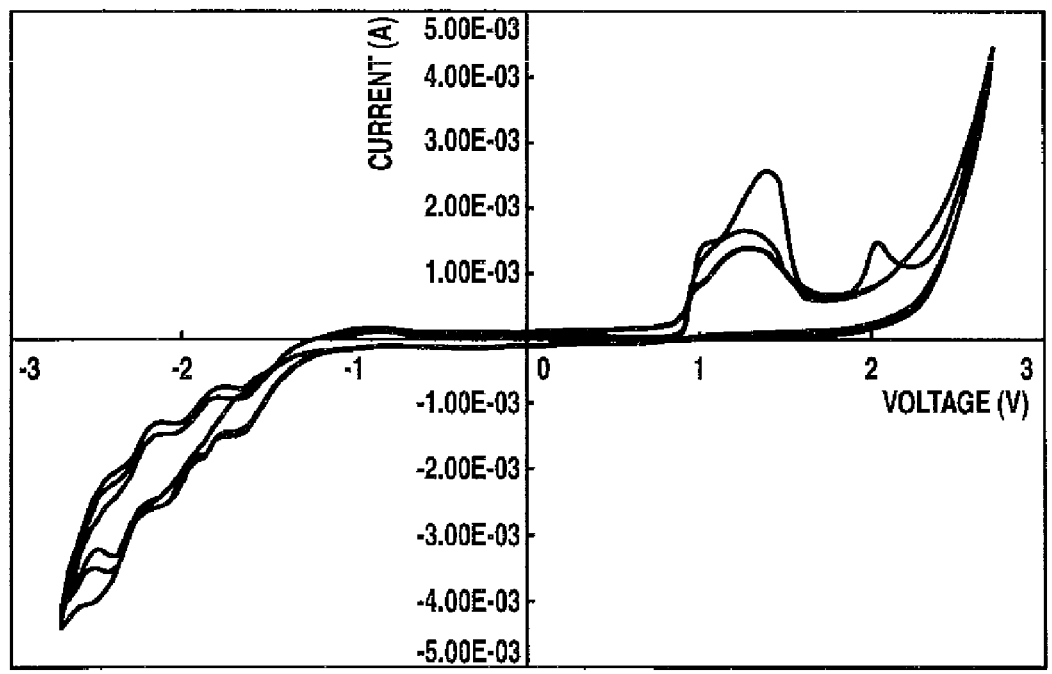
FIG. 10 is a diagram showing cyclic volutammetry of a polymerization product of the thiophene derivative 4f.

With respect to each of the thiophene derivatives 4b to 4f, a cyclic volutammetry measurement was conducted by the potential sweep method while using a three-electrode beaker cell equipped with a platinum counter electrode.
Employed was a solution of the thiophene derivative (concentration: 0.0001 mol/L) and commercial tetrabutylammonium perchlorate (concentration: 0.1 mol/L) in acetonitrile. Using a glassy carbon electrode as a test electrode substrate and Ag/Ag+ as a reference electrode, a measurement was performed by conducting potential sweeping three times while controlling the potential range from −2,700 to 2,700 mV and the sweep rate at 20 mV/sec by the electrochemical measurement system (BAS, Inc.). The results are shown in FIGS. 1 to 5.

Example 11

Cyclic Volutammetry (CV) Measurement in Electrolytic Polymerization

With respect to each of the thiophene derivatives 4b to 4f, electrolytic polymerization was conducted by the potential sweep method while using a three-electrode beaker cell equipped with a platinum counter electrode, and during the electrolytic polymerization, a cyclic volutammetry measurement was performed.

Employed was a solution of the thiophene derivative (concentration: 0.01 mol/L) and commercial tetrabutylammonium perchlorate (concentration: 0.1 mol/L) in acetonitrile. Using a platinum plate (1.0 cm$^2$ per side) as a test electrode substrate and Ag/Ag+ as a reference electrode, a measurement was performed by conducting potential sweeping ten times while controlling the potential range from −2,400 to 2,400 mV and the sweep rate at 50 mV/sec by the electrochemical measurement system (BAS, Inc.). As a result, a yellow polymerization product was observed on the platinum electrode, and a voltage-induced electrochromic phenomenon was determined. Further, peaks of high cycling property were observed on the reduction side in the cyclic volutammetry.

Example 12

Synthesis of poly(3-(octane-1-sulfonyl)-thiophene-2,5-diyl

[Chemical Formula 96]

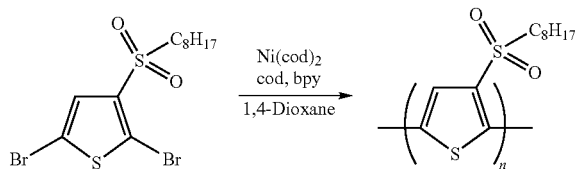

2,5-Dibromo-3-(octane-1-sulfonyl)thiophene, 2,2'-bipyridyl (1.2 equivalents), 1,5-cyclooctanediene (1.0 equivalent) and bis(1,5-cyclooctadiene)nickel(0) (1.2 equivalents) were placed in a reaction vessel, followed by the addition of 1,4-dioxane under a nitrogen atmosphere. The resultant mixture was heated at 60° C. for 20 hours. After completion of the reaction, the reaction mixture was filtered through "Celite", and the residue was washed with chloroform. The filtrate was washed once with a 10% aqueous solution of nitric acid and five times with 10% brine. Anhydrous sodium sulfate was added to the organic layer to dry the same, and the solvent was distilled off. The residue was dried under reduced pressure by a vacuum pump to afford a red solid.

Mw (GPC): 23,000

$^1$H-NMR (CDCl$_3$): 0.8(3H,s), 1.15-1.27(8H,b), 1.29-1.40(2H,b), 1.63-1.77(2H,m), 3.05-3.12(2H,b), 7.81(1H,s)

$^{13}$C-NMR (CDCl$_3$): 14.0(s), 22.4(s), 22.5(s), 28.2(s), 28.9(s), 29.0(s), 31.6(s), 56.3(s), 131.0(s), 133.1(s), 136.7(s), 140.5(s)

Example 13

Synthesis of poly{3-(octane-1-sulfonyl)-thiophene-5,5'-diyl}

[Chemical Formula 97]

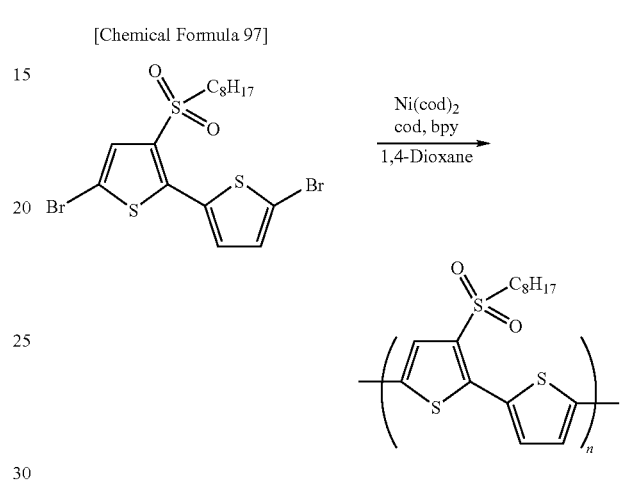

5,5'-Dibromo-3-(octane-1-sulfonyl)-[2,2']-bithiophene, 2,2'-bipyridyl (1.2 equivalents), 1,5-cyclooctanediene (1.0 equivalent) and bis(1,5-cyclooctadiene)nickel(0) (1.2 equivalents) were placed in a reaction vessel, followed by the addition of 1,4-dioxane under a nitrogen atmosphere. The resultant mixture was heated at 60° C. for 20 hours. After completion of the reaction, the reaction mixture was filtered through Celite, and the residue was washed with chloroform. The filtrate was washed once with a 10% aqueous solution of nitric acid and five times with 10% brine. Anhydrous sodium sulfate was added to the organic layer to dry the same, and the solvent was distilled off. The residue was dried under reduced pressure by a vacuum pump to afford a red solid.

Mw (GPC): 8,500

$^1$H-NMR (CDCl$_3$): 0.81-0.90(3H,m), 1.15-1.38(8H,m), 1.48-1.79(4H,m), 2.94-3.16(2H,m), 7.07-7.70(3H,m),

Example 14

Synthesis of poly{3',4'-bis(octane-1-sulfonyl)-[2,2';5',2"]-terthiophene-5,5"-diyl}

[Chemical Formula 98]

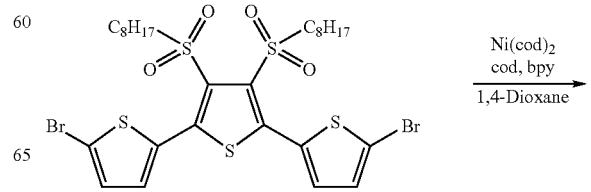

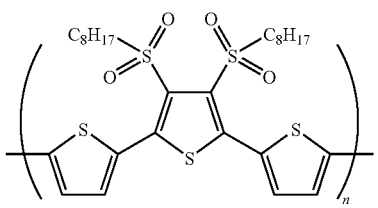

5,5''-Dibromo-3',4''-bis(octane-1-sulfonyl)-[2,2'; 5',2'']-terthiophene, 2,2'-bipyridyl (1.2 equivalents), 1,5-cyclooctanediene (1.0 equivalent) and bis(1,5-cyclooctadiene)nickel (0) (1.2 equivalents) were placed in a reaction vessel, followed by the addition of 1,4-dioxane under a nitrogen atmosphere. The resultant mixture was heated at 60° C. for 20 hours. After completion of the reaction, the reaction mixture was filtered through Celite, and the residue was washed with chloroform. The filtrate was washed once with a 10% aqueous solution of nitric acid and five times with 10% brine. Anhydrous sodium sulfate was added to the organic layer to dry the same, and the solvent was distilled off. The residue was dried under reduced pressure by a vacuum pump to afford an orange solid.

Mw (GPC): 106,000

$^1$H-NMR (CDCl$_3$): 1.20-1.29(6H,m), 4.02-4.18(4H,m), 6.91(1H,s)

Example 15

Synthesis of 2,5-dibromo-3-(octane-1-sulfonyl)thiophene

[Chemical Formula 99]

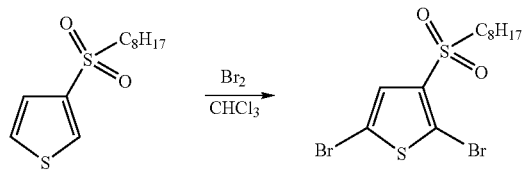

3-(Octane-1-sulfonyl)thiophene was placed in a reaction vessel. Under a nitrogen atmosphere, chloroform was added to dissolve 3-(octane-1-sulfonyl)thiophene, and the resultant solution was cooled to −5° C. To the solution, bromine (5 equivalents) diluted with chloroform was gradually added. Subsequent to completion of the dropwise addition, the mixture was heated to room temperature and then stirred for 23 hours. After completion of the reaction, a 1 N aqueous solution of sodium hydroxide was added to the reaction mixture to quench the reaction, followed by extraction with chloroform. The organic layer was washed with a 10% aqueous solution of sodium thiosulfate and then with 10% brine, and was dried over anhydrous sodium sulfate. The solvent was distilled off, and the resultant crude product was purified through a silica gel column (hexane:ethyl acetate=93:7) to afford a white solid.

m/z: 417 (calculated: 415.91)

$^1$H-NMR (CDCl$_3$): 0.88(3H,t,J=6.6 Hz), 1.26-1.40(10H, m), 1.74(2H,m), 3.23(2H,t,J=7.8 Hz), 7.32(1H,s)

Example 16

Synthesis of 3-(octane-1-sulfonyl)-[2,2']-bithiophene

[Chemical Formula 100]

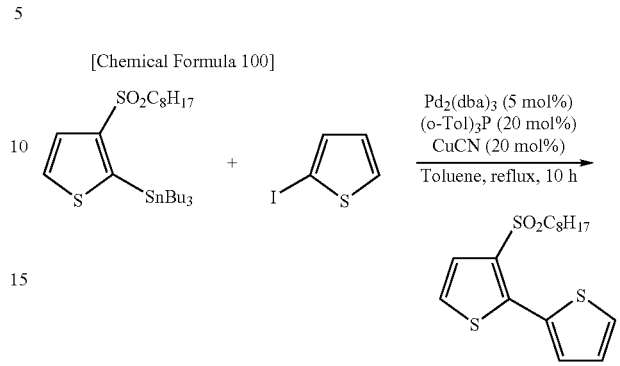

In a reaction vessel, tributyl{3-(octyl-1-sulfonyl)-thiophen-2-yl}stannan and 2-iodothiophene (1.1 equivalents) were placed. After toluene was added at room temperature to dissolve them, tris(dibenzylideneacetone) dipalladium(0) (0.05 equivalent), tri(orthotolyl)phosphine (0.2 equivalent) and copper(I) cyanide (0.2 equivalent) were added under a nitrogen atmosphere, and the resulting mixture was protected from light. After the mixture was heated under reflux for 10 hours, the temperature was allowed to drop down to room temperature, the reaction was terminated with an aqueous solution of potassium fluoride, and the reaction mixture was stirred for 2 hours. The reaction mixture was filtered through Celite, followed by extraction with ethyl acetate. The organic layer was washed with saturated brine and dried over anhydrous sodium sulfate. The solvent was distilled off, and the resultant crude product was purified through a silica gel column (hexane:chloroform=2:3) to afford a yellow liquid.

$^1$H-NMR (CDCl$_3$): 7.60-7.61(1H,dd,J=0.98, 1.00 Hz), 7.51-7.52(1H,d,J=5.48 Hz), 7.47-7.48(1H,dd,J=1.00, 0.98 Hz), 7.31-7.33(1H,d,J=5.47 Hz), 7.12-7.14(1H,q, J=2.94 Hz), 2.92-2.96(2H,m), 1.56-1.62(2H,m), 1.17-1.25(10H,m), 0.84-0.87(3H,t,J=7.03 Hz) ppm.

Example 17

Synthesis of 5,5'-dibromo-3-(octane-1-sulfonyl)-[2, 2']-bithiophene

[Chemical Formula 101]

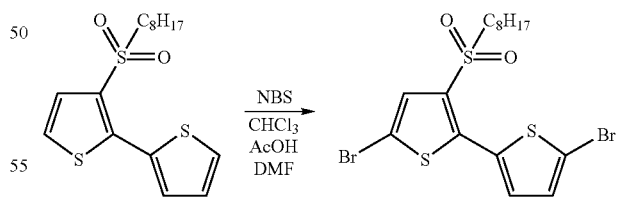

In a reaction vessel, 3-(octane-1-sulfonyl)-[2,2']-bithiophene was placed. After chloroform, acetic acid and N,N-dimethylformamide were added to dissolve it, N-bromosuccinimide (2.2 equivalents) was added, and the resulting mixture was stirred at room temperature for 24 hours. After the reaction, a disodium hydrogenphosphate/sodium dihydrogenphosphate buffer which had been adjusted to pH 7 was added to quench the reaction, and the reaction mixture was extracted with chloroform. The organic layer was washed with a 10% aqueous solution of sodium thiosulfate and then with 10% brine, and was dried over anhydrous sodium sulfate. The solvent was distilled off, and the resultant crude product was purified through a silica gel column (hexane:ethyl acetate=99:1) to afford a green liquid.

m/z (DI): 497.70 (Calculated: 497.90)

¹H-NMR (CDCl₃): 0.87(3H,t,J=6.6 Hz), 1.21-1.28(8H, m), 1.59-1.68(2H,m), 2.97(2H,q, J=7.1 Hz), 4.12(2H,q, J=7.1 Hz), 7.09(1H,d,J=3.9 Hz), 7.29(1H,d,J=3.9 Hz), 7.45 (1H,s).

Example 18

Synthesis of 5,5'-dibromo-3',4'-bis(octane-1-sulfonyl)-[2,2'; 5',2"]-terthiophene

[Chemical Formula 102]

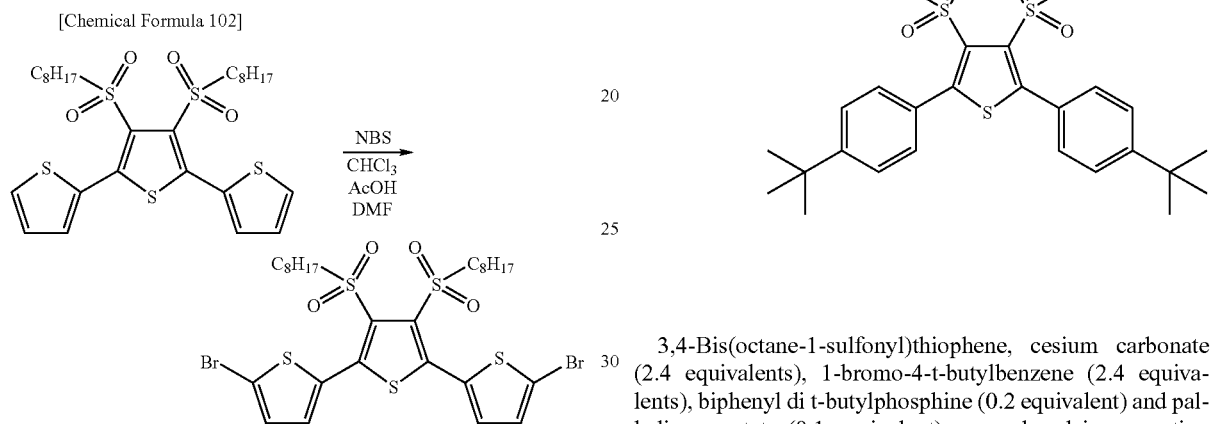

3',4'-Bis(octane-1-sulfonyl)-[2,2'; 5',2"]-terthiophene was placed in a reaction vessel. After chloroform, acetic acid and N,N-dimethylformamide were added to dissolve it, N-bromosuccinimide (2.2 equivalents) was added, and the resulting mixture was stirred at room temperature for 24 hours. After the reaction, a disodium hydrogenphosphate/sodium dihydrogenphosphate buffer which had been adjusted to pH 7 was added to quench the reaction, and the reaction mixture was extracted with chloroform. The organic layer was washed with a 10% aqueous solution of sodium thiosulfate and then with 10% brine, and was dried over anhydrous sodium sulfate. The solvent was distilled off, and the resultant crude product was purified through a silica gel column (hexane:ethyl acetate=97:3) to obtain the reaction product.

¹H-NMR (CDCl₃): 0.88(6H,t,J=6.9 Hz), 1.17-1.36(16H, m), 1.69-1.90(4H,m), 3.63(4H,q, J=7.1 Hz), 4.12(4H,q, J=7.1 Hz), 7.01(2H,d,J=3.8 Hz), 7.06(2H,d,J=3.8 Hz).

Example 19

Synthesis of 2,5-bis(4-t-butylphenyl)-3,4-bis(octane-1-sulfonyl)thiophene

[Chemical Formula 103]

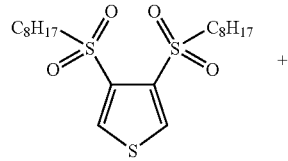

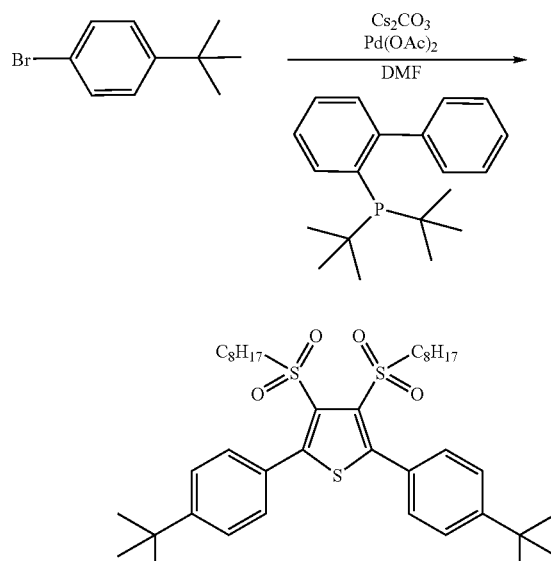

3,4-Bis(octane-1-sulfonyl)thiophene, cesium carbonate (2.4 equivalents), 1-bromo-4-t-butylbenzene (2.4 equivalents), biphenyl di t-butylphosphine (0.2 equivalent) and palladium acetate (0.1 equivalent) were placed in a reaction vessel. Under a nitrogen gas atmosphere, DMF was added, followed by heating at 150° C. for 7 hours. After completion of the reaction, the reaction mixture was filtered through Celite, and the residue was washed with ethyl acetate. The filtrate was washed with a 1 N aqueous solution of hydrochloric acid and then with 10% brine, anhydrous sodium sulfate was added to the organic layer to dry the same, and the solvent was distilled off. The thus-obtained crude product was purified through a silica gel column (hexane:ethyl acetate=99:1) to afford a white to brown solid.

m/z (DI): 701.35 (Calculated: 700.37)

¹H-NMR (CDCl₃): 0.88(6H,t,J=6.9 Hz), 1.25-1.45(24H, m), 1.36(18H,s), 3.61(4H,t,J=8.0 Hz), 7.34(4H,d,J=6.0 Hz), 7.43(4H,d,J=6.0 Hz).

Example 20

Synthesis of 2,5-bis(4-t-butylphenyl)-3-(octane-1-sulfonyl)thiophene

[Chemical Formula 104]

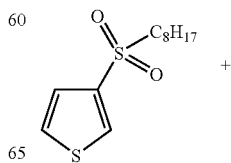

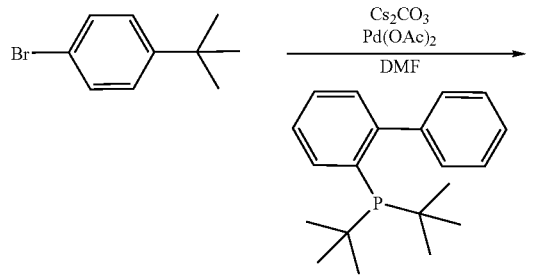

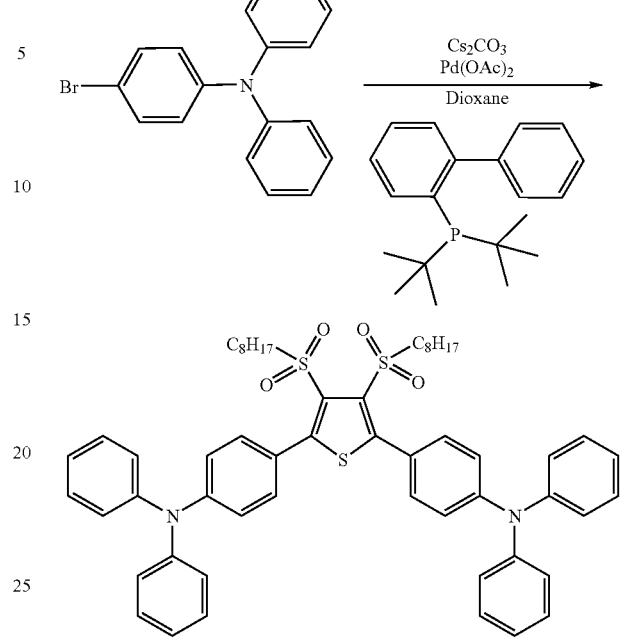

3-(Octane-1-sulfonyl)thiophene, cesium carbonate (2.4 equivalents), 1-bromo-4-t-butylbenzene (2.4 equivalents), biphenyl di t-butylphosphine (0.2 equivalent) and palladium acetate (0.1 equivalent) were placed in a reaction vessel. Under a nitrogen gas atmosphere, DMF was added, followed by heating at 150° C. for 7 hours. After completion of the reaction, the reaction mixture was filtered through Celite, and the residue was washed with ethyl acetate. The filtrate was washed with a 1 N aqueous solution of hydrochloric acid and then with 10% brine, anhydrous sodium sulfate was added to the organic layer to dry the same, and the solvent was distilled off. The thus-obtained crude product was purified through a silica gel column (hexane:ethyl acetate=19:1) to afford a white to brown, glassy reaction product.

m/z (DI): 524.10 (Calculated: 524.28)

$^1$H-NMR (CDCl$_3$): 0.85(3H,t,J=6.6 Hz), 1.13-1.29(10H, m), 1.35(9H,s), 1.36(9H,s), 1.59(2H,m), 2.82(2H,t,J=8.0 Hz), 7.45-7.67(8H,m).

3,4-Bis(octane-1-sulfonyl)thiophene, cesium carbonate (2.4 equivalents), 4-bromo-N,N-diphenylaniline (2.4 equivalents), biphenyl di t-butylphosphine (0.2 equivalent) and palladium acetate (0.1 equivalent) were placed in a reaction vessel. Under a nitrogen gas atmosphere, DMF was added, followed by heating at 150° C. for 7 hours. After completion of the reaction, the reaction mixture was filtered through Celite, and the residue was washed with ethyl acetate. The filtrate was washed with a 1 N aqueous solution of hydrochloric acid and then with 10% brine, anhydrous sodium sulfate was added to the organic layer to dry the same, and the solvent was distilled off. The thus-obtained crude product was purified through a silica gel column (hexane:ethyl acetate=9:1) to afford a slightly yellow solid.

m/z (DI): 921.98 (Calculated: 922.39)

$^1$H-NMR (CDCl$_3$): 0.86(6H,t,J=7.1 Hz), 1.20-1.32(16H, m), 1.35-1.44(4H,m), 1.72-1.88(4H,m), 3.61(4H,t,J=8.0 Hz), 7.02-7.37(28H,m).

Example 21

Synthesis of 4,4'-{3,4-bis(octane-1-sulfonyl)-thiophene-2,5-diyl}bis(N,N-diphenylaniline)

Example 22

Synthesis of 4,4'-{3-(octane-1-sulfonyl)-thiophene-2, 5-diyl}bis(N,N-diphenylaniline)

[Chemical Formula 105]

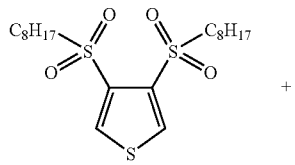

+

[Chemical Formula 106]

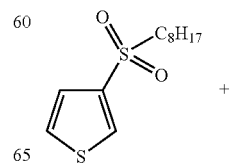

+

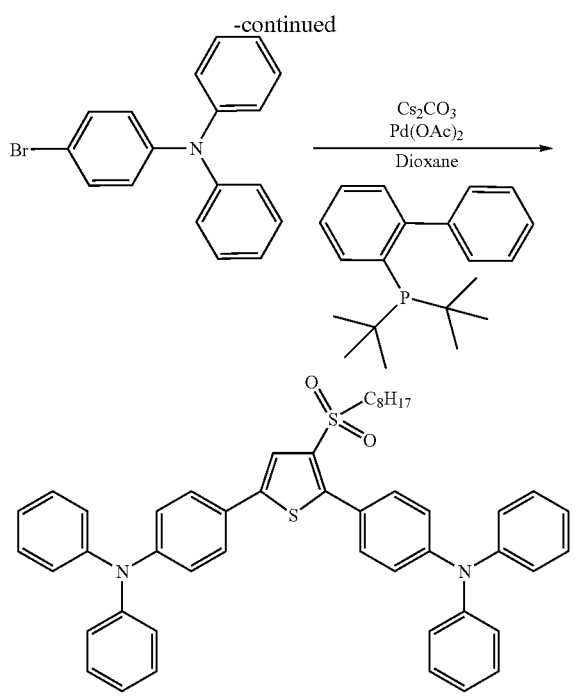

3-(Octane-1-sulfonyl)thiophene, cesium carbonate (2.4 equivalents), 4-bromo-N,N-diphenylaniline (2.4 equivalents), biphenyl di t-butylphosphine (0.2 equivalent) and palladium acetate (0.1 equivalent) were placed in a reaction vessel. Under a nitrogen gas atmosphere, DMF was added, followed by heating at 150° C. for 7 hours. After completion of the reaction, the reaction mixture was filtered through "Celite", and the residue was washed with ethyl acetate. The filtrate was washed with a 1 N aqueous solution of hydrochloric acid and then with 10% brine, anhydrous sodium sulfate was added to the organic layer to dry the same, and the solvent was distilled off. The thus-obtained crude product was purified through a silica gel column (hexane:ethyl acetate=5:1) to afford an optic yellow solid.

m/z (DI): 745.93 (Calculated: 746.30)

$^1$H-NMR (CDCl$_3$): 0.84(3H,t,J=7.1 Hz), 1.13-1.30(10H, m), 1.50-1.60(2H,m), 2.89(2H,q, J=8.0 Hz), 7.04-7.17(10H, m), 7.26-7.33(10H,m), 7.43-7.59(5H,m).

Example 23

Synthesis of 2,3-bis(butane-1-sulfanyl)-butadiene

[Chemical Formula 107]

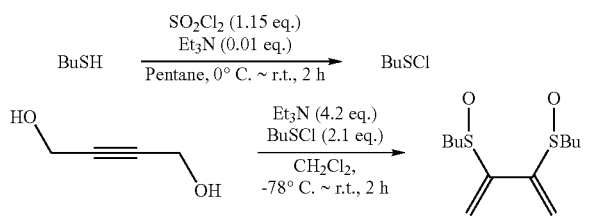

Under a nitrogen atmosphere, 1-butanethiol, triethylamine (0.01 equivalent) and pentane were placed in a reaction vessel. After the resulting mixture was cooled to 0° C., thionyl chloride (1.15 equivalents) was gradually added dropwise, followed by stirring for 1 hour. The temperature of the reaction mixture was allowed to rise to room temperature, and the reaction mixture was stirred for 1 hour. Subsequently, the remaining thionyl chloride and solvent were distilled off, and the crude product was distilled (at 128 mmHg and 84° C.) to afford 1-butanesulfenyl chloride.

Under a nitrogen atmosphere, 2-butyne-1,4-dithiol, triethylamine (4.2 equivalents) and methylene chloride were placed in a reaction vessel. After they were cooled to −78° C., 1-butanesulfenyl chloride (2.1 equivalents) was gradually added, followed by stirring for 1 hour. The temperature of the reaction mixture was allowed to rise to room temperature, and the reaction mixture was stirred for 1 hour. A disodium hydrogenphosphate/sodium dihydrogenphosphate buffer which had been adjusted to pH 7 was added to quench the reaction, and the reaction mixture was extracted with methylene chloride. The organic layer was washed three times with saturated brine, and was dried over anhydrous sodium sulfate. The solvent was distilled off, and the resultant crude product was purified through a silica gel column (hexane:ethyl acetate=1:2) to obtain the reaction product.

Example 24

Synthesis of 2,3-bis(butane-1-sulfonyl)-butadiene

[Chemical Formula 108]

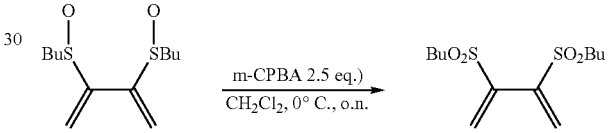

Under a nitrogen atmosphere, m-chloroperbenzoic acid (2.5 equivalents) and methylene chloride were placed in a reaction vessel. After the resulting mixture was cooled to 0° C., 2,3-bis(butane-1-sulfanyl)butadiene was gradually added dropwise, followed by stirring overnight. To the reaction mixture, a saturated aqueous solution of sodium hydrogencarbonate was added to quench the reaction. The reaction mixture was extracted with methylene chloride. The organic layer was washed three times with a saturated aqueous solution of sodium hydrogencarbonate, a saturated aqueous solution of sodium sulfite and saturated brine, respectively, and was then dried over anhydrous sodium sulfate. The solvent was distilled off. The resultant crude product the resultant crude product was purified through a silica gel column (hexane: ethyl acetate=2:1) to obtain the reaction product.

Example 25

Synthesis of 3,4-bis(butane-1-sulfonyl)-tetrahydrothiophene

[Chemical Formula 109]

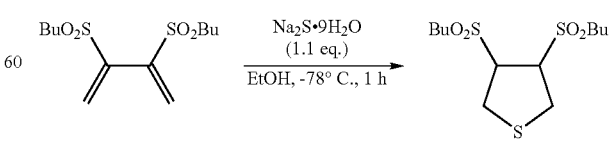

Under a nitrogen atmosphere, 2,3-bis(butane-1-sulfonyl) butadiene and ethanol were placed in a reaction vessel. 2,3-Bis(butane-1-sulfonyl)butadiene was dissolved in ethanol, and the resultant solution was cooled to −78° C. In another reaction vessel, sodium sulfite 9-hydrate and ethanol were added to another reaction vessel to prepare a solution. That solution was gradually added dropwise to the ethanol solution of 2,3-bis(butane-1-sulfonyl)butadiene. After the mixture was stirred for 1 hour, a disodium hydrogenphosphate/sodium dihydrogenphosphate buffer which had been adjusted to pH 7 was added to quench the reaction, and the reaction mixture was extracted with ethyl acetate. The organic layer was washed three times with saturated brine, and was dried over anhydrous sodium sulfate. The solvent was distilled off, and the resultant crude product was purified through a silica gel column (hexane:ethyl acetate=2:1) to obtain the reaction product.

Example 26

Synthesis of 3,4-bis(butane-1-sulfonyl)-sulfuran

[Chemical Formula 110]

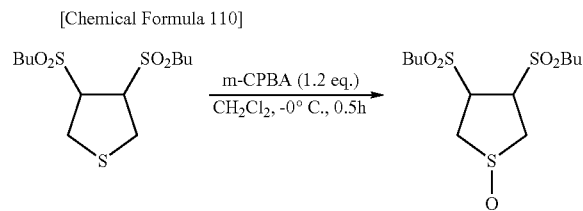

Under a nitrogen atmosphere, m-chloroperbenzoic acid (2.5 equivalents) and methylene chloride were placed in a reaction vessel. After the resulting mixture was cooled to 0° C., 3,4-bis(butane-1-sulfonyl)tetrahydrothiophene dissolved in methylene chloride was gradually added dropwise, followed by stirring for 30 minutes. To the reaction mixture, a saturated aqueous solution of sodium hydrogencarbonate was added to quench the reaction. The reaction mixture was extracted with methylene chloride. The organic layer was washed three times with a saturated aqueous solution of sodium hydrogencarbonate, a saturated aqueous solution of sodium sulfite and saturated brine, respectively, and was then dried over anhydrous sodium sulfate. The solvent was distilled off. The resultant crude product was purified through a silica gel column (ethyl acetate) to obtain the reaction product.

Example 27

Synthesis of 3,4-bis(butane-1-sulfonyl)-dihydrothiophene

[Chemical Formula 111]

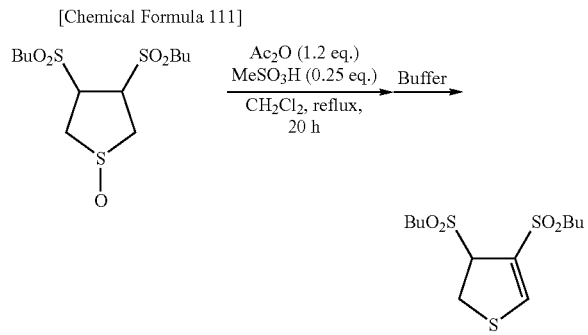

Under a nitrogen atmosphere, 3,4-bis(butane-1-sulfonyl) sulfuran and methylene chloride were placed in a reaction vessel to dissolve 2,3-bis(butane-1-sulfonyl)-sulfuran in methylene chloride. To the solution, acetic anhydride (1.2 equivalents) and methanesulfonic acid (0.25 equivalent) were added, followed by heating under reflux for 20 hours. A disodium hydrogenphosphate/sodium dihydrogenphosphate buffer which had been adjusted to pH 7 was added to the reaction mixture to quench the reaction, and the reaction mixture was extracted with ethyl acetate. The organic layer was washed three times with saturated brine, and was dried over anhydrous sodium sulfate. The solvent was distilled off. The resultant crude product was purified through a silica gel column (hexane:ethyl acetate=2:1) to obtain the reaction product.

Example 28

Synthesis of 3-(butane-1-sulfonyl)thiophene

[Chemical Formula 112]

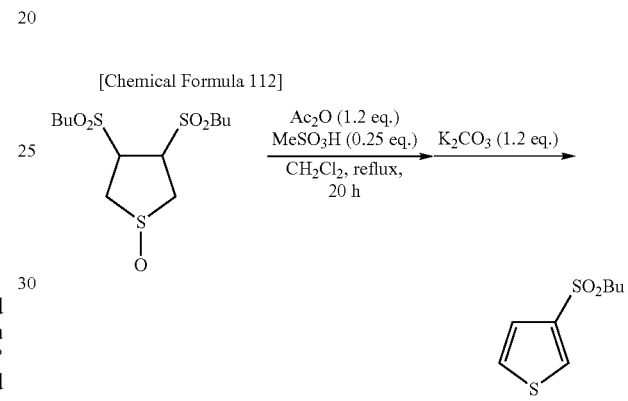

Under a nitrogen atmosphere, 3,4-bis(butane-1-sulfonyl) sulfuran and methylene chloride were placed in a reaction vessel to dissolve 3,4-bis(butane-1-sulfonyl)-sulfuran in methylene chloride. To the solution, acetic anhydride (1.2 equivalents) and methanesulfonic acid (0.25 equivalent) were added, followed by heating under reflux for 20 hours. Potassium carbonate (1.2 equivalents) was added to the reaction mixture, and the resulting mixture was stirred. The reaction mixture was filtered, the residue was washed with ethyl acetate, and the solvent was distilled off from the filtrate. The resultant crude product was purified through a silica gel column (hexane:ethyl acetate=2:1) to obtain the reaction product.

Example 29

Synthesis of 3,4-bis(butane-1-sulfonyl)-thiophene

[Chemical Formula 113]

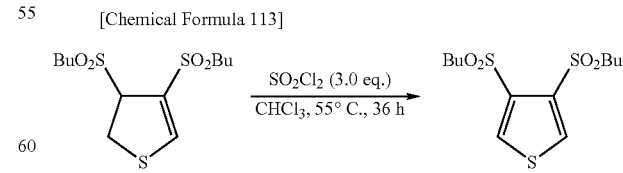

Under a nitrogen atmosphere, 3,4-bis(butane-1-sulfonyl) dihydrothiophene and chloroform were placed in a reaction vessel to dissolve 3,4-bis(butane-1-sulfonyl)-dihydrothiophene in chloroform. To the solution, thionyl chloride (3.0 equivalents) was added, followed by heating under reflux for 36 hours. A disodium hydrogenphosphate/sodium dihydrogenphosphate buffer which had been adjusted to pH 7 was added to the reaction mixture to quench the reaction, and the reaction mixture was extracted with ethyl acetate. The organic layer was washed three times with saturated brine, and was dried over anhydrous sodium sulfate. The solvent was distilled off. The resultant crude product was purified through a silica gel column (hexane:ethyl acetate=2:1) to obtain the reaction product.

Example 30

Sublimation (Vapor Deposition) Test

The sulfonylthiophene compounds synthesized in Examples 21 and 22 were separately placed in crucibles as much as needed (approximately to the halves). After depressurization to a high vacuum (0.5 to 2.5 mPa) by a turbomolecular pump, a voltage was applied across filaments arranged under the crucibles to heat the crucibles. Using quartz substrates as deposition substrates, the measurement of deposition rates by a quartz oscillator was performed.

With respect to each of the complexes, vapor deposition was initiated from 12 A. When the deposition rate was insufficient, the current magnitude was increased 0.5 A by 0.5 A at intervals of 2 minutes, and the current was fed until vapor deposition was finally stopped. When vacuum evaporation began to take place, vapor deposition onto the ITO coated substrate was initiated from a deposit rate of 0.02 nm/sec or so. The deposit rate was stably maintained at 0.3 to 0.5 nm/sec or so. The vapor deposition was continued up to 900 nm maximum on a film thickness meter (approximately 300 nm or so by actual measurement), and the vacuum evaporation operation was stopped. The actual measurement values of film thicknesses are shown in Table 5.

TABLE 5

| RUN | Film thickness meter | Actual measurement |
|---|---|---|
| | Example 21 | |
| 1 | 100 nm | 34 nm |
| 2 | 275 nm | 104 nm |
| 3 | 400 nm | 130 nm |
| | Example 22 | |
| 4 | 265 nm | 82 nm |
| 5 | 400 nm | 123 nm |
| 6 | 531 nm | 200 nm |
| 7 | 870 nm | 333 nm |

Example 31

Solubility Test

The solubility of each of the sulfonylthiophene compounds synthesized in Examples 21 and 22 was determined under ultrasonic waves at 25° C. by adding, to aliquots (5 mg) of the sulfonylthiophene compound, tetrahydrofuran (THF), toluene, N,N-dimethylformamide (DMF), chloroform, ethyl acetate and ethanol 50 μL by 50 μL, respectively, until they were dissolved. The results are shown in Table 6. The level of solubility was ranked in accordance with the following standards.

⊚: Dissolved with 50 μL (concentration: 10%)
○: Dissolved with 100 μL (concentration: 5%)
Δ: Dissolved with 200 μL (concentration: 2.5%)
X: Not dissolved even by the addition of 500 μL (concentration: 1% or lower)

TABLE 6

| Solvent | Example 21 | Example 22 |
|---|---|---|
| THF | ○ | ⊚ |
| Toluene | ○ | ⊚ |
| DMF | Δ | ⊚ |
| Chloroform | ⊚ | ⊚ |
| Ethyl acetate | ○ | ⊚ |
| Ethanol | X | X |

Example 32

An ITO coated glass substrate which had been subjected for 40 minutes to ozone cleaning was introduced into a vacuum evaporation system, and the sulfonylthiophene compound synthesized in Example 21, α-NPD, Alq$_3$, LiF and Al were successively deposited. Their film thicknesses were set at 30 nm, 35 nm, 50 nm, 0.5 nm and 100 nm, respectively, and their vapor deposition operations were each initiated after the pressure dropped to $2 \times 10^{-3}$ Pa or lower. The deposit rate was controlled at 0.3 to 0.4 nm/sec except for LiF, and the deposit rate for LiF was controlled at 0.02 to 0.04 nm. Transfer operations between the respective vapor deposition operations were conducted in a vacuum. The characteristics of the resultant EL devices were measured by an organic EL luminescence efficiency measurement system. The results are shown in Table 7. The characteristics of EL devices (Comparative Example 1) fabricated likewise without incorporation of the sulfonylthiophene compound synthesized in Example 21 are also shown in Table 7.

TABLE 7

| | Current density [mA/cm$^2$] | Voltage [V] | Brightness [cd/m$^2$] | Current efficiency [cd/A] | Light-emission initiating voltage [V] | Maximum brightness [cd/m$^2$] |
|---|---|---|---|---|---|---|
| Example 32(1) | 100 | 8.74 | 1468 | 1.475 | 3.7 | 3550 |
| Example 32(2) | 200 | 9.30 | 2843 | 1.486 | 3.7 | 3550 |
| Comparative Example 1(1) | 100 | 7.33 | 839 | 0.836 | 4.8 | 1253 |
| Comparative Example 1(2) | 200 | 7.72 | 1257 | 0.629 | 4.8 | 1253 |

The invention claimed is:

1. A sulfonylthiophene oligomer compound represented by the following formula [2]:

[2]

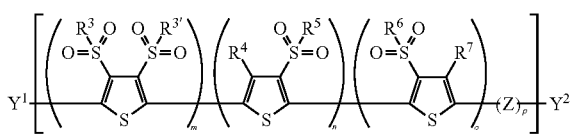

wherein R$^3$ and R$^{3'}$ each independently represent an alkyl group having 1 to 20 carbon atoms, haloalkyl group having 1 to 20 carbon atoms, phenyl group which may be substituted by W, or thienyl group which may be substituted by W, or R³ and R³' are fused together to represent an alkylene group which has 1 to 3 carbon atoms and may be substituted by W, phenylene group which may be substituted by W, or —(CH₂)q-SO₂—(CH₂)q-SO₂—(CH₂)q- in which q stands for an integer of from 1 to 3, R⁵ and R⁶ each independently represent an alkyl group having 1 to 20 carbon atoms, haloalkyl group having 1 to 20 carbon atoms, phenyl group which may be substituted by W, or thienyl group which may be substituted by W, R⁴ and R⁷ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 10 carbon atoms, monoalkylamino group having 1 to 10 carbon atoms, dialkylamino group having 1 to 10 carbon atoms, or phenyl group which may be substituted by W, W represents a halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', N-naphthyl-N-anthranylamino group which may be substituted by W', trialkylsilyl group having 1 to 10 carbon atoms, alkylcarbonyl group having 1 to 10 carbon atoms, alkoxycarbonyl group having 1 to 10 carbon atoms, or phenyl group which may be substituted by W', W' represents an alky group having 1 to 10 carbon atoms, haloalkyl group having 1 to 10 carbon atoms, or alkoxy group having 1 to 10 carbon atoms, m stands for an integer of 1 or greater, n and o each independently stand for 0 or an integer of 1 or greater, p stands for 0 or an integer of 1 or greater, and m, n, o and p satisfy m+n+o≧1 and 1≦m+n+o+p≦50, Z is at least one divalent organic group selected from the following formulas [3] to [11]:

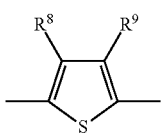

[3]

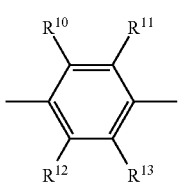

[4]

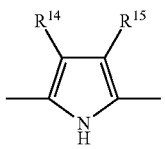

[5]

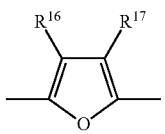

[6]

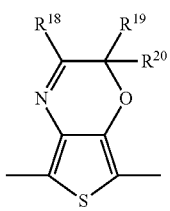

[7]

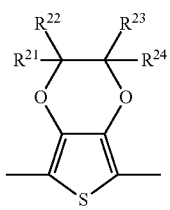

[8]

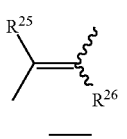

[9]

[10]

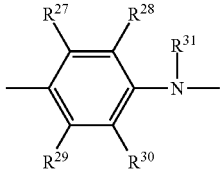

[11]

wherein R⁸ to R³⁰ each independently represent a hydrogen atom, alkyl group having 1 to 20 carbon atoms, haloalkyl group having 1 to 20 carbon atoms, alkoxy group having 1 to 10 carbon atoms, alkylthio group having 1 to 20 carbon atoms, dialkylamino group having 1 to 10 carbon atoms, or phenyl group which may be substituted by W, W has the same meaning as defined above, R³¹ represents a hydrogen atom, alkyl group having 1 to 20 carbon atoms, haloalkyl group having 1 to 20 carbon atoms, alkoxy group having 1 to 10 carbon atoms, or phenyl group which may be substituted by W', and W' has the same meaning as defined above, and Y¹ and Y² each independently represent at least one monovalent organic group selected from the following formulas [12] to [15]:

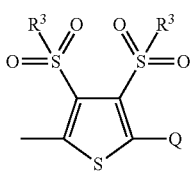

[12]

-continued

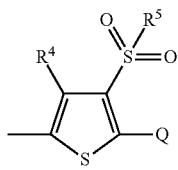
[13]

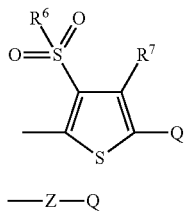
[14]

—Z—Q
[15]

wherein $R^3$ to $R^7$ and Z have the same meanings as defined above, Q are both ends of said sulfonylthiophene oligomer compound and each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, and W has the same meaning as defined above.

2. The sulfonylthiophene oligomer compound according to claim 1, wherein Z is a divalent organic group represented by the formula [3].

3. A sulfonylthiophene polymer compound represented by the following formula [25]:

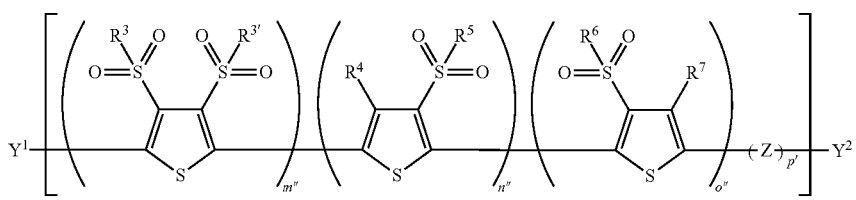
[25]

wherein $R^3$ and $R^{3'}$ each independently represent an alkyl group having 1 to 20 carbon atoms, haloalkyl group having 1 to 20 carbon atoms, phenyl group which may be substituted by W, or thienyl group which may be substituted by W, or $R^3$ and $R^{3'}$ are fused together to represent an alkylene group which has 1 to 3 carbon atoms and may be substituted by W, phenylene group which may be substituted by W, or —(CH$_2$)q-SO$_2$—(CH$_2$)q-SO$_2$—(CH$_2$)q- in which q stands for an integer of from 1 to 3, $R^5$ and $R^6$ each independently represent an alkyl group having 1 to 20 carbon atoms, haloalkyl group having 1 to 20 carbon atoms, phenyl group which may be substituted by W, or thienyl group which may be substituted by W, $R^4$ and $R^7$ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 10 carbon atoms, monoalkylamino group having 1 to 10 carbon atoms, dialkylamino group having 1 to 10 carbon atoms, or phenyl group which may be substituted by W, W represents a halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', N-naphthyl-N-anthranylamino group which may be substituted by W', trialkylsilyl group having 1 to 10 carbon atoms, alkylcarbonyl group having 1 to 10 carbon atoms, alkoxycarbonyl group having 1 to 10 carbon atoms, or phenyl group which may be substituted by W', W' represents an alky group having 1 to 10 carbon atoms, haloalkyl group having 1 to 10 carbon atoms, or alkoxy group having 1 to 10 carbon atoms, m", n" and o" each independently stand for 0 or an integer of 1 or greater, p' stands for 0 or an integer of 1 or greater, and m", n", o" and p' satisfy m"+n"+o"≧1 and 50<m"+n"+o"+p'<5,000, Z is at least one divalent organic group selected from the following formulas [3] to [11]:

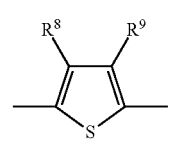
[3]

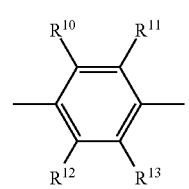
[4]

-continued

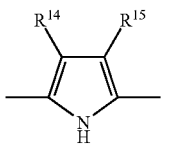

[5]

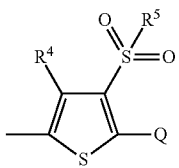

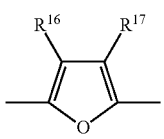

[6]

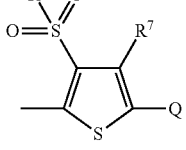

[13]

[14]

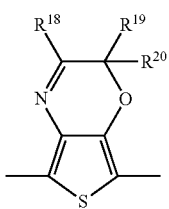

[7]

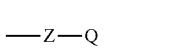

[15]

—Z—Q wherein $R^3$ to $R^7$ and Z have the same meanings as defined above, Q are both end groups of said sulfonyithiophene oligomer compound and each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, and W has the same meaning as defined above.

4. The sulfonyithiophene polymer compound according to claim 3, wherein Z is a divalent organic group represented by the formula [3].

5. A sulfonylthiophene oligomer compound represented by the following formula [16]:

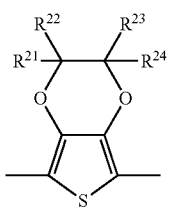

[8]

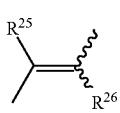

[9]

[10]

[11]

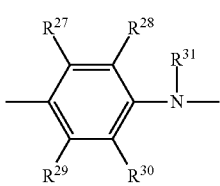

[16]

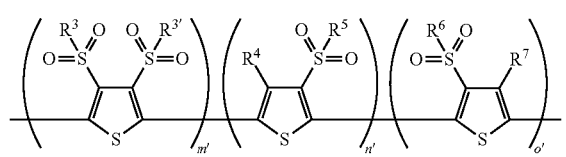

wherein $R^3$ and $R^{3'}$ each independently represent an alkyl group having 1 to 20 carbon atoms, haloalkyl group having 1 to 20 carbon atoms, phenyl group which may be substituted by W, or thienyl group which may be substituted by W, or $R^3$ and $R^{3'}$ are fused together to represent an alkylene group which has 1 to 3 carbon atoms and may be substituted by W, phenylene group which may be substituted by W, or —(CH$_2$)q-SO$_2$—(CH$_2$)q-SO$_2$—(CH$_2$)q- in which q stands for an integer of from 1 to 3, $R^5$ and $R^6$ each independently represent an alkyl group having 1 to 20 carbon atoms, haloalkyl group having 1 to 20 carbon atoms, phenyl group which may be substituted by W, or thienyl group which may be substituted by W, $R^4$ and $R^7$ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 wherein $R^8$ to $R^{30}$ each independently represent a hydrogen atom, alkyl group having 1 to 20 carbon atoms, haloalkyl group having 1 to 20 carbon atoms, alkoxy group having 1 to 10 carbon atoms, alkylthio group having 1 to 20 carbon atoms, dialkylamino group having 1 to 10 carbon atoms, or phenyl group which may be substituted by W, W has the same meaning as defined above, $R^{31}$ represents a hydrogen atom, alkyl group having 1 to 20 carbon atoms, haloalkyl group having 1 to 20 carbon atoms, alkoxy group having 1 to 10 carbon atoms, or phenyl group which may be substituted by W', and W' has the same meaning as defined above, and $Y^1$ and $Y^2$ each independently represent at least one monovalent organic group selected from the following formulas [12] to [15]:

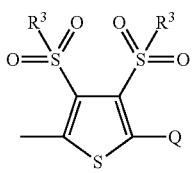

[12]

carbon atoms, alkylthio group having 1 to 20 carbon atoms, monoalkylamino group having 1 to 10 carbon atoms, dialkylamino group having 1 to 10 carbon atoms, or phenyl group which may be substituted by W, W represents a halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', N-naphthyl-N-anthranylamino group which may be substituted by W', trialkylsilyl group having 1 to 10 carbon atoms, alkylcarbonyl group having 1 to 10 carbon atoms, alkoxycarbonyl group having 1 to 10 carbon atoms, or phenyl group which may be substituted by W', W' represents an alky group having 1 to 10 carbon atoms, haloalkyl group having 1 to 10 carbon atoms, or alkoxy group having 1 to 10 carbon atoms, and m' stands for an integer of 1 or greater, n' and o' each independently stand for 0 or an integer of 1 or greater, and m', n' and o' satisfy $2 \leq m'+n'+o' \leq 50$, with a proviso that both ends of said sulfonylthiophene oligomer compound each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, and W has the same meaning as defined above.

6. A sulfonylthiophene polymer compound represented by the following formula [26]:

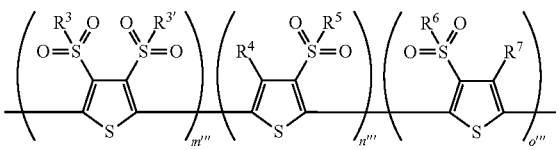

[26]

wherein $R^3$ and $R^{3'}$ each independently represent an alkyl group having 1 to 20 carbon atoms, haloalkyl group having 1 to 20 carbon atoms, phenyl group which may be substituted by W, or thienyl group which may be substituted by W, or $R^3$ and $R^{3'}$ are fused together to represent an alkylene group which has 1 to 3 carbon atoms and may be substituted by W, phenylene group which may be substituted by W, or
—$(CH_2)q$-$SO_2$—$(CH_2)q$-$SO_2$—$(CH_2)q$- in which q stands for an integer of from 1 to 3, $R^5$ and $R^6$ each independently represent an alkyl group having 1 to 20 carbon atoms, haloalkyl group having 1 to 20 carbon atoms, phenyl group which may be substituted by W, or thienyl group which may be substituted by W, $R^4$ and $R^7$ each independently represent a hydrogen atom, halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, or phenyl group which may be substituted by W, W represents a halogen atom, cyano group, nitro group, hydroxyl group, mercapto group, amino group, formyl group, carboxyl group, alkyl group having 1 to 20 carbon atoms, haloalkyl group having 1 to 20 carbon atoms, alkenyl group having 1 to 10 carbon atoms, alkynyl group having 1 to 10 carbon atoms, alkoxy group having 1 to 10 carbon atoms, alkylthio group having 1 to 20 carbon atoms, monoalkylamino group having 1 to 10 carbon atoms, dialkylamino group having 1 to 10 carbon atoms, diphenylamino group which may be substituted by W', dinaphthylamino group which may be substituted by W', dianthranylamino group which may be substituted by W', N-phenyl-N-naphthylamino group which may be substituted by W', N-phenyl-N-anthranylamino group which may be substituted by W', N-naphthyl-N-anthranylamino group which may be substituted by W', trialkylsilyl group having 1 to 10 carbon atoms, alkylcarbonyl group having 1 to 10 carbon atoms, alkoxycarbonyl group having 1 to 10 carbon atoms, or phenyl group which may be substituted by W', W' represents an alky group having 1 to 10 carbon atoms, haloalkyl group having 1 to 10 carbon atoms, or alkoxy group having 1 to 10 carbon atoms, and m''', n''' and o''' each independently stand for 0 or an integer of 1 or greater, and n''', and o''' satisfy $50 < m'''+n'''+o''' < 5,000$, with a proviso that both end groups of said sulfonylthiophene polymer compound each independently represent a hydrogen atom, halogen atom, cyano group, phenyl group which may be substituted by W, naphthyl group which may be substituted by W, anthranyl group which may be substituted by W, hydroxyl group, amino group, formyl group, carboxyl group, dihydroxyboryl group, alkyl group having 1 to 20 carbon atoms, haloalkyl group having 1 to 20 carbon atoms, monoalkylamino group having 1 to 10 carbon atoms, dialkylamino group having 1 to 10 carbon atoms, trialkylstannyl group having 1 to 10 carbon atoms, trialkylsilyl group having 1 to 10 carbon atoms, or dialkoxyboryl group having 1 to 10 carbon atoms, and W has the same meaning as defined above.

7. A sulfonylthiophene polymer compound obtained by subjecting at least one sulfonylthiophene oligomer compound, which is a sulfonylthiophene oligomer compound according to any one of claims 1 and 5, to electrolytic oxidative polymerization or chemical oxidative polymerization.

8. A process for the production of a sulfonylthiophene polymer compound, which comprises subjecting at least one sulfonylthiophene oligomer compound, which is a sulfonylthiophene oligomer compound according to any oneof claims 1 and 5, to electrolytic oxidative polymerization or chemical oxidative polymerization.

9. A sulfonylthiophene polymer compound obtained by subjecting at least one compound, which is selected from sulfonylthiophene oligomer compounds according to claim 1 or 5, to catalytic polymerization.

10. An active material for cells, comprising at least one compound selected from any one of claims 1, 2, 3, 4, 5, and 6.

11. An electrode material comprising at least one compound selected from any one of claims 1, 2, 3, 4, 5, and 6.

12. An organic electroluminescence material comprising at least one compound selected from any one of claims 1, 2, 3, 4, 5, and 6.

13. An n-type semiconductor formed by reducing at least one compound, which is selected from any one of claims 1, 2, 3, 4, 5, and 6 with a reductant or by electrochemical doping.

14. A semiconductor device fabricated by using at least one compound selected from any one of claims 1, 2, 3, 4, 5, and 6.

15. An organic electroluminescence device fabricated by using at least one compound selected from any one of claims 1, 2, 3, 4, 5, and 6.

16. An all-solid-state organic solar cell fabricated by using at least one compound selected from any one of claims 1, 2, 3, 4, 5, and 6.

17. A dye-sensitized solar cell fabricated by using at least one compound selected from any one of claims 1, 2, 3, 4, 5, and 6.

18. A capacitor electrode formed by using at least one compound selected from any one of claims 1, 2, 3, 4, 5, and 6.

19. An actuator formed by using at least one compound selected from any one of claims 1, 2, 3, 4, 5, and 6.

20. A solid electrolyte for capacitors, comprising at least one compound any one of claims 1, 2, 3, 4, 5, and 6.

21. An antenna material comprising at least one compound selected from any one of claims 1, 2, 3, 4, 5, and 6.

22. A sensor formed by using at least one compound selected from any one of claims 1, 2, 3, 4, 5, and 6.

23. A fuel cell separator comprising at least one compound selected from any one of claims 1, 2, 3, 4, 5, and 6.

* * * * *